(12) United States Patent
Vielhaber et al.

(10) Patent No.: US 9,060,949 B2
(45) Date of Patent: Jun. 23, 2015

(54) MENTHYL CARBAMATE COMPOUNDS AS SKIN AND/OR HAIR LIGHTENING ACTIVES

(75) Inventors: Gabriele Vielhaber, Paris (FR); Heiko Oertling, Lausanne (CH); Karin Schaper, Linnenkamp (DE); Claudia Gömann, Golmbach-Warbsen (DE); Rahim Brodhage, Höxter (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 13/699,543

(22) PCT Filed: May 25, 2010

(86) PCT No.: PCT/EP2010/057119
§ 371 (c)(1),
(2), (4) Date: Feb. 1, 2013

(87) PCT Pub. No.: WO2010/097480
PCT Pub. Date: Sep. 2, 2010

(65) Prior Publication Data
US 2013/0129646 A1    May 23, 2013

(51) Int. Cl.
| | | |
|---|---|---|
| A61Q 19/02 | (2006.01) |
| A61Q 17/04 | (2006.01) |
| A61Q 19/00 | (2006.01) |
| A61K 8/40  | (2006.01) |
| A61K 8/44  | (2006.01) |
| A61K 31/325| (2006.01) |
| A61Q 5/08  | (2006.01) |
| A61K 8/49  | (2006.01) |
| A61Q 5/00  | (2006.01) |
| A61Q 17/00 | (2006.01) |

(52) U.S. Cl.
CPC ... *A61K 8/40* (2013.01); *A61K 8/44* (2013.01); *A61K 31/325* (2013.01); *A61Q 5/08* (2013.01); *A61Q 19/02* (2013.01); *A61K 8/4973* (2013.01); *A61Q 5/00* (2013.01); *A61Q 17/00* (2013.01)

(58) Field of Classification Search
None
See application file for complete search history.

(56) References Cited

U.S. PATENT DOCUMENTS

| | | | |
|---|---|---|---|
| 5,703,123 | A | 12/1997 | Pelzer et al. |
| 5,833,998 | A * | 11/1998 | Biedermann et al. .......... 424/401 |
| 6,372,795 | B1 * | 4/2002 | Bajor et al. .................... 514/579 |
| 2002/0107282 | A1 | 8/2002 | Chevalier et al. |
| 2002/0161041 | A1 | 10/2002 | Browning et al. |
| 2003/0011990 | A1 | 1/2003 | Lai et al. |
| 2004/0209949 | A1 | 10/2004 | Browning et al. |
| 2006/0257340 | A1 * | 11/2006 | Nair ............................... 424/62 |
| 2009/0311401 | A1 | 12/2009 | Ley et al. |

FOREIGN PATENT DOCUMENTS

| | | |
|---|---|---|
| CN | 1240439 A | 1/2000 |
| DE | 1792331 U | 7/1959 |
| DE | 4226043 A1 | 2/1994 |
| JP | 6-199740 | 7/1994 |
| JP | 2003535915 A | 12/2003 |
| JP | 2004501950 A | 1/2004 |
| JP | 2007503392 A | 2/2007 |
| JP | 2009144179 A | 7/2009 |
| JP | 2013511542 A | 4/2013 |
| JP | 2013511543 A | 4/2013 |
| WO | WO-9721678 A1 | 6/1997 |
| WO | WO-0202071 A2 | 1/2002 |
| WO | WO-2009144179 A1 | 12/2009 |

OTHER PUBLICATIONS

Vazquez et al. ("Vazquez", J. of Ethnopharmacology, 1996, 55, 69-75).*
International search report with references cited and written opinion under Rule 43 PCT attached to the search report, International Application No. PCT/EP2010/057119, filed May 25, 2010.
Chinese Office Action, issued in parallel Chinese Application No. 201080068226.5 on Dec. 4, 2013.
Global cosmetics, China Cosmetics Review, vol. 3, pp. 24-27, Dec. 31, 2009.

(Continued)

*Primary Examiner* — Misook Yu
*Assistant Examiner* — Kauser M Akhoon
(74) *Attorney, Agent, or Firm* — Novak Druce Connolly Bove + Quigg LLP

(57) ABSTRACT

The present invention relates to the cosmetic, dermatological or pharmaceutical (therapeutic) use of compounds of formula (I) or a cosmetically acceptable salt of a compound of formula (I) or a mixture containing two or more of these compounds or the salts thereof

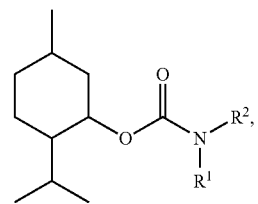

(I)

wherein
$R^1$ denotes hydrogen or an organic radical having 1 to 14 carbon atoms,
$R^2$ denotes an organic radical having 1 to 14 carbon atoms, and
wherein optionally $R^1$ and $R^2$ are covalently bonded to one another, preferably so that a 3 to 8 membered ring is formed, for the lightening of skin and/or hair.
The invention further relates to compositions and cosmetic, dermatological or pharmaceutical preparations (compositions) comprising one or more compounds of formula (I) suitable for lightening human skin and/or hair and corresponding methods. The invention further relates to compounds of formula (I) as a drug, their use for the preparation of a pharmaceutical composition for lightening human skin and/or hair and to certain novel compounds of formula (I).

13 Claims, No Drawings

(56) References Cited

OTHER PUBLICATIONS

Chinese Office Action, issued in parallel Chinese Application No. 201080068226.5 on Aug. 19, 2014.
Fragrance Journal, 2005, vol. 5, pp. 38-42.
JP407213, 2000, 1, 1, pp. 27-35.
Office Action from the Japanese Patent Office issued in Japanese Patent Application No. 2013-511544 dated Jul. 25, 2014.
Office Action from the European Patent Office issued in parallel European Application No. 10 721 158.3, dated Jul. 18, 2014.

* cited by examiner

MENTHYL CARBAMATE COMPOUNDS AS SKIN AND/OR HAIR LIGHTENING ACTIVES

CROSS-REFERENCE TO RELATED APPLICATIONS

This application is a national stage application (under 35 U.S.C. §371) of PCT/EP2010/057119, filed May 25, 2010, which is incorporated herein by reference in its entirety.

The present invention relates to the cosmetic, dermatological or pharmaceutical (therapeutic) use of certain menthyl carbamate compounds of formula (I) given below, in particular as skin and/or hair lightening (whitening) actives. The invention further relates to compositions and cosmetic, dermatological or pharmaceutical preparations (compositions) comprising one or more compounds of formula (I) suitable for lightening human skin and/or hair and corresponding methods. The invention further relates to compounds of formula (I) as a drug, their use for the preparation of a pharmaceutical composition for lightening human skin and/or hair and to certain novel compounds of formula (I).

Skin-lightening active ingredients intervene in one form or another in melanin metabolism or catabolism. Melanin pigments, which are normally brown to black in colour, are formed in the melanocytes of the skin, transferred to the keratinocytes and give the skin or hair its colour. In mammals, the brown-black eumelanins are primarily formed from hydroxy-substituted aromatic amino acids such as L-tyrosine and L-DOPA, the yellow to red pheomelanins additionally from sulfur-containing molecules (Cosmetics & Toiletries 1996, 111 (5), 43-51). Starting from L-tyrosine, L-3,4-dihydroxyphenylalanine (L-DOPA) is formed by the copper-containing key enzyme tyrosinase and is in turn converted by tyrosinase to dopachrome. By a series of steps catalysed by various enzymes, the latter is oxidised to form melanin.

Skin-lightening agents are used for various reasons: if for some reason the melanin-forming melanocytes in human skin are not evenly distributed, pigment spots occur which are either lighter or darker than the surrounding skin area. To overcome this problem, skin and hair lightening agents are sold which at least partially help to balance out such pigment spots. In addition, many people have a need to lighten their naturally dark skin colour or to prevent skin pigmentation. This requires very safe and effective skin and hair lightening agents. Many skin and hair lightening agents contain more or less powerful tyrosinase inhibitors. This is only one possible route towards skin and hair lightening, however.

Furthermore, UV-absorbing substances are also used to protect against the increase in skin pigmentation caused by UV light. This is a purely physically induced effect, however, and must be distinguished from the biological action of skin-lightening agents on cellular melanin formation, which can also be detected in the absence of UV light. Moreover, UV absorbers do not bring about a true lightening of the skin but merely inhibit the increase in skin pigmentation caused by UV light.

Cosmetic or pharmaceutical (therapeutic) preparations with skin and/or hair lightening activity are known from the prior art.

U.S. Pat. No. 4,959,393 discloses 4-alkyl-resorcinols as skin and/or hair lightening agents.

WO 2004/105736 teaches certain diphenylmethane-derivatives as skin and/or hair lightening agents.

WO 2007/110415 proposes certain diacetyl trimers as skin and/or hair lightening agents.

Hydroquinone, hydroquinone derivatives such as e.g. arbutin, vitamin C, derivatives of ascorbic acid such as e.g. ascorbyl palmitate, kojic acid and derivatives of kojic acid such as e.g. kojic acid dipalmitate, are used in particular in commercial cosmetic or therapeutic skin and hair lightening preparations.

One of the most commonly used skin and hair lighteners is hydroquinone. However, this compound has a cytotoxic effect on melanocytes and is irritating to the skin. For that reason such preparations are no longer authorised for cosmetic applications in Europe, Japan and South Africa, for example. In addition, hydroquinone is very sensitive to oxidation and can be stabilised only with difficulty in cosmetic formulations.

Arbutin (beta-arbutin) is a hydroquinone glucoside, which hydrolyses in situ to form hydroquinone and is therefore just as questionable in toxicological terms as hydroquinone.

Vitamin C and ascorbic acid derivatives have only an inadequate effect on the skin. Furthermore, they do not act directly as tyrosinase inhibitors but instead reduce the coloured intermediate stages of melanin biosynthesis.

Kojic acid (5-hydroxy-2-hydroxymethyl-4-pyranone) is a tyrosinase inhibitor which inhibits its catalytic action by chelating the copper atoms in the enzyme; it is used in commercial skin and hair lightening agents but has a high sensitising potential and causes contact allergies.

The object of the present invention was to remedy the disadvantages of the prior art and in particular to provide effective skin and/or hair lightening actives, in particular skin lightening actives, which preferably achieve skin and/or hair lightening activity which preferably is not based on tyrosinase inhibition.

It has surprisingly been found that this object can be achieved by using compounds of formula (I) or a cosmetically acceptable salt of a compound of formula (I) or a mixture containing two or more of these compounds or the salts thereof

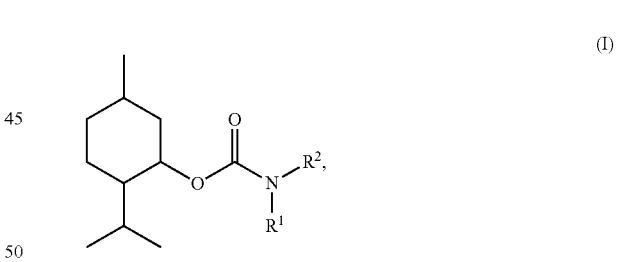

(I)

wherein
$R^1$ denotes hydrogen or an organic radical having 1 to 14 carbon atoms,
$R^2$ denotes an organic radical having 1 to 14 carbon atoms, and
wherein optionally $R^1$ and $R^2$ are covalently bonded to one another, preferably so that a 3 to 8 membered ring is formed, for the lightening of skin and/or hair.

The compounds of formula (I) show pronounced skin and/or hair lightening effects. The invention therefore relates to cosmetic or pharmaceutical preparations (compositions) containing a corresponding effective quantity of one or more compounds of formula (I), in particular for the topical lightening of skin and/or hair.

The compounds of formula (I) structurally belong to the group of menthyl carbamates.

As common in the art, a "flat" structural formula, i.e. a graphical formula which does not convey any stereochemical information and gives no concrete information about the three-dimensional structure thereof, relates to and includes all stereoisomers of said structural formula. For the sake of clarity, menthyl-carbamates of "flat" structural formula (I) thus include all stereoisomeric forms thereof, i.e. the menthyl-, neomenthyl-, isomenthyl- and neoisomenthyl-carbamates, including their respective enantiomeric forms, as explained in more detail below.

The compounds according to the invention of formula (I) exist in different isomeric forms and may be used in the context of the present invention in all their isomeric forms, i.e.—depending on their structure—as enantiomers, diastereomers, syn-/anti-isomers, cis-/trans-isomers, epimers as well as (E)-/(Z)-isomers. The compounds of formula (I) can be used in the context of the present invention in the form of the pure stereoisomeric form or in the form of any mixture of stereoisomers. The compounds of formula (I) can also be used in the context of the present invention in the form of the pure enantiomers or in the form of any mixture of enantiomers, in the latter case racemates being preferred.

The menthyl carbamates of formula (I) are derived from 2-isopropyl-5-methylcyclohexanol (p-menthan-3-ol) which has three asymmetric carbon atoms in its cyclohexane ring and occurs as four pairs of enantiomers.

These isomers can be illustrated by the following formulae, showing one enantiomer each of the four diastereomers.

(IIa)

(-)-Menthol (IIb)

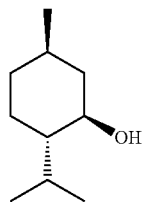

(+)-Neomenthol (IIc)

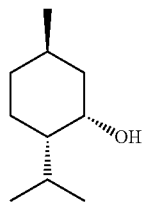

(+)-Isomenthol

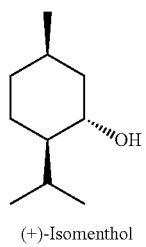

(IId)

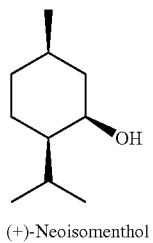

(+)-Neoisomenthol

The enantiomers (IIa) to (IId) and their optical antipodes may, for example, be obtained by hydrogenation of thymol (e.g. WO 2004/018398 and the references cited therein) or via cyclization of citronellal to the corresponding isopulegol-isomers and subsequent hydrogenation. The menthol isomers can be separated via accurate distillation (for more details on manufacturing and separation of menthol isomers see "Common Fragrance and Flavor Materials", 4th Edition, Wiley-VCH, Weinheim 2001, 52-55).

Structurally derived from the enantiomers (IIa) to (IId) and their optical antipodes are the following compounds of formula (I). Compounds (Ia) are derived from (−)-menthol (IIa), compounds (ent-Ia) are derived from (+)-menthol, compounds (Ib) are derived from (+)-neomenthol (IIb), compounds (ent-Ib) are derived from (−)-neomenthol and so forth.

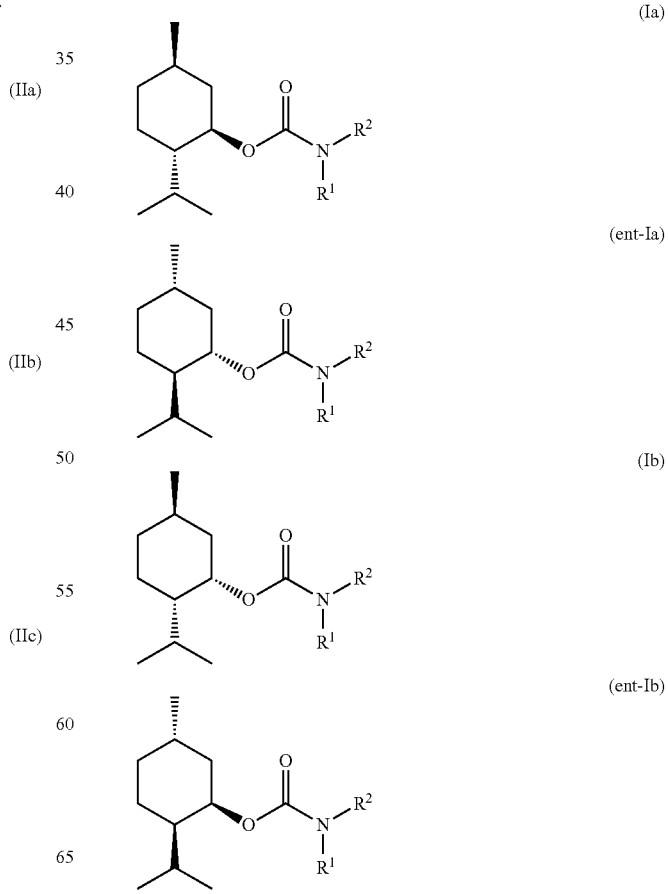

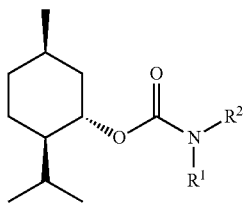
(Ic)

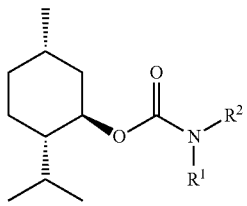
(ent-Ic)

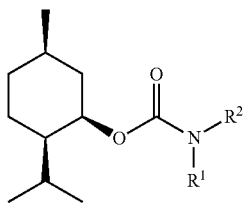
(Id)

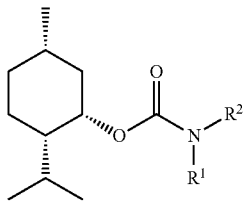
(ent-Id)

wherein $R^1$ and $R^2$ in each formula (Ia), (ent-Ia), (Ib), (ent-Ib), (Ic), (ent-Ic), (Id) and (ent-Id) mutually independently have the (preferred) meaning given hereinbefore or hereinafter.

As common in the art, in the context of the present invention, abbreviations for certain chemical groups are used, for example Me=methyl, Et=ethyl, Pr=propyl, Bu=butyl, Ph=phenyl.

Various menthyl carbamates of formula (I) have been described in the prior art.

EP 2 135 516 discloses several neomenthyl-carbamates as umami-flavor substances, inter alia the following:

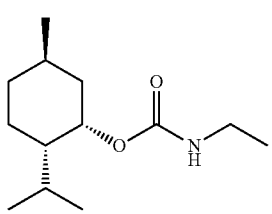

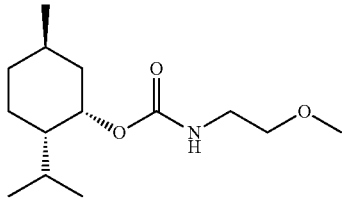

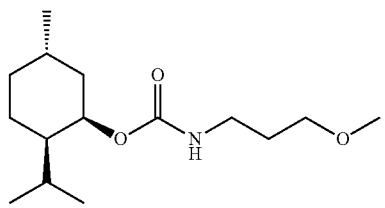

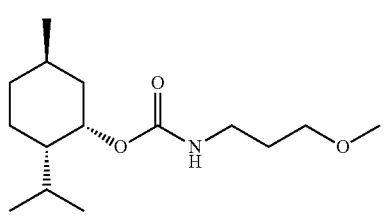

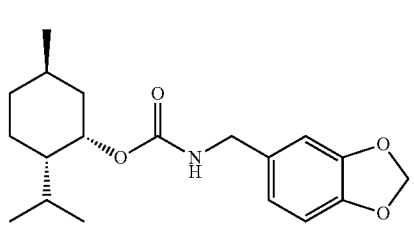

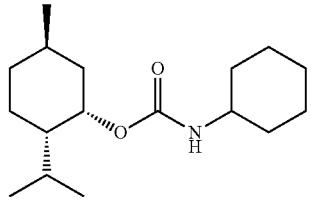

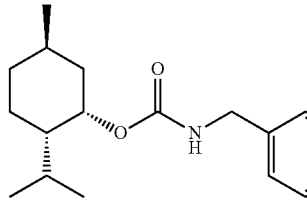

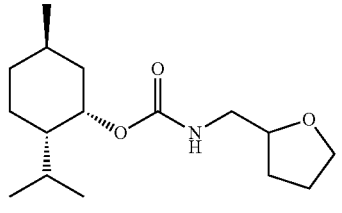 [SMILES: CC(C)[C@@H]1CC[C@@H](C)C[C@@H]1OC(=O)NCC1CCCO1]

WO 2004/000023 describes the following 1-menthyl-carbamates as insect repellents:

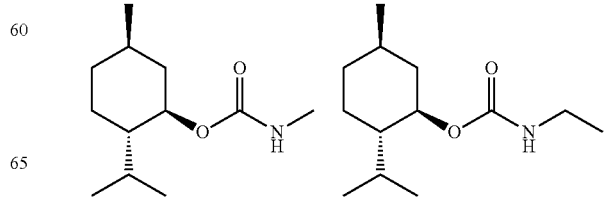

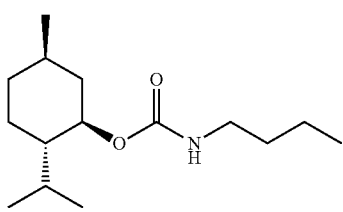

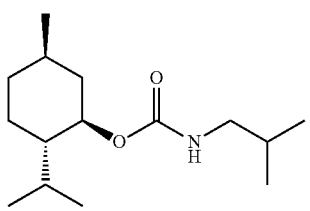

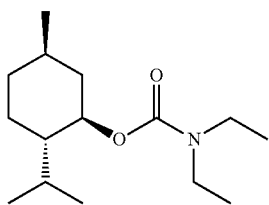

J. Org. Chem. 1999, 7921-7928 discloses N,N-diethyl (−)-(1R)-menthyl carbamate:

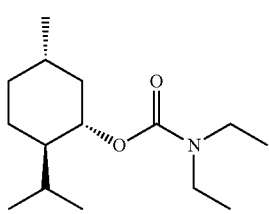 [SMILES: CCN(CC)C(=O)O[C@H]1C[C@@H](C)CC[C@@H]1C(C)C]

Polish Journal of Chemistry (1996), 70(3), 310-19 describes

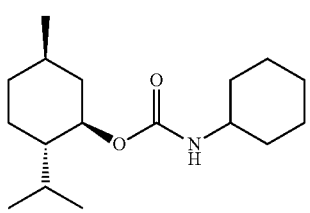

Advanced Synthesis & Catalysis (2008), 350(9), 1235-1240 and Organic & Biomolecular Chemistry (2005), 3(15), 2741-2749 disclose benzyl-carbamic acid (1R,2S,5R)/(1S,2R,5S)-2-isopropyl-5-methyl-cyclohexyl ester, respectively

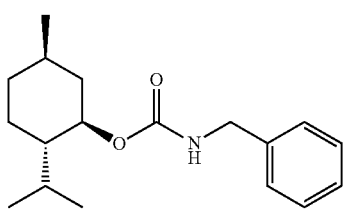

U.S. Pat. No. 5,703,123 discloses the following formula which does not convey any stereochemical information:

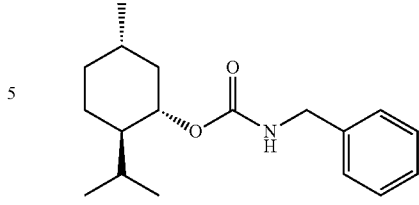

DE 1300725 discloses the following carbamate without including any stereochemical information:

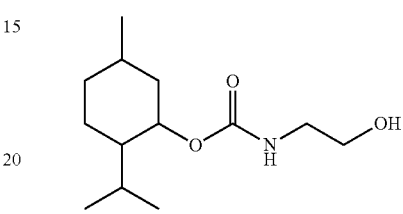

U.S. Pat. No. 6,150,415 discloses the following carbamate without including any stereochemical information:

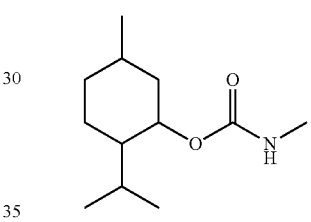

Angewandte Chemie (1982), 94(9), 709-710 describes all eight different enantiomers of isopropyl-carbamic acid 2-isopropyl-5-methyl-cyclohexyl ester:

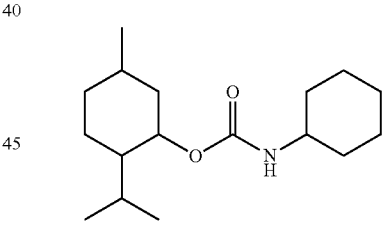

WO 2004/033422 relates to compounds inhibiting fatty acid amide hydrolase (FAAH). Methods are described therein to control appetite and treat appetite disorders by administering FAAH inhibitors, thereby reducing body fat or body weight.

WO 2004/033422 discloses a very broad generic chemical formula of carbamates which also embraces a vast number of substituted or unsubstituted cyloalkyl carbamates. No menthyl carbamates are explicitly disclosed.

EP 1 284 145 describes the use of N-2-(3,4-dihydroxyphenyl)ethyl-substituted carbonic acid derivatives as radical scavengers and antioxidants. EP 1 284 145 further describes cosmetic preparations containing said carbonic acid derivatives. The effect of these compounds on the metabolism of fat cells or the body weight of humans was not investigated there. The only explicitly mentioned compound in EP 1 284 145 of relevance in view of formula (I) of the present invention is N-[2-(3,4-dihydroxyphenyl)ethyl-O-(1R,3R,4S)-menthyl] carbamate. According to EP 1 284 145, cosmetic or dermatologic preparations may additionally comprise skin lightening substances, by way of example kojic acid, hydroquinone or arbutin are mentioned.

In a preferred embodiment, a cosmetic or pharmaceutical preparation according to the present invention is free of N-[2-(3,4-dihydroxyphenyl)ethyl-O-(1R,3R,4S)-menthyl]carbamate. In another preferred embodiment, compounds of formula (I) according to the present invention, more specifically compounds of formula (Ia), are excluded in which $R^2$ denotes a 2-(3,4-dihydroxyphenyl)ethyl-radical. In another preferred embodiment, cosmetic or pharmaceutical preparations according to the present invention are free of compounds of formula (I) according to the present invention, more specifically free of compounds of formula (Ia), in which $R^2$ denotes a 2-(3,4-dihydroxyphenyl)ethyl-radical.

WO 01/98235 describes the use of N-3,4-dihydroxybenzyl-substituted carbonic acid derivatives as radical scavengers and antioxidants. WO 01/98235 further describes cosmetic preparations containing said carbonic acid derivatives. The effect of these compounds on the metabolism of fat cells or the body weight of humans was not investigated there. The only explicitly mentioned compound in WO 01/98235 of relevance in view of formula (I) of the present invention is N-(3,4-dihydroxybenzyl)-O-(1R,3R,4S)-menthyl]carbamate. According to WO 01/98235, cosmetic or dermatologic preparations may additionally comprise skin lightening substances, by way of example kojic acid, hydroquinone or arbutin are mentioned.

In a preferred embodiment, a cosmetic or pharmaceutical preparation according to the present invention is free of N-(3,4-dihydroxybenzyl)-O-(1R,3R,4S)-menthyl]carbamate. In another preferred embodiment, compounds of formula (I) according to the present invention, more specifically compounds of formula (Ia), are excluded in which $R^2$ denotes a 3,4-dihydroxybenzyl-radical. In another preferred embodiment, cosmetic or pharmaceutical preparations according to the present invention are free of compounds of formula (I) according to the present invention, more specifically free of compounds of formula (Ia), in which $R^2$ denotes a 3,4-dihydroxybenzyl-radical.

In a preferred embodiment, compounds of formula (I) according to the present invention, more specifically of compounds of formula (Ia), are excluded in which $R^2$ denotes a radical containing a 3,4-dihydroxyphenyl-group. In another preferred embodiment, cosmetic or pharmaceutical preparations according to the present invention are free of compounds of formula (I) according to the present invention, more specifically free of compounds of formula (Ia), in which $R^2$ denotes a radical containing a 3,4-dihydroxyphenyl-group.

In another preferred embodiment, compounds of formula (I) according to the present invention, more specifically compounds of formula (Ia), are excluded in which $R^2$ denotes a radical containing a dihydroxyphenyl-group. In another preferred embodiment, cosmetic or pharmaceutical preparations according to the present invention are free of compounds of formula (I) according to the present invention, more specifically free of compounds of formula (Ia), in which $R^2$ denotes a radical containing a dihydroxyphenyl-group.

There is no indication hitherto that the compounds used in accordance with the present invention are suitable for cosmetic or therapeutic lightening of skin and/or hair.

In the context of the present invention, a cosmetic use or a cosmetic method is free of any therapeutic (side) effects.

In the context of the present invention, a therapeutic or pharmaceutical use or method is considered as medical treatment, optionally with cosmetic (side) effects.

The compounds according to the invention of formula (I), depending on their structure, may exist in different stereoisomeric forms and may be used in the context of the present invention as stereoisomers, enantiomers, diastereomers, syn-/anti-isomers, endo-/exo-isomers, cis-/trans-isomers or epimers. The compounds of formula (I) can be used in the context of the present invention in the form of the pure cis- or trans-, syn- or anti-diastereomer or in the form of any mixture of diastereomers. The compounds of formula (I) can also be used in the context of the present invention in the form of the pure enantiomers or in the form of any mixture of enantiomers, in the latter case racemates being preferred.

In case $R^1$ does not denote hydrogen, $R^1$ and $R^2$ independently of one another preferably denote an optionally substituted radical selected from the group consisting of alkyl, heteroalkyl, cycloalkyl, cycloalkylalkyl, alkenyl, cycloalkenyl, cycloalkenylalkyl, alkynyl, cycloalkylalkynyl, aryl, heteroaryl, arylalkyl, cycloalkylaryl, cycloalkenylaryl, cycloalkylheteroaryl, heterocycloalkylaryl, heterocycloalkenylaryl, heterocycloalkenylheteroaryl and heteroarylalkyl.

In case $R^1$ does not denote hydrogen, $R^1$ and $R^2$ independently of one another more preferably denote an optionally substituted radical $C_1$-$C_{14}$-alkyl, $C_1$-$C_{14}$-heteroalkyl, $C_3$-$C_{14}$-cycloalkyl, $C_4$-$C_{14}$-cycloalkylalkyl, $C_2$-$C_{14}$-alkenyl, $C_3$-$C_{14}$-cycloalkenyl, $C_4$-$C_{14}$-cycloalkenylalkyl, $C_2$-$C_{14}$-alkynyl, $C_5$-$C_{14}$-cycloalkylalkynyl, $C_3$-$C_{14}$-aryl, $C_2$-$C_{14}$-heteroaryl, $C_4$-$C_{14}$-arylalkyl, $C_8$-$C_{14}$-cycloalkylaryl, $C_8$-$C_{14}$-cycloalkenylaryl, $C_5$-$C_{14}$-cycloalkylheteroaryl, $C_8$-$C_{14}$-heterocycloalkylaryl, $C_8$-$C_{14}$-heterocycloalkenylaryl, $C_8$-$C_{14}$-heterocycloalkenylheteroaryl and $C_3$-$C_{14}$-heteroarylalkyl.

Heteroalkyl, heteroaryl, cycloalkylheteroaryl, heterocycloalkylaryl, heterocycloalkenylaryl, heterocycloalkenylheteroaryl and heteroarylalkyl radicals in the context of the present invention preferably contain at least one heteroatom, optionally up to four heteroatoms, selected independently from the group consisting of O, S and/or N. Preferred are heteroalkyl, heteroaryl, cycloalkylheteroaryl, heterocycloalkylaryl, heterocycloalkenylaryl, heterocycloalkenylheteroaryl and heteroarylalkyl radicals containing one, two or three heteroatoms, selected independently from the group consisting of O, S and/or N.

In preferred compounds of formula (I), $R^1$ denotes hydrogen. In our investigations, compounds of formula (I) wherein $R^1$ denotes hydrogen were generally found to have good to excellent activity and efficacy regarding skin and/or lightening.

In preferred compounds of formula (I), $R^2$ denotes an organic radical having 1 to 12 carbon atoms, preferably an organic radical having 1 to 10 carbon atoms, more preferably an organic radical having 1 to 8 carbon atoms.

In more preferred compounds of formula (I), $R^2$ denotes an optionally substituted radical $C_1$-$C_{10}$-alkyl, $C_1$-$C_{10}$-heteroalkyl, $C_3$-$C_{10}$-cycloalkyl, $C_4$-$C_{10}$-cycloalkylalkyl, $C_2$-$C_{10}$-alkenyl, $C_3$-$C_{10}$-cycloalkenyl, $C_4$-$C_{10}$-cycloalkenylalkyl, $C_2$-$C_{10}$-alkynyl, $C_5$-$C_{10}$-cycloalkylalkynyl, $C_3$-$C_{10}$-aryl, $C_2$-$C_{10}$-heteroaryl, $C_4$-$C_{10}$-arylalkyl, $C_8$-$C_{10}$-cycloalkylaryl, $C_8$-$C_{10}$-cycloalkenylaryl, $C_5$-$C_{10}$-cycloalkylheteroaryl, $C_8$-$C_{10}$-heterocycloalkylaryl, $C_8$-$C_{10}$-heterocycloalkenylaryl, $C_8$-$C_{10}$-heterocycloalkenylheteroaryl and $C_3$-$C_{10}$-heteroarylalkyl.

In even more preferred compounds of formula (I), $R^2$ denotes an optionally substituted radical chosen from the group consisting of $C_1$-$C_8$-alkyl, $C_3$-$C_8$-cycloalkyl, $C_4$-$C_{12}$-cycloalkylalkyl, $C_2$-$C_8$-alkenyl, $C_3$-$C_8$-cycloalkenyl, $C_4$-$C_8$-cycloalkenylalkyl, $C_3$-$C_8$-aryl, $C_2$-$C_8$-heteroaryl, $C_4$-$C_8$-arylalkyl, $C_5$-$C_8$-cycloalkylheteroaryl and $C_4$-$C_8$-heteroarylalkyl.

If the radicals $R^1$ and/or $R^2$ are substituted, $R^1$ and/or $R^2$ each may contain one or more heteroatoms, preferably independently selected from the group consisting of O, S, N, Si and F. If the heteroatoms are selected from the group consisting of O, S and N, the radicals $R^1$ and/or $R^2$ each preferably contain one, two or three heteroatoms selected independently from the group consisting of O, S and/or N.

If the radicals $R^1$ and/or $R^2$ are substituted the following substituents are preferred:
hydroxyl,
fluoride,
$C_1$-$C_8$-alkyl, preferably methyl, ethyl, n-propyl, iso-propyl, n-butyl, iso-butyl, tert-butyl,
$C_3$-$C_{12}$-cycloalkyl, preferably cyclopropyl, cyclopentyl, cyclohexyl, cyclooctyl, cyclododecyl,
$C_2$-$C_8$-alkynyl, preferably ethynyl, propynyl,
$C_1$-$C_8$-perfluoroalkyl, preferably trifluoromethyl, nonafluorobutyl,
$C_1$-$C_8$-alkoxy, preferably methoxy, ethoxy, n-propoxy, iso-propoxy, n-butoxy, iso-butoxy, tert-butoxy,
$C_3$-$C_8$-cycloalkoxy, preferably $C_3$-cycloalkoxy, $C_5$-cycloalkoxy, $C_6$-cycloalkoxy, $C_8$-cycloalkoxy,
$C_1$-$C_{10}$-alkoxyalkyl, in which 1 to 3 $CH_2$ groups are replaced by oxygen, preferably —[—O—$CH_2$—$CH_2$—]$_v$-Q or —[—O—$CH_2$—CHMe-]$_v$-Q, wherein Q is OH or $CH_3$ and wherein v denotes an integer from 1 to 3,
$C_1$-$C_4$-acyl, preferably acetyl,
$C_1$-$C_4$-acetal, preferably dimethylacetal, diethylacetal or a methylenedioxy group —O—$CH_2$—O—.
$C_1$-$C_4$-carboxyl, preferably $CO_2Me$, $CO_2Et$, $CO_2$ iso-Pr, $CO_2$tert-Bu,
$C_1$-$C_4$-acyloxy, preferably acetyloxy,
$Si_1$-$Si_{10}$-silyl, and
$Si_1$-$Si_{30}$-siloxy or polysiloxy.

Preferred cosmetically or pharmaceutically acceptable salts of compounds of formula (I) are those in which the one or more counterions (counteracting cation) is selected from the group consisting of $Na^+$, $K^+$, $NH_4^+$, trialkylammonium $NHR^i_3{}^+$, $Ca^{2+}$, $Mg^{2+}$, $Zn^{2+}$ and $Al^{3+}$.

In trialkylammonium $NHR^i_3{}^+$, preferably each $R^i$ independently of the other radicals $R^i$ denotes an alkyl group having 1 to 30 C-atoms, preferably having 4 to 22 C-atoms.

Particular preferred counterions are $Na^+$, $K^+$, $NH_4^+$, $Ca^{2+}$ and/or $Mg^{2+}$.

In case two different compounds of formula (I) are used as a mixture, generally the ratio by weight of the two compounds is chosen in the range of from 10:1 to 1:10, preferably in the range of from 5:1 to 1:5, more preferably in the range of from 3:1 to 1:3, the counterion, if present, not being included in the case of salts.

In the context of the present invention, a wavy line in structural formulae means that the double bond can be in the (E) or (Z) configuration.

Preferred compounds of formula (I) are those in which $NR^2$ is a radical chosen from the following list "N":

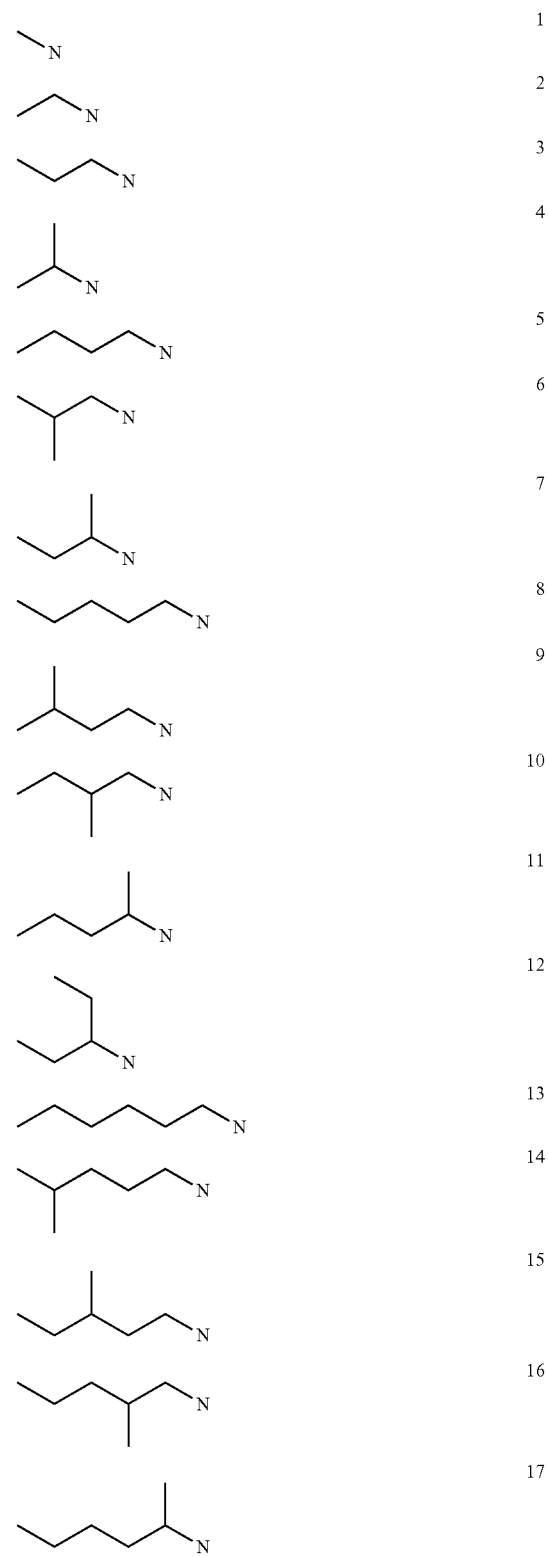

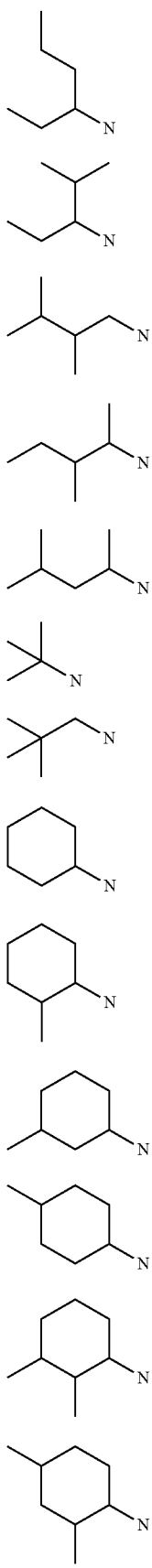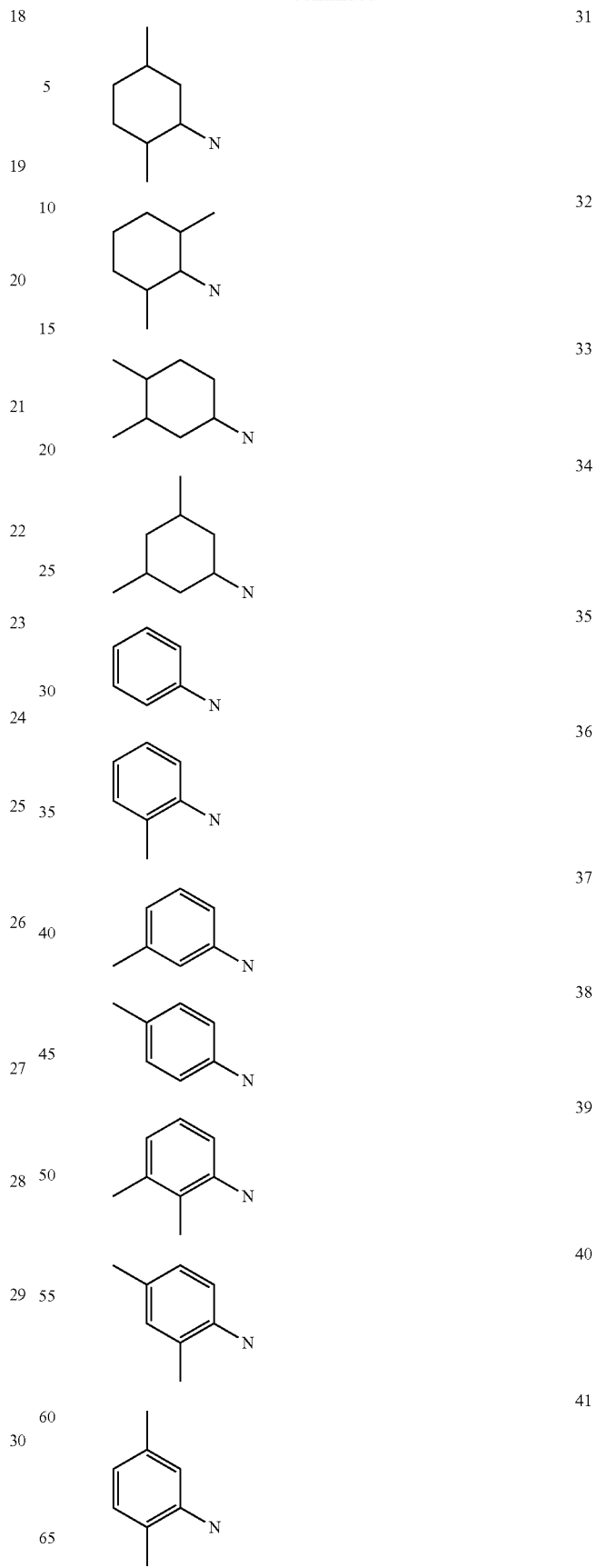

42
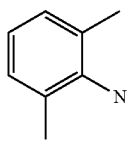
43
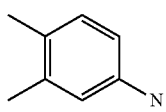
44
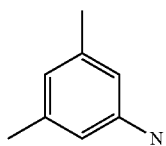
45
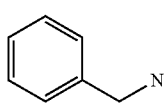
46
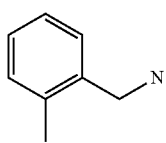
47
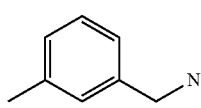
48
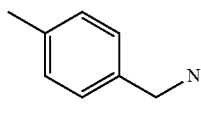
49
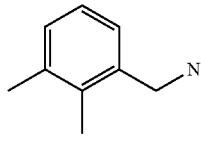
50
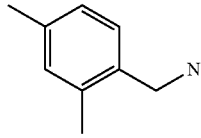
51
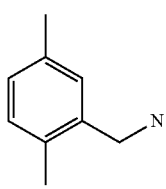
52
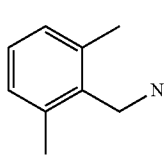
53
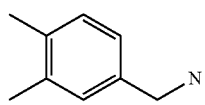
54
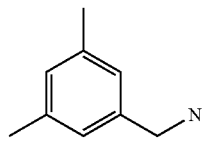
55
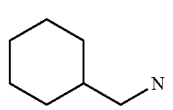
56
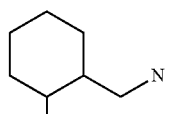
57
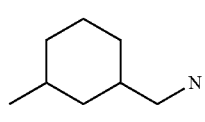
58
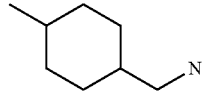
59
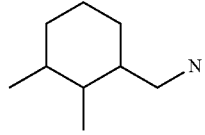
60
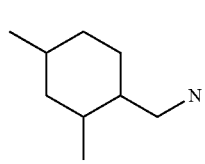
61
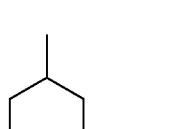
62
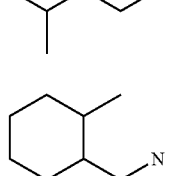
63
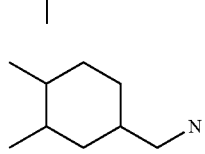

-continued
| | |
|---|---|
| 64 | 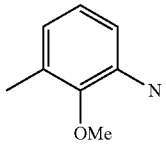 |
| 65 | 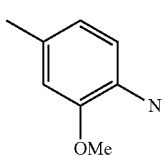 |
| 66 | 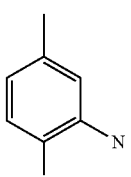 |
| 67 | 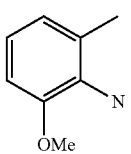 |
| 68 | 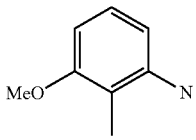 |
| 69 | 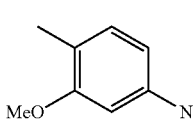 |
| 70 | 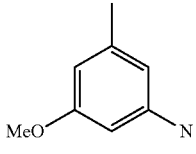 |
| 71 | 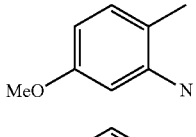 |
| 72 | 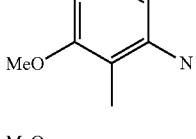 |
| 73 | 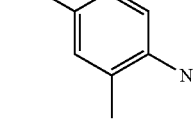 |
| 74 | 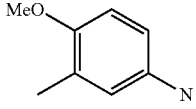 |
-continued
| | |
|---|---|
| 75 | 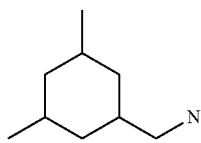 |
| 76 |  |
| 77 | 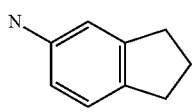 |
| 78 | 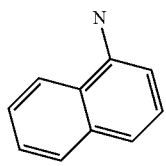 |
| 79 | 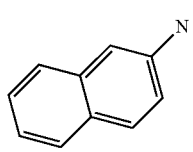 |
| 80 | 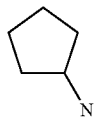 |
| 81 | 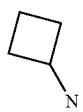 |
| 82 | 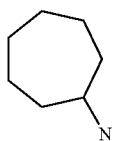 |
| 83 | 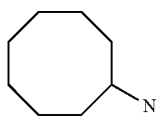 |
| 84 | 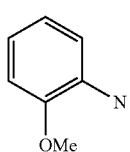 |
| 85 | 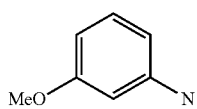 |
| 86 | 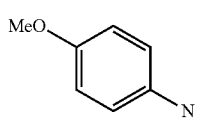 |

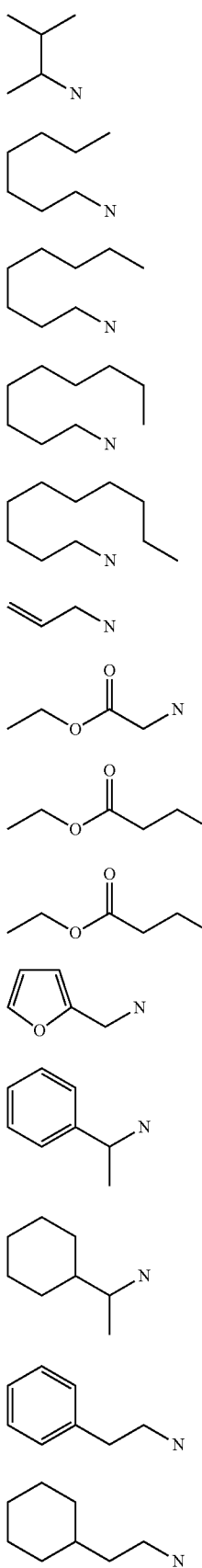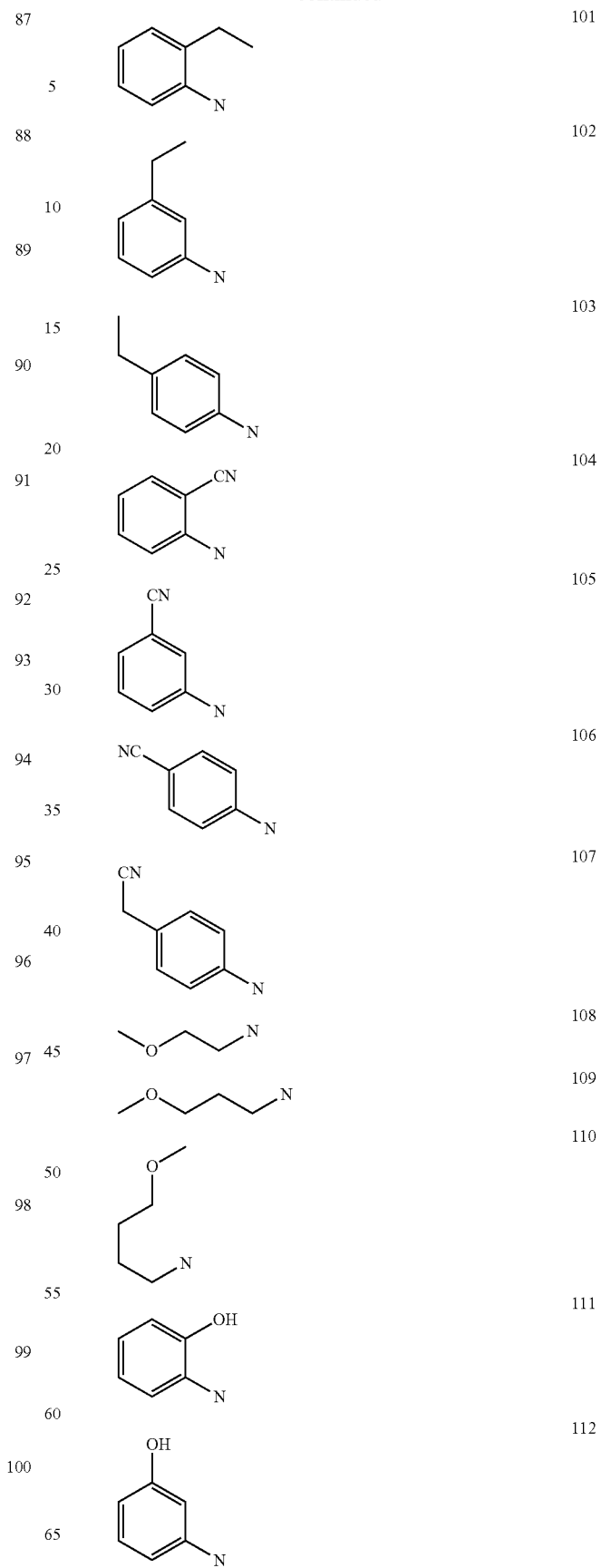

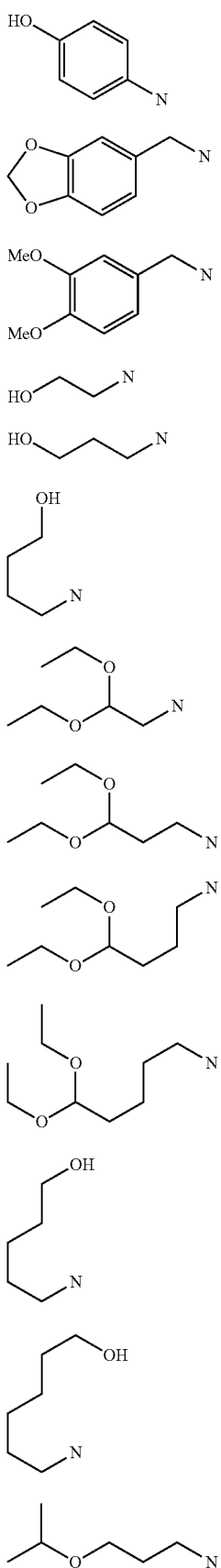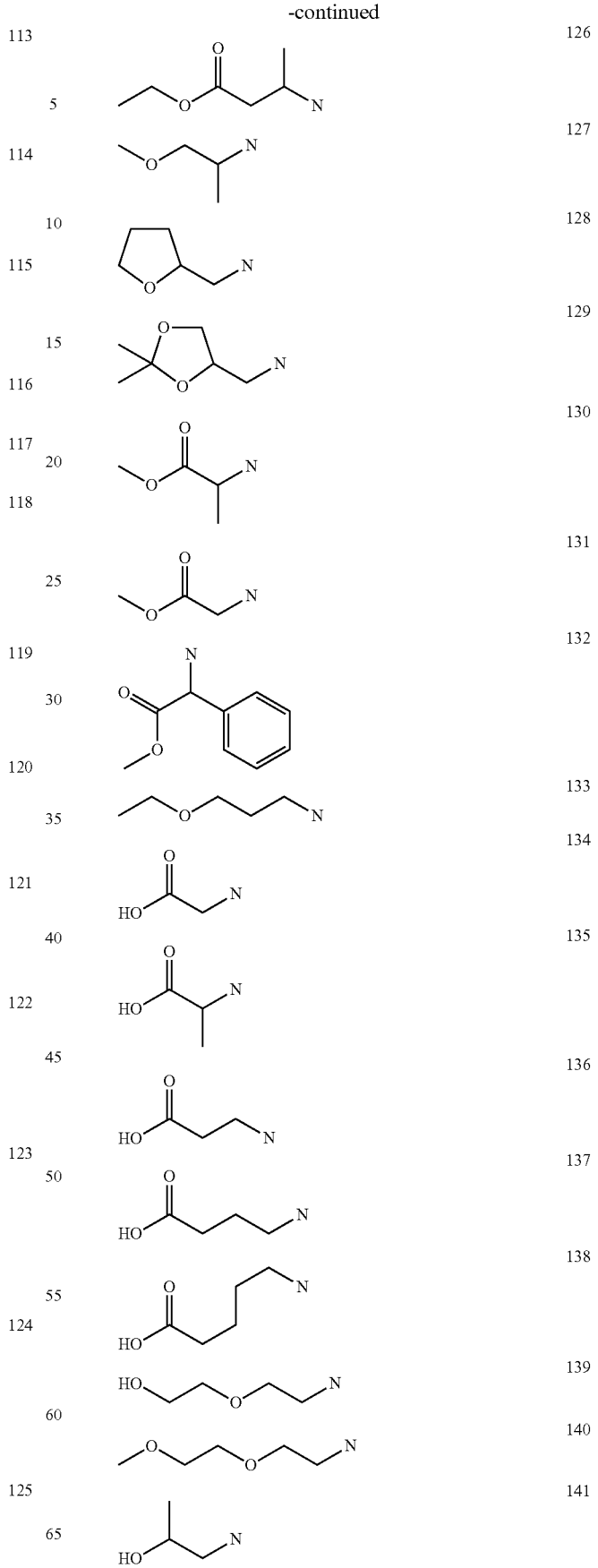

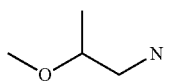
142

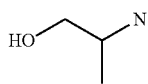
143

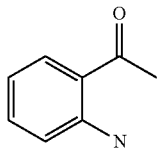
144

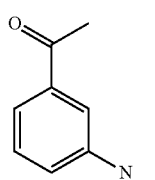
145

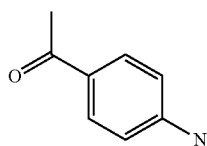
146

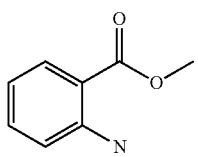
147

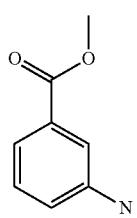
148

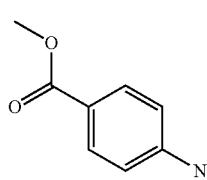
149

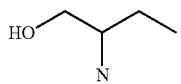
150

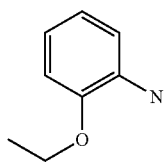
151

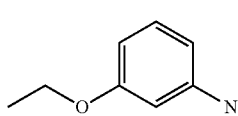
152

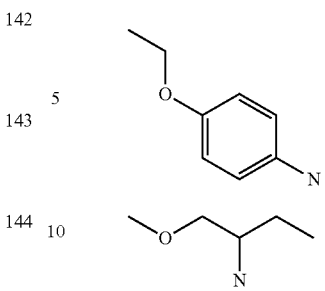
153

154

Further preferred compounds of formula (I) are those of formula (Ia) wherein $R^1$ denotes hydrogen and wherein $NR^2$ of formula (I) denotes one radical selected from list "N", above.

Further preferred compounds of formula (I) are those of formula (ent-Ia) wherein $R^1$ denotes hydrogen and wherein $NR^2$ of formula (I) denotes one radical selected from list "N", above.

Further preferred compounds of formula (I) are those of formula (Ib) wherein $R^1$ denotes hydrogen and wherein $NR^2$ of formula (I) denotes one radical selected from list "N", above.

Further preferred compounds of formula (I) are those of formula (ent-Ib) wherein $R^1$ denotes hydrogen and wherein $NR^2$ of formula (I) denotes one radical selected from list "N", above.

Other preferred compounds of formula (I) are those of formula (Ic) wherein $R^1$ denotes hydrogen and wherein $NR^2$ of formula (I) denotes one radical selected from list "N", above.

Other preferred compounds of formula (I) are those of formula (ent-Ic) wherein $R^1$ denotes hydrogen and wherein $NR^2$ of formula (I) denotes one radical selected from list "N", above.

Other preferred compounds of formula (I) are those of formula (Id) wherein $R^1$ denotes hydrogen and wherein $NR^2$ of formula (I) denotes one radical selected from list "N", above.

Other preferred compounds of formula (I) are those of formula (ent-Id) wherein $R^1$ denotes hydrogen and wherein $NR^2$ of formula (I) denotes one radical selected from list "N", above.

However, in the context of the present invention, and depending on the circumstances, each individual compound of the preferred compounds of formula (I) indicated above wherein $R^1$ denotes hydrogen and wherein $NR^2$ is a radical chosen from list "N", above, may for technical or non-technical reasons, as the case may be, in some embodiments be more preferred or less preferred than other preferred compounds. Thus, in some cases said compounds do not necessarily share the same level of preference.

Other preferred compounds of formulae (I) are those wherein $NR^1R^2$ is a radical chosen from the following list "D":

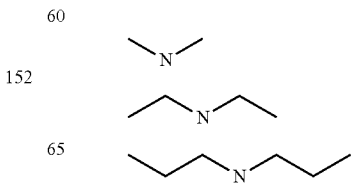
201

202

203

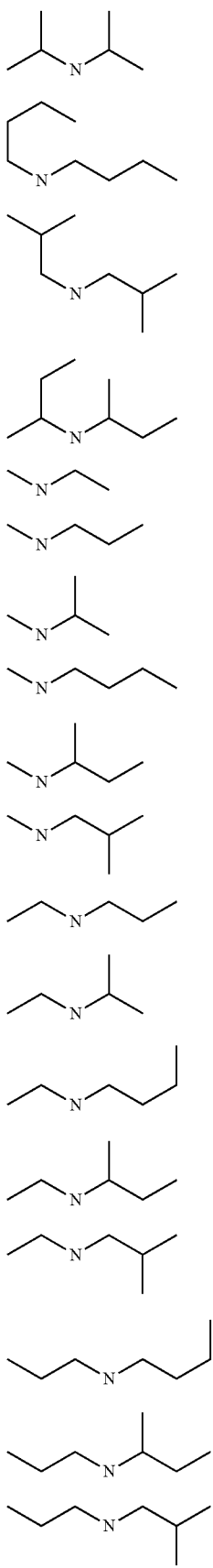
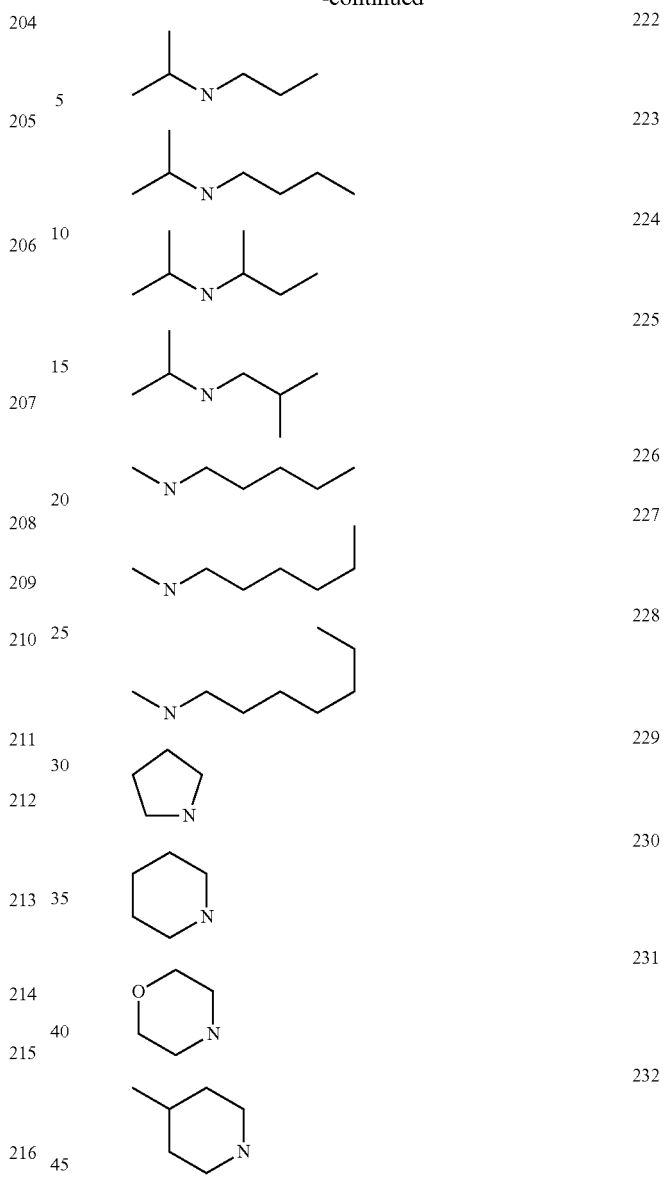

Further preferred compounds of formula (I) are those of formula (Ia) wherein $NR^1R^2$ is a radical chosen from list "D", above.

Further preferred compounds of formula (I) are those of formula (ent-Ia) wherein $NR^1R^2$ is a radical chosen from list "D", above.

Further preferred compounds of formula (I) are those of formula (Ib) wherein $NR^1R^2$ is a radical chosen from list "D", above.

Further preferred compounds of formula (I) are those of formula (ent-Ib) wherein $NR^1R^2$ is a radical chosen from list "D", above.

Other preferred compounds of formula (I) are those of formula (Ic) wherein $NR^1R^2$ is a radical chosen from list "D", above.

Other preferred compounds of formula (I) are those of formula (ent-Ic) wherein $NR^1R^2$ is a radical chosen from list "D", above.

Other preferred compounds of formula (I) are those of formula (Id) wherein $NR^1R^2$ is a radical chosen from list "D", above.

Other preferred compounds of formula (I) are those of formula (ent-Id) wherein NR¹R² is a radical chosen from list "D", above.

However, in the context of the present invention, and depending on the circumstances, each individual compound of the preferred compounds of formula (I) indicated above wherein NR¹R² is a radical chosen from list "D", above, may for technical or non-technical reasons, as the case may be, in some embodiments be more preferred or less preferred than other preferred compounds. Thus, in some cases said compounds do not necessarily share the same level of preference.

Due to their good to excellent activity and efficacy regarding the effects to be achieved in the context of the present invention, preferred compounds of formula (I) in accordance with the present invention are selected from the group consisting of:

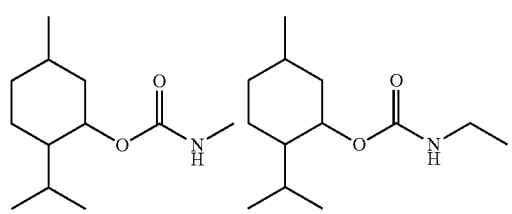

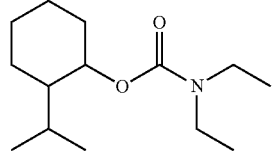

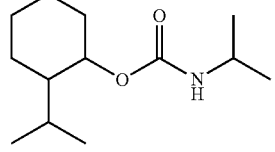

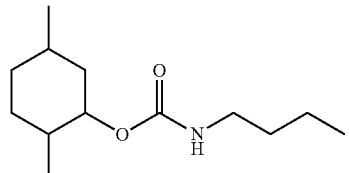

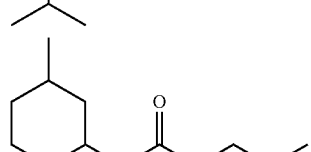

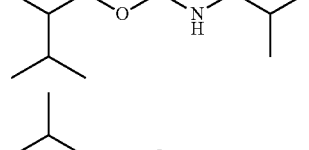

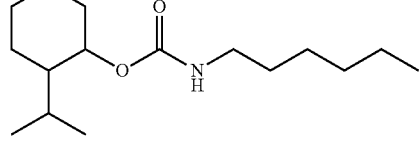

-continued

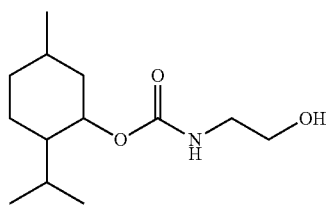 [SMILES: CC1CCC(C(C)C)C(OC(=O)NCCO)C1]

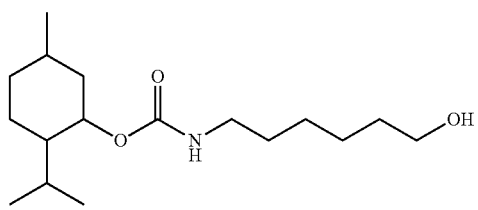

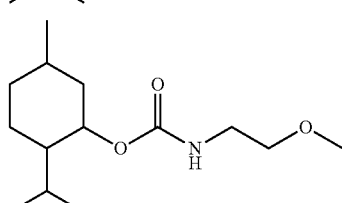

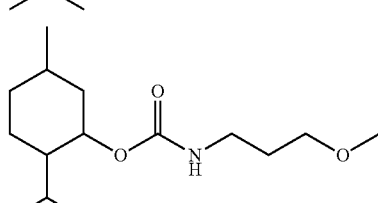

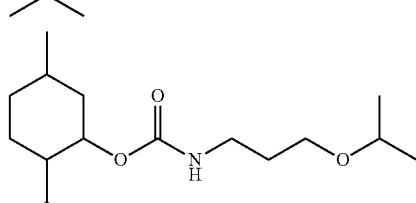

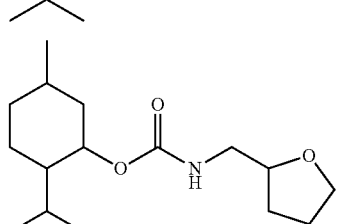

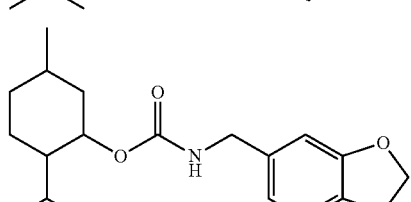

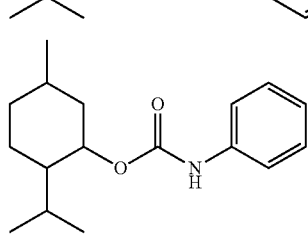

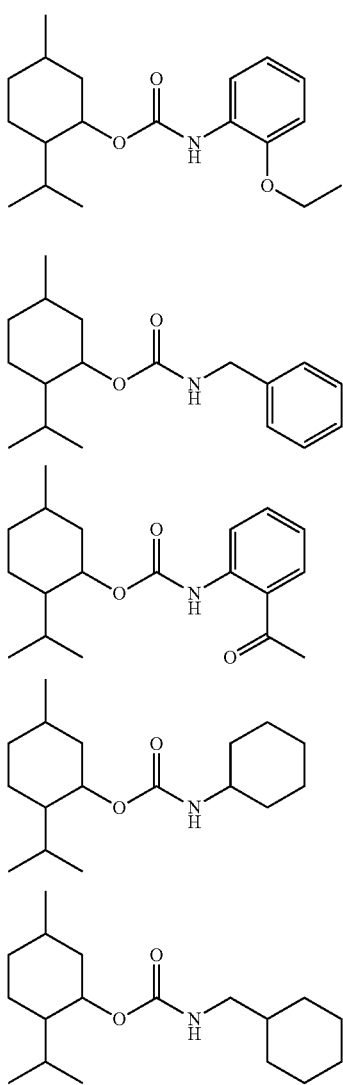
Due to their higher activity regarding the effects to be achieved in the context of the present invention, even more preferred compounds of formula (I) in accordance with the present invention are selected from the group consisting of:
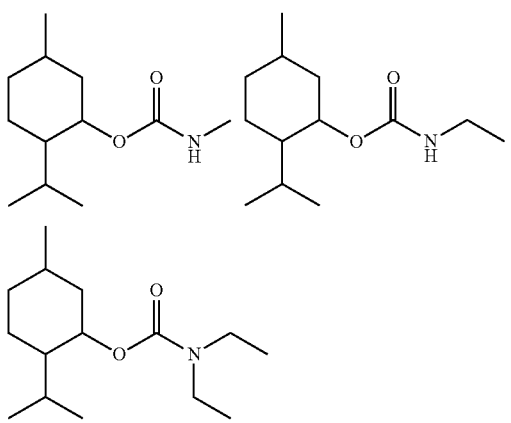
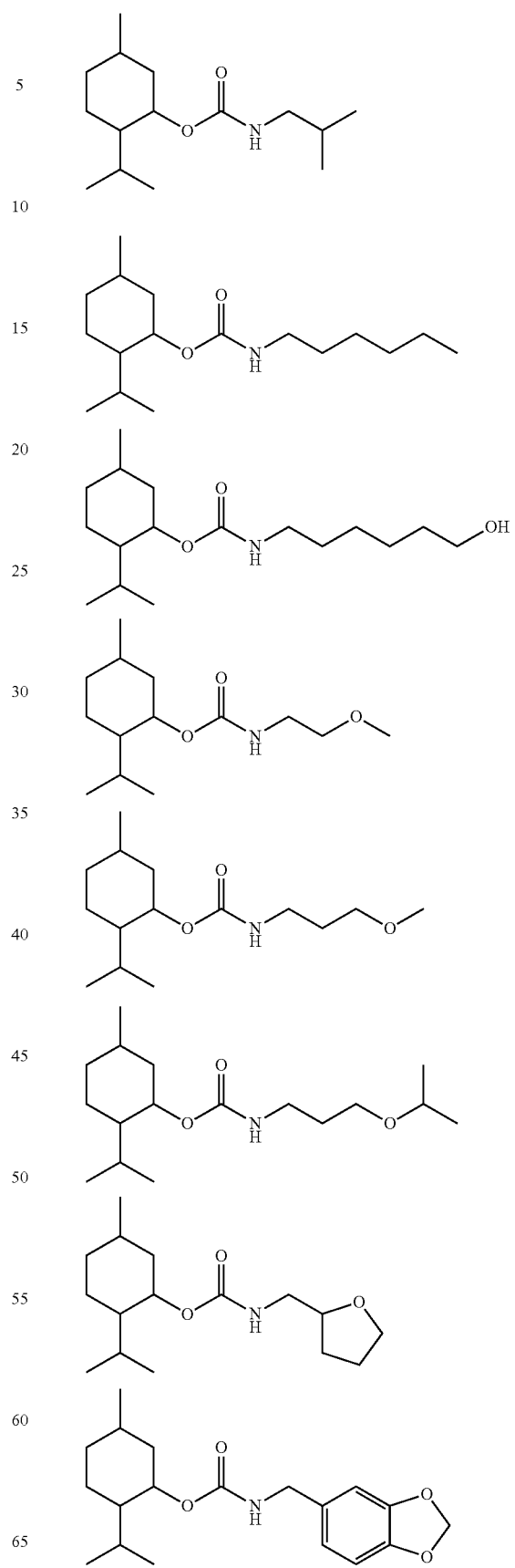

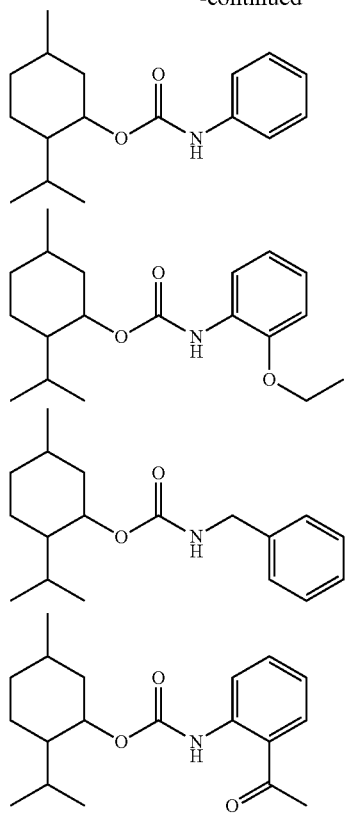

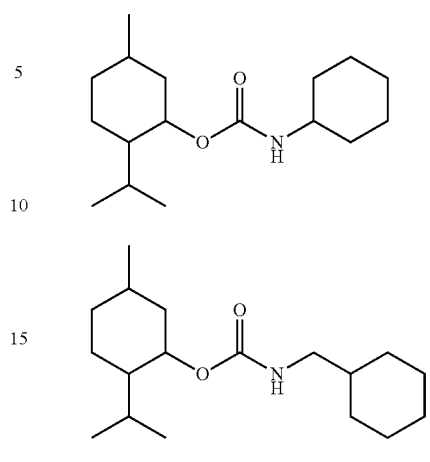

Of said compounds, those corresponding to formulae (Ia), (ent-Ia), (Ib) or (ent-Ib) or a respective racemic mixture thereof are particularly preferred.

Several compounds of formula (I), in particular the preferred compounds according to the present invention, are identified and referred to using an arbitrary internal reference-numbering system of the type "BIO", followed by a four-digit number.

Particularly preferred menthyl carbamates of formula (I) are the following:

| Reference-number | Chemical Name | Structure |
|---|---|---|
| BIO1151 | Ethyl-carbamic acid (1R,2S,5R)-2-isopropyl-5-methyl-cyclohexyl ester | 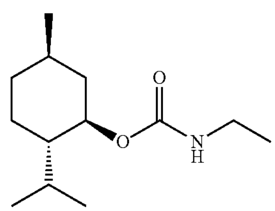 [SMILES: CCNC(=O)O[C@@H]1C[C@H](C)CC[C@H]1C(C)C] |
| BIO1378 | Ethyl-carbamic acid (1S,2R,5S)-2-ispropyl-5-methyl-cyclohexyl ester | 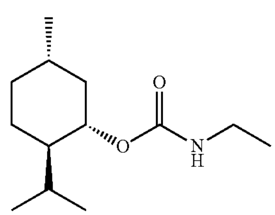 [SMILES: CCNC(=O)O[C@H]1C[C@@H](C)CC[C@@H]1C(C)C] |
| BIO1461 | Ethyl-carbamic acid (1S,2S,5R)-2-isopropyl-5-methyl-cyclohexyl ester | 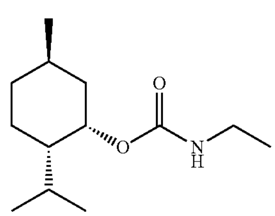 [SMILES: CCNC(=O)O[C@H]1C[C@H](C)CC[C@H]1C(C)C] |

| Reference-number | Chemical Name | Structure |
|---|---|---|
| BIO1155 | (3-Methoxy-propyl)-carbamic acid (1R,2S,5R)-2-isopropyl-5-methyl-cyclohexyl ester | 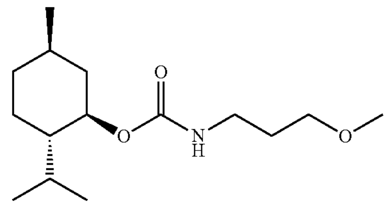 [SMILES: COCCCNC(=O)O[C@@H]1C[C@H](C)CC[C@H]1C(C)C] |
| BIO1339 | (3-Methoxy-propyl)-carbamic acid (1S,2R,5S)-2-isopropyl-5-methyl-cyclohexyl ester | 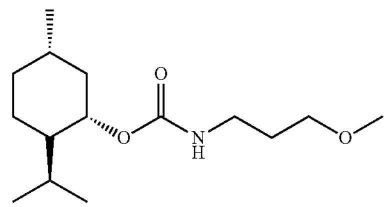 |
| BIO1460 | (3-Methoxy-propyl)-carbamic acid (1S,2S,5R)-2-isopropyl-5-methyl-cyclohexyl ester | 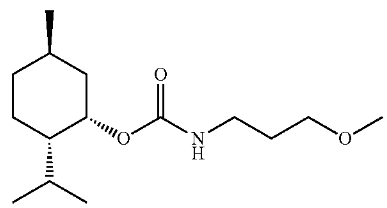 [SMILES: COCCCNC(=O)O[C@H]1C[C@H](C)CC[C@H]1C(C)C] |
| BIO1267 | Butyl-carbamic acid (1R,2S,5R)-2-isopropyl-5-methyl-cyclohexyl ester | 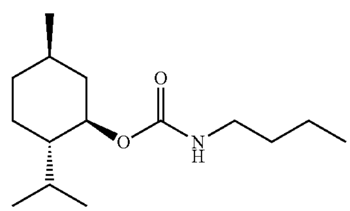 [SMILES: CCCCNC(=O)O[C@@H]1C[C@H](C)CC[C@H]1C(C)C] |
| BIO1268 | (3-Isopropoxy-propyl)-carbamic acid (1R,2S,5R)-2-isopropyl-5-methyl-cyclohexyl ester | 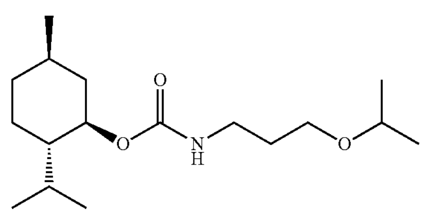 [SMILES: CC(C)OCCCNC(=O)O[C@@H]1C[C@H](C)CC[C@H]1C(C)C] |
| BIO1271 | Hexyl-carbamic acid (1R,2S,5R)-2-isopropyl-5-methyl-cyclohexyl ester | 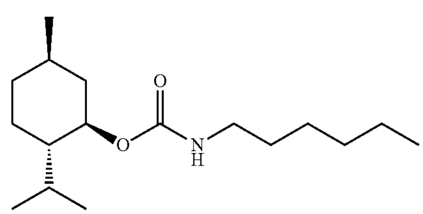 [SMILES: CCCCCCNC(=O)O[C@@H]1C[C@H](C)CC[C@H]1C(C)C] |
| BIO1159 | Isobutyl-carbamic acid (1R,2S,5R)-2-isopropyl-5-methyl-cyclohexyl ester | 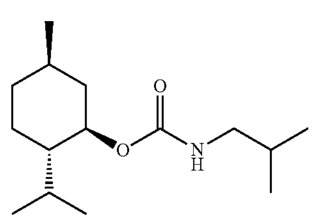 [SMILES: CC(C)CNC(=O)O[C@@H]1C[C@H](C)CC[C@H]1C(C)C] |

-continued

| Reference-number | Chemical Name | Structure |
|---|---|---|
| BIO1301 | Methyl-carbamic acid (1S,2R,5S)-2-isopropyl-5-methyl-cyclohexyl ester | 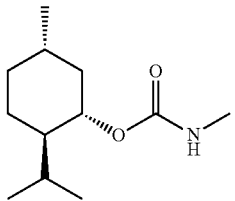 |
| BIO1571 | Benzo[1,3]dioxol-5-ylmethyl-carbamic acid (1R,2S,5R)-2-isopropyl-5-methyl-cyclohexyl ester | 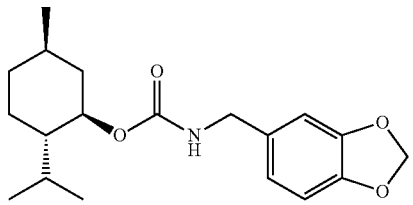 [SMILES: CC(C)[C@@H]1CC[C@@H](C)C[C@H]1OC(=O)NCc1ccc2c(c1)OCO2] |
| BIO1580 | Phenyl-carbamic acid (1R,2S,5R)-2-isopropyl-5-methyl-cyclohexyl ester | 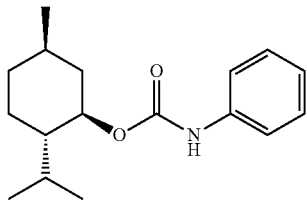 [SMILES: CC(C)[C@@H]1CC[C@@H](C)C[C@H]1OC(=O)Nc1ccccc1] |
| BIO1185 | Methyl-carbamic acid (1R,2S,5R)-2-isopropyl-5-methyl-cyclohexyl ester | 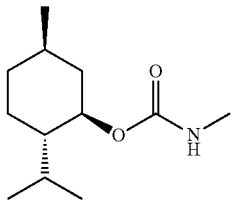 |
| BIO1336 | (2-Methoxy-ethyl)-carbamic acid (1R,2S,5R)-2-isopropyl-5-methyl-cyclohexyl ester | 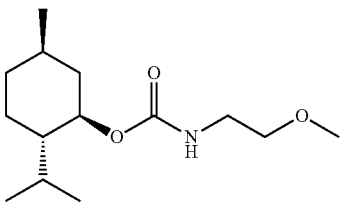 |
| BIO1662 | (6-Hydroxy-hexyl)-carbamic acid (1R,2S,5R)-2-isopropyl-5-methyl-cyclohexyl ester | 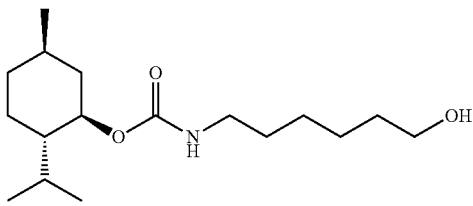 [SMILES: CC(C)[C@@H]1CC[C@@H](C)C[C@H]1OC(=O)NCCCCCCO] |
| BIO1699 | Cyclohexylmethyl-carbamic acid (1R,2S,5R)-2-isopropyl-5-methyl-cyclohexyl ester | 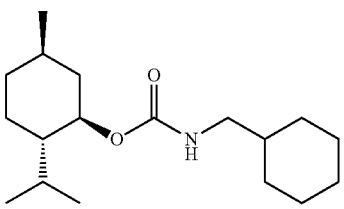 [SMILES: CC(C)[C@@H]1CC[C@@H](C)C[C@H]1OC(=O)NCC1CCCCC1] |

| Reference-number | Chemical Name | Structure |
|---|---|---|
| BIO1702 | (Tetrahydro-furan-2-ylmethyl)-carbamic acid (1R,2S,5R)-2-isopropyl-5-methyl-cyclohexyl ester | 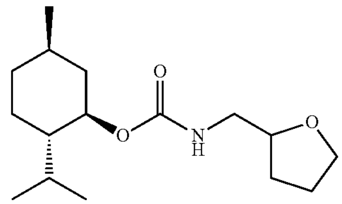 [SMILES: CC(C)[C@@H]1CC[C@@H](C)C[C@H]1OC(=O)NCC1CCCO1] |
| BIO1266 | Cyclohexyl-carbamic acid (1R,2S,5R)-2-isopropyl-5-methyl-cyclohexyl ester | 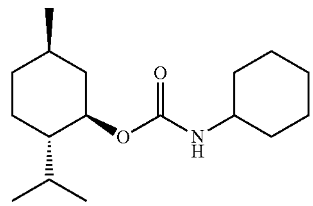 [SMILES: CC(C)[C@@H]1CC[C@@H](C)C[C@H]1OC(=O)NC1CCCCC1] |
| BIO1632 | (2-Ethoxy-phenyl)-carbamic acid (1R,2S,5R)-2-isopropyl-5-methyl-cyclohexyl ester | 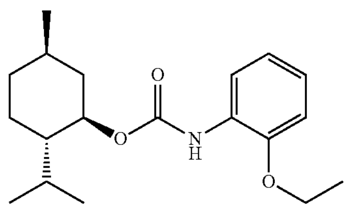 [SMILES: CCOc1ccccc1NC(=O)O[C@@H]1C[C@H](C)CC[C@H]1C(C)C] |
| BIO1633 | (2-Acetyl-phenyl)-carbamic acid (1R,2S,5R)-2-isopropyl-5-methyl-cyclohexyl ester | 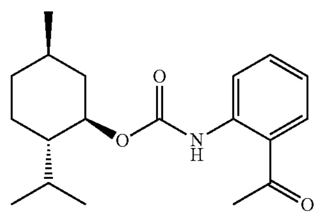 [SMILES: CC(=O)c1ccccc1NC(=O)O[C@@H]1C[C@H](C)CC[C@H]1C(C)C] |
| BIO1695 | Benzyl-carbamic acid (1R,2S,5R)-2-isopropyl-5-methyl-cyclohexyl ester | 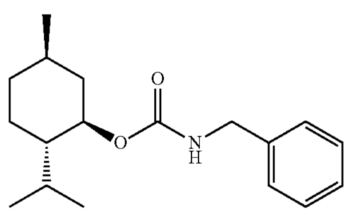 [SMILES: CC(C)[C@@H]1CC[C@@H](C)C[C@H]1OC(=O)NCc1ccccc1] |
| BIO1553 | Diethyl-carbamic acid (1R,2S,5R)-2-isopropyl-5-methyl-cyclohexyl ester | 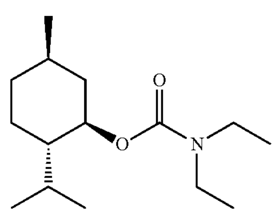 [SMILES: CCN(CC)C(=O)O[C@@H]1C[C@H](C)CC[C@H]1C(C)C] |

The (preferred) compounds of formula (I), in particular those explicitly listed above, were particularly active regarding the effects to be achieved in the context of the present invention.

The following compounds of formula (I) are particularly preferred since these were among the most active and effective compounds tested: BIO1151, BIO1571, BIO1266, BIO1460, BIO1461, BIO1580, BIO1632, BIO1633, BIO1695, BIO1699, BIO1155, BIO1553 and BIO1185.

The compounds of formula (I) of the present invention may generally be obtained by procedures well-known in chemical synthesis. For example, reaction of

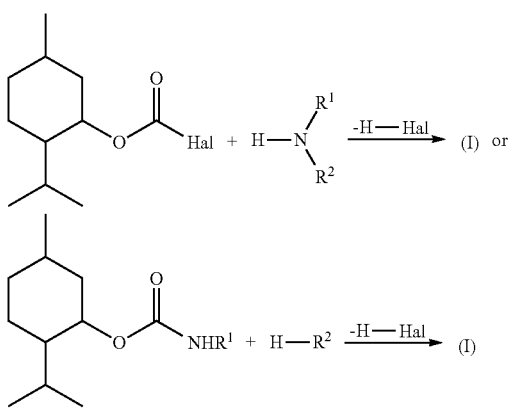

wherein
R[1] and R[2] denote a (preferred) radical as defined hereinabove, preferably R[1] denotes H, and Hal denotes a halide, preferably chloride or bromide.

In order to facilitate the dehydrohalogenation step and the formation of a compound of formula (I) it is preferred to carry out said reaction in the presence of a base, preferably a tertiary amine.

The preferred compounds of formula (I) wherein R[1] denotes H may preferably be obtained by reacting menthol with a corresponding isocyanate O=C=N—R[2], as illustrated in the following reaction scheme:

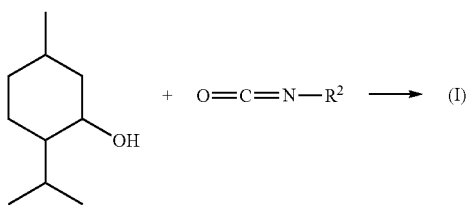

wherein R[2] denotes a (preferred) radical as defined hereinabove.

The present invention also relates to (preferably topical) cosmetic or pharmaceutical composition for lightening skin and/or hair, comprising
(a) one, two or more (preferably of the preferred) compounds of formula (I) as defined herein and/or a cosmetically or pharmaceutically acceptable salt thereof, preferably in an amount having a lightening effect on skin and/or hair, and
(b) one or more further active ingredients for skin and/or hair lightening suitable for cosmetic or pharmaceutical application which are not compounds of formula (I), preferably in an amount having a lightening effect on skin and/or hair.

Thus, in a (preferably topical) cosmetic or pharmaceutical composition according to the present invention for lightening skin and/or hair the amount of the one, two or more (preferably of the preferred) compounds of formula (I) as defined herein (component (a), above) alone and/or the amount of the one or more further active ingredients for skin and/or hair lightening (component (b), above) alone may not be sufficient to exhibit a lightening effect on skin and/or hair. However, the total amount, i.e. the sum, of components (a) and (b) in a composition according to the present invention is sufficient to exhibit a lightening effect on skin and/or hair.

As already indicated above, in preferred embodiments, the amount of the one, two or more (preferably of the preferred) compounds of formula (I) as defined herein (component (a), above) alone and/or the amount of the one or more further active ingredients for skin and/or hair lightening (component (b), above) alone in a composition according to the present invention are sufficient to exhibit a lightening effect on skin and/or hair.

A composition (preparation), preferably a topical composition, according to the present invention preferably contains one or more compounds of formula (I) (including all stereoisomers, enantiomers, diastereomers, cis/trans-isomers and epimers, without taking into account possible counterions) in a total amount of 0.001-30% by weight, more preferably 0.01-20% by weight, even more preferably 0.01-5% by weight, particularly preferably 0.05-3% by weight and most preferably 0.1-2% by weight, in each case based on the total weight of the preparation (composition).

In the context of the present invention an effective amount of (the preferred) compounds of formula (I) relates to a total amount of one, two or more (of the preferred) compounds of formula (I) having a lightening effect on human skin and/or human hair.

The compounds of formula (I) can easily be incorporated in these concentrations in common cosmetic or dermatological formulations (preparations) such as pump sprays, aerosol sprays, creams, ointments, tinctures, lotions and the like.

The cosmetic, dermatological or pharmaceutical preparations according to the invention can be produced by conventional processes known per se, such that one or more compounds of formula (I) are incorporated into (topical) cosmetic, dermatological or pharmaceutical products which can have a conventional composition and which in addition to the effects mentioned hereinbefore or hereinafter can also be used for the treatment, care and cleansing of the skin or hair.

For use, topical cosmetic, dermatological or pharmaceutical preparations according to the invention or for use according to the invention comprising formula (I) are generally applied to the skin and/or hair in an adequate amount in the conventional manner for topical cosmetic, dermatological or pharmaceutical products.

As stated above, no mention or suggestion is made in the prior art of a cosmetic or therapeutic use of compounds of formula (I) as skin and/or hair lightening agents or of compounds of formula (I) having depigmenting action.

One area of application in this regard is the therapeutic treatment of melanin-induced pigmentation disorders such as hyperpigmentations (e.g. scar hyperpigmentations, posttraumatic drug-induced hyperpigmentations, post-inflammatory hyperpigmentations induced by phototoxic reactions, ephelides).

A cosmetic or pharmaceutical, preferably topical, preparation according to the present invention preferably contains as component (b) one or more active ingredients for skin and/or hair lightening selected from the group consisting of:
kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, *papaya* extract, turmeric extract, mulberry extract, bengkoang extract, nutgrass extract, liquorice root extract or constituents concentrated or isolated therefrom, preferably glabridin or licochalcone A, artocarpus extract, extract of rumex and ramulus species, extracts of pine species (*pinus*), extracts of *vitis* species or stilbene derivatives isolated or concentrated therefrom, saxifrage extract, scutelleria extract and/or grape extract.

Preferred skin lighteners as component (b) are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, *papaya* extract, turmeric extract, nutgrass extract, licorice extract (containing glycyrrhizin), alpha-hydroxy-acids, 4-alkylresorcinols, 4-hydroxyanisole. These skin lighteners are preferred due to their very good activity, in particular in combination with one or more of the preferred or particularly preferred compounds of formula (I) according to the present invention. In addition, said preferred skin lighteners are readily available.

The skin and/or hair lightening activity of compounds of formula (I) is not based on tyrosinase inhibition.

A cosmetic or pharmaceutical, preferably topical, preparation according to the invention containing one or more active ingredients for skin and/or hair lightening selected from the above mentioned group of component (b) allows to achieve a more pronounced skin and/or hair lightening action which is, at least partly, based on synergistic effects.

Preparations according to the present invention including (a) one or more compounds of formula (I) and (b) one or more tyrosinase inhibitors have shown to exhibit particularly improved, in particular faster and/or stronger, activity, based on the modulation of two independent cellular mechanisms. In many cases a more than additive, often synergistic, lightening efficacy was observed.

Thus, in a preferred embodiment, preparations, preferably cosmetic preparations, according to the invention containing one or more compounds of formula (I) preferably comprise one or more active ingredients for skin and/or hair lightening which are tyrosinase inhibitors.

Preferred tyrosinase inhibitors are selected from the group consisting of kojic acid and skin and/or hair lightening resorcinol derivatives, preferably 4-alkylresorcinols, in particular 4-C3-C8-alkylresorcinols, and 4-(1-phenylethyl)1,3-dihydroxybenzene.

The total amount of component (b), i.e. the total amount of one or more further active ingredients for skin and/or hair lightening suitable for cosmetic or pharmaceutical application which are not compounds of formula (I), preferably selected from the aforementioned (preferred) group of further active ingredients for skin and/or hair lightening in the preparations according to the invention, preferably is in the range of from 0.01 to 30 wt. %, more preferably in the range of from 0.01 to 20 wt. %, particularly preferably in the range of from 0.01 to 5 wt. %, in each case based on the total weight of the preparation.

In the context of the present text, in case a substance has skin and/or hair lightening properties as well as one or more further properties selected from the group consisting of antioxidant, anti-inflammatory, anti-irritant and/or exfoliating properties, said substance is considered as skin and/or hair lightening active of component (b), in particular for quantitative assessments.

For use in the conventional manner for cosmetics and pharmaceuticals, the compounds of formula (I) are applied to the skin and/or the hair in an adequate quantity. Particular advantages are offered here by preparations, preferably cosmetic and dermatological preparations, which contain one or more compounds of formula (I) and additionally act as a sun protection means, thereby providing a preparation which protects the hair and/or the skin from ultraviolet radiation.

Particular advantageouse are cosmetic, dermatological and/or pharmaceutical preparations according to the invention which additionally include one or more sunscreen filters (UV absorbers, UV filters) and which thus act as both skin and/or lightening or age spot reducing agent and a sunscreen.

Preparations according to the invention in the cosmetics and pharmaceuticals area, which contain one or more compounds of formula (I), are advantageously combined with substances which absorb or reflect UV radiation, especially for cosmetic or skin-protecting purposes. Such preparations according to the present invention are particularly effective and beneficial in the lightening of skin and/or hair, in particular of skin.

Cosmetic preparations preferred according to the invention can also contain anti-inflammatory and/or redness and/or itch ameliorating active ingredients. The compounds mentioned in WO 2005/123101 are advantageously used as anti-inflammatory or redness and/or itch ameliorating active ingredients.

In preferred embodiments anti-irritants are used in the preparations according to the present invention. Such preparations according to the present invention are particularly effective and beneficial in the lightening of skin and/or hair, in particular of skin.

Anti-irritants in this connection can be all anti-inflammatory active ingredients or active ingredients to relieve reddening and itching which are suitable for or commonly used in cosmetic (e.g. dermatological) and/or therapeutic applications. All substances which reduce the amount of histamine and cytokines, especially interleukins, prostaglandins and/or leukotrienes in cells and tissue are preferred.

The melanin production is often stimulated as a result of an inflammation, a process called postinflammatory hyperpigmentation. Skin insults that result in inflammation/irritation can induce postinflammatory hyperpigmentation. Among such insults are acne lesions, ingrown hairs, scratches, insect bites, and surfactant damage. One of the most common forms of postinflammatory hyperpigmentations is tanning following exposure to sunlight as a response to UV damage to skin. Although in the latter case there may not be visible erythema, histologically, such exposed skin has elevated inflammatory/ irritant cell content, yielding a "subclinical" inflammatory/ irritant process. Thus to prevent inflammation/irritation of the skin is beneficial regarding the inhibition of melanogenesis in the skin.

Preferred antioxidants within the meaning of the present text are substances which lower the amount of free radicals in cells and/or tissue. Such preparations according to the present invention are particularly effective and beneficial in the lightening of skin and/or hair, in particular of skin.

Reactive oxygen species, such as superoxide and nitric oxide, generated in damaged skin (e.g. resulting from UV exposure) or released as by-products from inflammatory cells are known stimulators of melanogenesis in melanocytes. In such a case it is important to maintain the cellular redox by the suppression of reactive oxygen species, and to boost anti-oxidative defenses for the prevention of melanogenesis.

Thus, preferred preparations, preferably cosmetic preparations, according to the invention containing one or more compounds of formula (I) preferably additionally contain
one or more agents selected from the group of substances which absorb or reflect UV radiation, preferably for cosmetic purposes, in particular for skin- and/or hair-protecting purposes,
and/or
one or more agents selected from the group of anti-irritants and anti-inflammatory substances,
and/or
one or more agents selected from the group of antioxidants.

The total quantity of UV filter substances (UV absorbers) advantageously is in the range of from 0.01% to 40% by weight, preferably in the range of from 0.1% to 30% by weight, more preferably in the range of from 0.2 to 20% by weight, even more preferably in the range of from 0.5% to 15% by weight, in particular in the range of from 1.0 to 10.0% by weight, in each case based on the total weight of the preparation.

The total amount of anti-irritants (one or more compounds) and anti-inflammatory substances (one or more compounds) in the preparations according to the invention is preferably 0.01 to 20 wt. %, particularly preferably 0.03 to 10 wt. %, in particular 0.05 to 5 wt. %, based on the total weight of the preparation.

The total amount of antioxidants (one or more compounds) in the formulations according to the invention is preferably 0.01 to 20 wt. %, particularly preferably 0.05 to 10 wt. %, in particular 0.2 to 5 wt. %, based on the total weight of the formulation.

These preparations advantageously contain at least one UVA filter and/or at least one UVB filter and/or at least one inorganic pigment, so a light protection factor (sun protection factor, SPF) of 2 or higher (preferably of 5 or higher) is achieved.

Advantageous UV filters and inorganic light protection pigments are mentioned in WO 2005/123101. UV absorbers particularly suitable for combination are also mentioned in WO 2005/123101.

Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) such that the formulation according to the invention has a light protection factor of greater than or equal to 2 (preferably greater than or equal to 5). Such formulations according to the invention are particularly suitable for protecting the skin and hair.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Suitable UV filters are, for example, organic UV absorbers from the class comprising 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives, indole derivatives.

The compounds according to the invention or for use according to the invention having formula (I) are particularly preferably combined with water-soluble UV filters, in a preferred embodiment with phenylene bis-benzimidazyl tetrasulfonic acid disodium salt (Neo Heliopan®AP) and/or 2-phenylbenzimidazole sulfonic acid (Neo Heliopan® Hydro).

In addition, it is advantageous to combine compounds of formula (I) with active ingredients which penetrate into the skin and protect the skin cells from inside against sun light-induced damage such as skin ageing, skin inflammation and skin cancer. Respective ingredients, so called arylhydrocarbon receptor antagonists, are described in WO 2007/128723. Preferred is 2-benzylidene-5,6-dimethoxy-3,3-dimethylindan-1-one.

The UV filters cited below which can be used within the context of the present invention are preferred but naturally are not limiting.

UV filters which are preferably combined with one or more compounds of formula (I) in a preparation according to the present invention are selected from the group consisting of
p-aminobenzoic acid
p-aminobenzoic acid ethyl ester (25 mol) ethoxylated (INCI name: PEG-25 PABA)
p-dimethylaminobenzoic acid-2-ethylhexyl ester
p-aminobenzoic acid ethyl ester (2 mol) N-propoxylated
p-aminobenzoic acid glycerol ester
salicylic acid homomethyl ester (homosalates) (Neo Heliopan®HMS)
salicylic acid-2-ethylhexyl ester (Neo Heliopan®OS)
triethanolamine salicylate
4-isopropyl benzyl salicylate
anthranilic acid menthyl ester (Neo Heliopan®MA)
diisopropyl cinnamic acid ethyl ester
p-methoxycinnamic acid-2-ethylhexyl ester (Neo Heliopan®AV)
diisopropyl cinnamic acid methyl ester
p-methoxycinnamic acid isoamyl ester (Neo Heliopan®E 1000)
p-methoxycinnamic acid diethanolamine salt
p-methoxycinnamic acid isopropyl ester
2-phenylbenzimidazole sulfonic acid and salts (Neo Heliopan® Hydro)
3-(4'-trimethylammonium)benzylidene bornan-2-one methyl sulfate
beta-imidazole-4(5)-acrylic acid (urocanic acid)
3-(4'-sulfo)benzylidene bornan-2-one and salts
3-(4'-methyl benzylidene)-D,L-camphor (Neo Heliopan®MBC)
3-benzylidene-D,L-camphor N-[(2 and 4)-[2-(oxoborn-3-ylidene)methyl]benzyl]acrylamide polymer
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb®HEB)
benzylidene malonate polysiloxane (Parsol®SLX)
glyceryl ethylhexanoate dimethoxycinnamate
dipropylene glycol salicylate
tris(2-ethylhexyl)-4,4',4''-(1,3,5-triazine-2,4,6-triyltriimino) tribenzoate (=2,4,6-trianilino-(p-carbo-2'-ethylhexyl-1'-oxy)-1,3,5-triazine) (Uvinul®T150)

Broadband filters which are preferably combined with one or more compounds of formula (I) in a preparation according to the present invention are selected from the group consisting of
2-ethylhexyl-2-cyano-3,3-diphenyl acrylate (Neo Heliopan®303)
ethyl-2-cyano-3,3'-diphenyl acrylate
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
sodium hydroxymethoxybenzophenone sulfonate
disodium-2,2'-dihydroxy-4,4'-dimethoxy-5,5'-disulfobenzophenone
phenol, 2-(2H-benzotriazol-2-yl)-4-methyl-6-(2-methyl-3(1,3,3,3-tetramethyl-1-(trimethylsilyl)oxy)disiloxyanyl) propyl) (Mexoryl®XL)
2,2'-methylene bis-(6-(2H-benzotriazol-2-yl)-4-1,1,3,3-tetramethylbutyl)phenol) (Tinosorb®M)
2,4-bis-[4-(2-ethylhexyloxy)-2-hydroxyphenyl]-1,3,5-triazine
2,4-bis-[{(4-(2-ethylhexyloxy)-2-hydroxy}phenyl]-6-(4-methoxyphenyl)-1,3,5-triazine (Tinosorb®S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-(4-(2-methoxyethyl carbonyl)phenylamino]-1,3,5-triazine
2,4-bis-[{4-(3-(2-propyloxy)-2-hydroxypropyloxy)-2-hydroxy}phenyl]-6-[4-(2-ethylcarboxyl)phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2''-methylpropenyloxy)-2-hydroxy}phenyl]-6-(4-methoxyphenyl)-1,3,5-triazine
2,4-bis-[{4-(1',1',1',3',5',5',5'-heptamethylsiloxy-2''-methylpropyloxy)-2-hydroxy}phenyl]-6-(4-methoxyphenyl)-1,3,5-triazine UV-A filters filters which are preferably combined with one or more compounds of formula (I) in a preparation according to the present invention are selected from the group consisting of
4-isopropyl dibenzoyl methane
terephthalylidene dibornane sulfonic acid and salts (Mexoryl®SX)
4-t-butyl-4'-methoxydibenzoyl methane (avobenzone)/(Neo Heliopan® 357)
phenylene bis-benzimidazyl tetrasulfonic acid disodium salt (Neo Heliopan®AP)
2,2'-(1,4-phenylene)-bis-(1H-benzimidazole-4,6-disulfonic acid), monosodium salt
2-(4-diethylamino-2-hydroxybenzoyl)benzoic acid hexyl ester (Uvinul® A Plus)
indanylidene compounds in accordance with DE 100 55 940 (=WO 02/38537)

UV filters which are more preferably combined with one or more compounds of formula (I) in a preparation according to the present invention are selected from the group consisting of
p-aminobenzoic acid
3-(4'-trimethylammonium)benzylidene bornan-2-one methyl sulfate
salicylic acid homomethyl ester (Neo Heliopan®HMS)
2-hydroxy-4-methoxybenzophenone (Neo Heliopan®BB)
2-phenylbenzimidazole sulfonic acid (Neo Heliopan® Hydro)
terephthalylidene dibornane sulfonic acid and salts (Mexoryl®SX)
4-tert-butyl-4'-methoxydibenzoyl methane (Neo Heliopan®357)
3-(4'-sulfo)benzylidene bornan-2-one and salts
2-ethylhexyl-2-cyano-3,3-diphenyl acrylate (Neo Heliopan®303)
N-[(2 and 4)-[2-(oxoborn-3-ylidene)methyl]benzyl]acrylamide polymer
p-methoxycinnamic acid-2-ethylhexyl ester (Neo Heliopan®AV)
p-aminobenzoic acid ethyl ester (25 mol) ethoxylated (INCI name: PEG-25 PABA)
p-methoxycinnamic acid isoamyl ester (Neo Heliopan®E1000)
2,4,6-trianilino-(p-carbo-2'-ethylhexyl-1'-oxy)-1,3,5-triazine (Uvinul®T150)
phenol, 2-(2H-benzotriazol-2-yl)-4-methyl-6-(2-methyl-3(1,3,3,3-tetramethyl-1-(trimethylsilyl)oxy)disiloxyanyl) propyl) (Mexoryl®XL)
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb HEB)
3-(4'-methyl benzylidene)-D,L-camphor (Neo Heliopan®MBC)
3-benzylidene camphor
salicylic acid-2-ethylhexyl ester (Neo Heliopan®OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl)phenol) (Tinosorb®M)
phenylene bis-benzimidazyl tetrasulfonic acid disodium salt (Neo Heliopan®AP)
2,4-bis-[{(4-(2-ethylhexyloxy)-2-hydroxy}phenyl]-6-(4-methoxyphenyl)-1,3,5-triazine (Tinosorb®S)
benzylidene malonate polysiloxane (Parsol®SLX)
menthyl anthranilate (Neo Heliopan®MA)
2-(4-diethylamino-2-hydroxybenzoyl)benzoic acid hexyl ester (Uvinul® A Plus)
indanylidene compounds in accordance with DE 100 55 940 (=WO 02/38537).

Advantageous inorganic light protection pigments are finely dispersed metal oxides and metal salts which are also mentioned in WO 2005/123101. The total quantity of inorganic pigments, in particular hydrophobic inorganic micropigments in the finished cosmetic preparation according to the present invention is advantageously from 0.1 to 30% by weight, preferably 0.5 to 10.0% by weight, in each case based on the total weight of the preparation.

Furthermore, particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Steroidal anti-inflammatory substances of the corticosteroid type, such as e.g. hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004/047833, are preferred anti-itch ingredients in a composition according to the present invention. Alternatively, natural anti-inflammatory substances or substances to relieve reddening and itching can be used. Plant extracts, special highly active plant extract fractions and highly pure active substances isolated from plant extracts can be used. Particularly preferred are extracts, fractions and active substances from camomile, aloe vera, commiphora species, rubia species, echinacea species, willow, willowherb, oats, black and green tea, gingko, coffee, pepper, blackcurrant, tomato, vanilla, almonds, as well as pure substances such as inter alia bisabolol, apigenin-7-glucoside, boswellic acid, phytosterols, glycyrrhizinic acid, glabridin or licochalcone A.

In other preferred embodiments, a composition according to the present invention, comprises one or more actives providing a benefit for the skin, in particular skin irritation-reducing or skin-soothing agents, preferably selected from the group consisting of anti-inflammatory agents, compounds that alleviate itching and/or compounds that alleviate reddening which are suitable for cosmetic and/or dermatological applications, wherein the one or more actives are preferably selected from the groups consisting of:
- steroidal anti-inflammatory substances of the corticosteroid type, in particular hydrocortisone, hydrocortisone derivatives such as hydrocortisone 17-butyrate, dexamethasone, dexamethasone phosphate, methylprednisolone or cortisone; and/or
- natural or naturally occurring anti-inflammatory mixtures of substances or mixtures of substances that alleviate reddening and/or itching, in particular extracts or fractions from camomile, Aloe vera, Commiphora species, Rubia species, willow, willow-herb, oats, calendula, arnica, St John's wort, honeysuckle, rosemary, Passiflora incarnata, witch hazel, ginger or Echinacea; preferably selected from the group consisting of extracts or fractions from camomile, Aloe vera, oats, calendula, arnica, honeysuckle, rosemary, witch hazel, ginger or Echinacea, and/or
- pure substances, preferably alpha-bisabolol, apigenin, apigenin-7-glucoside, gingerols, shogaols, gingerdiols, dehydrogingerdiones, paradols, natural or naturally occurring avenanthramides, preferably tranilast, avenanthramide A, avenanthramide B, avenanthramide C, non-natural or non-naturally occurring avenanthramides, preferably dihydroavenanthramide D, dihydroavenanthramide E, avenanthramide D, avenanthramide E, avenanthramide F, boswellic acid, phytosterols, glycyrrhizin, glabridin and licochalcone A; preferably selected from the group consisting of alpha-bisabolol, gingerols, shogaols, gingerdiols, dehydrogingerdiones, paradols, natural avenanthramides, non-natural avenanthramides, preferably dihydroavenanthramide D (as described in WO 2004/047833), boswellic acid, phytosterols, glycyrrhizin, and licochalcone A; and/or Preferably a preparation according to the present invention comprises one or more actives selected from the groups consisting of:
- extracts or fractions from camomile, Aloe vera, oats, calendula, arnica, honeysuckle, rosemary, witch hazel, ginger or Echinacea; and/or
- alpha-bisabolol, gingerols, shogaols, gingerdiols, dehydrogingerdiones, paradols, natural avenanthramides, non-natural avenanthramides, preferably dihydroavenanthramide D, boswellic acid, phytosterols, glycyrrhizin, and licochalcone A; and/or
- urea, hyaluronic acid, allantoin, panthenol, lanolin, alpha-hydroxy acids (preferably citric acid, lactic acid), vitamin E and derivatives (preferably tocopherol, tocopheryl acetate).

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of Vanillosmopsis (in particular Vanillosmopsis erythropappa or Vanillosmopsis arborea). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide ($CO_2$), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

The formulations according to the invention can also contain (additional) antioxidants or preservatives. All antioxidants which are suitable or commonly used for cosmetic (e.g. dermatological) and/or therapeutic applications can be used as antioxidants or preservatives.

Antioxidants as part of a preparation according to the present invention are preferably chosen from the group comprising amino acids (e.g. glycine, histidine, tyrosine, tryptophane) and derivatives thereof, imidazoles (e.g. urocanic acid) and derivatives thereof, peptides such as D,L-carnosine, D-carnosine, L-carnosine and derivatives thereof (e.g. anserine), carnitine, creatine, matrikine peptides (e.g. lysyl-threonyl-threonyl-lysyl-serine) and palmitoylated pentapeptides, carotenoids, carotenes (e.g. alpha-carotene, beta-carotene, lycopene) and derivatives thereof, lipoic acid and derivatives thereof (e.g. dihydrolipoic acid), aurothioglucose, propyl thiouracil and other thiols (e.g. thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very small tolerated doses (e.g. pmol to µmol/kg), also (metal) chelators (e.g. alpha-hydroxy fatty acids, palmitic acid, phytic acid, lactoferrin, alpha-hydroxy acids (e.g. citric acid, lactic acid, malic acid), humic acid, bile acid, bile extracts, tannins, bilirubin, biliverdin, EDTA, EGTA and derivatives thereof), unsaturated fatty acids and derivatives thereof (e.g. gamma-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate, ascorbyl glucoside), tocopherols and derivatives (e.g. vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, e.g. alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids such as retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenium methionine), superoxide dismutase, stilbenes and derivatives thereof (e.g. stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, such as e.g. green tea, rooibos, honeybush, grape, rosemary, sage, melissa, thyme, lavender, olive, oats, cocoa, *ginkgo*, ginseng, liquorice, honeysuckle, *sophora*, pueraria, *pinus*, citrus, Phyllanthus emblica or St. John's wort, grape seeds, wheat germ, Phyllanthus emblica.

Also suitable are coenzymes, such as e.g. coenzyme Q10, plastoquinone, menaquinone, ubiquinols 1-10, ubiquinones 1-10 or derivatives of these substances.

If vitamin E and/or derivatives thereof are used as the antioxidant(s), it is advantageous to choose their concentrations from the range from 0.001 to 10 wt. %, based on the total weight of the formulation.

If vitamin A or vitamin A derivatives or carotenes or derivatives thereof are used as the antioxidant(s), it is advantageous to choose their concentrations from the range from 0.001 to 10 wt. %, based on the total weight of the formulation.

The present invention further relates to novel compounds of formula (I) or a cosmetically acceptable salt thereof:

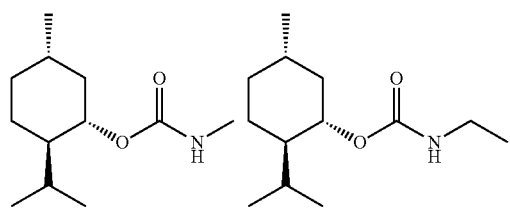

-continued

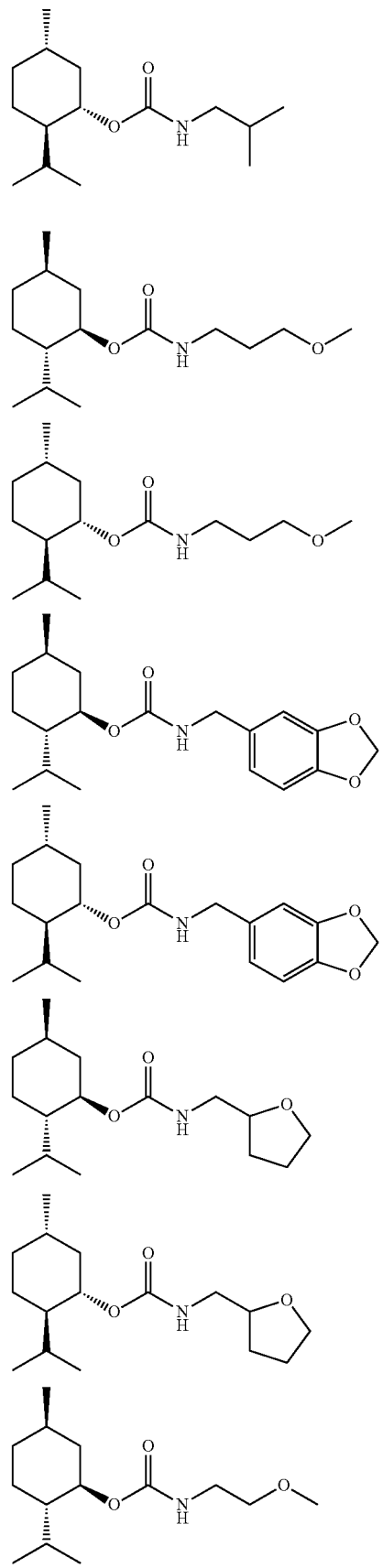

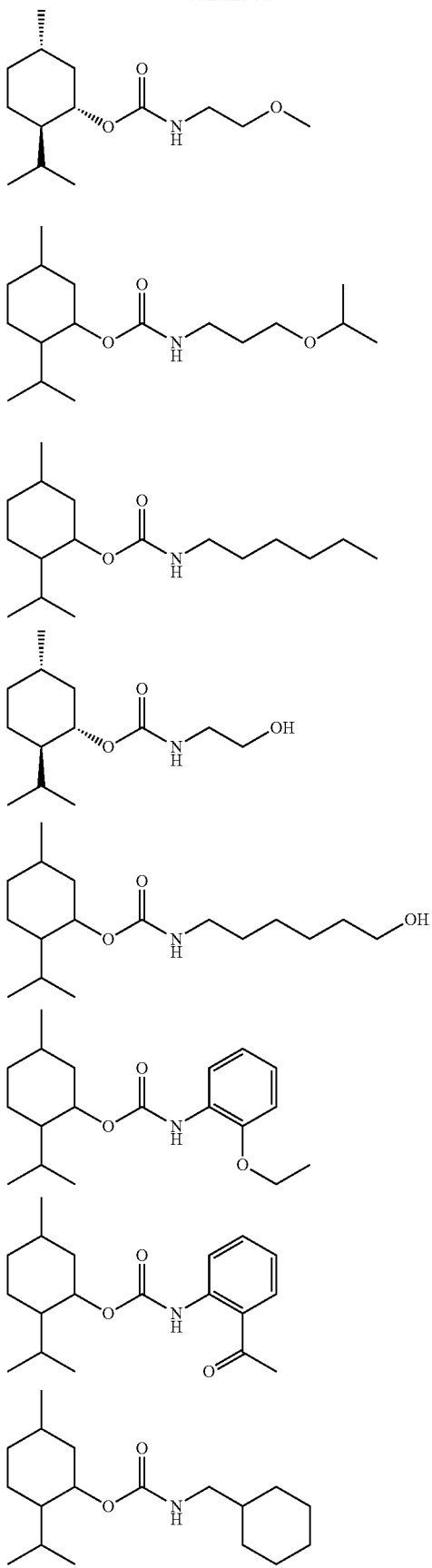

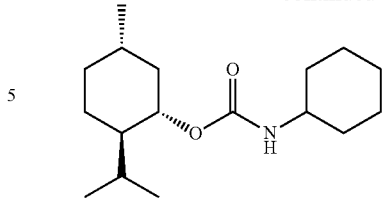

The (particularly) preferred compounds of formula (I) of the present invention are preferably used in the preferred compositions indicated hereinbefore or hereinafter.

The (particularly) preferred aspects and embodiments mentioned hereinbefore or hereinafter relating to compounds of formula (I) or compositions (preparations) comprising one or more compounds of formula (I) according to the present invention also apply to (particularly) preferred aspects and embodiments, uses and methods in accordance with the present invention.

The present invention further relates to a method for the cosmetic lightening skin and/or hair comprising the following step:

application, preferably topical application, of a cosmetically effective amount of a compound of formula (I) or a cosmetically acceptable salt of a compound of formula (I) or a mixture containing two or more of these compounds or the salts thereof as defined herein or of a cosmetic composition as defined herein.

A further aspect of the present invention is the use of a compound of formula (I) or a pharmaceutically acceptable salt of a compound of formula (I) or a mixture containing two or more of these compounds or the salts thereof as defined herein for the preparation of a pharmaceutical, preferably topical, composition for lightening skin and/or hair, in particular for the treatment of hyperpigmentation.

The present invention further relates to a compound of formula (I) or a pharmaceutically acceptable salt of a compound of formula (I) or a mixture containing two or more of these compounds or the salts thereof as defined herein as a drug, preferably as active for lightening skin and/or hair, in particular as active for the treatment of hyperpigmentation.

The present invention further relates to a pharmaceutical composition comprising a pharmaceutically active amount of one or more compounds of formula (I) as defined herein, preferably for lightening skin and/or hair, in particular for the treatment of hyperpigmentation.

Further, the present invention also relates to a method for lightening skin and/or hair, preferably for treating hyperpigmentation, comprising the following step:

application, preferably topical application, of a pharmaceutically effective amount of a compound of formula (I) or a pharmaceutically acceptable salt of a compound of formula (I) or a mixture containing two or more of these compounds or the salts thereof as defined herein or of a pharmaceutical composition as defined herein.

The present invention also relates to a cosmetic or therapeutic method for lightening human skin and/or hair, comprising the step of provision of one or more compounds of formula (I) or a cosmetically or pharmaceutically acceptable salt thereof, or of a cosmetic or pharmaceutical composition according to the present invention, application of the one or more compounds of formula (I) or of the composition to human skin and/or hair in an effective amount, said application preferably remaining for at least 10 minutes, more preferably for at least 30 minutes, most preferably for at least 60 minutes, on said skin and/or hair ("leave-on product").

Substances and auxiliaries which may additionally contain a preparation according to the invention containing one or more compounds of formula (I) are, for example: preservatives, in particular those described in US 2006/0089413, antimicrobial agents, such as e.g. antibacterial agents or agents to treat yeast and mold, in particular those described in WO 2005/123101, antiacne and sebum reducing agents, in particular those described in WO 2008/046791, compounds against ageing of the skin, in particular those described in WO 2005/123101 and US 2009/0232915, anticellulite agents, in particular those described in WO 2007/077541, anti-dandruff agents, in particular those described in WO 2008/046795, anti-irritants (ant-iinflammatory agents, irritation-preventing agents, irritation-inhibiting agents), in particular those described in WO 2007/042472 and US 2006/0089413, antioxidants, in particular those described in WO 2005/123101, carrier materials, in particular those described in WO 2005/123101, chelating agents, in particular those described in WO 2005/123101, deodorizing agents and antiperspirants, in particular those described in WO 2005/123101, moisture regulators (moisture-donating agents, moisturizing substance, moisture-retaining substances), in particular those described in WO 2005/123101, osmolytes, in particular those described in WO 2005/123101, compatible solutes, in particular those described in WO 01/76572 and WO 02/15868, proteins and protein hydrolysates, in particular those described in WO 2005/123101 and WO 2008/46676, skin-lightening agents, in particular those described in WO 2007/110415, cooling agents, in particular those described in WO 2005/123101, skin-cooling agents, in particular those described in WO 2005/123101, skin warming agents, in particular those described in WO 2005/123101, UV-absorbing agents, in particular those described in WO 2005/123101, UV filters, in particular those described in WO 2005/123101, benzylidene-beta-dicarbonyl compounds in accordance with WO 2005/107692 and alpha-benzoyl-cinnamic acid nitriles in accordance with WO 2006/015954, insect repellents, in particular those described in WO 2005/123101, plant parts, plant extracts, in particular those described in WO 2005/123101, vitamins, in particular those described in WO 2005/123101, emulsifiers, in particular those described in WO 2005/123101, gelling agents, in particular those described in WO 2005/123101, oils in particular those described in WO 2005/123101, waxes in particular those described in WO 2005/123101, fats in particular those described in WO 2005/123101, phospholipids, in particular those described in WO 2005/123101, saturated fatty acids and mono- or polyunsaturated fatty acids and α-hydroxy acids and polyhydroxy-fatty acids and esters of saturated and/or unsaturated branched and/or unbranched alkane carboxylic acids, in particular those described in WO 2005/123101, surface-active substances (surfactants), in particular those described in WO 2005/123101, skin repair agents comprising cholesterol and/or fatty acids and/or ceramides and/or pseudoceramides, in particular those described in WO 2006/053912, dyestuffs and colorants and pigments, in particular those described in WO 2005/123101, aroma chemicals and flavors and fragrances, in particular those described in S. Arctander, Perfume and Flavor Chemicals, private publishing house, Montclair, N.J., 1969 and Surburg, Panten, Common Fragrance and Flavor Materials, 5th Edition, Wiley-VCH, Weinheim 2006, preferably those explicitly mentioned in US 2008/0070825, alcohols and polyols, in particular those described in WO 2005/123101, organic solvents, in particular those described in WO 2005/123101, silicones and silicone oils and silicone derivatives in particular those described in WO 2008/046676, virucides, abrasives, astringents, antiseptic agents, antistatics, binders, buffers, cell stimulants, cleansing agents, care agents, depilatory agents, softeners, enzymes, essential oils, in particular those described in US 2008/0070825, fibres, film-forming agents (e.g. polyvinyl pyrrolidones, chitosan or chitosan derivatives), fixatives, foam-forming agents, foam stabilizers, substances for preventing foaming, foam boosters, gel-forming agents, hair growth activators, hair growth inhibitors, hair care agents, hair-setting agents, hair-straightening agents, hair-smoothening, bleaching agents, strengthening agents, stain-removing agents, optically brightening agents, impregnating agents, dirt-repellent agents, friction-reducing agents, lubricants, opacifying agents, plasticizing agents, covering agents, polish, gloss agents, polymers in particular those described in WO 2008/046676, powders, peptides, mono-, di- and oligosaccharides, re-oiling agents, abrading agents, skin-soothing agents, skin-cleansing agents, skin care agents, skin-healing agents, skin-protecting agents, skin-softening agents, skin-smoothing agents, nourishing agents, skin-warming agents, stabilizers, detergents, fabric conditioning agents, suspending agents, thickeners, yeast extracts, algae or microalgae extracts, animal extracts, liquefiers, color-protecting agents, and electrolytes.

In a preferred embodiment, a preparation according to the present invention comprises one or more compounds of formula (I) and one or more hair growth modulating actives, in particular one or more agents to stimulate hair growth.

Preferred agents to stimulate hair growth are selected from the group consisting of pyrimidine derivatives, in particular 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids, in particular caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters, in particular tocopheryl nicotinate, benzyl nicotinate and C1-C6 alkyl nicotinate, proteins, in particular the tripeptide Lys-Pro-Val, diphencypren, hormones, finasteride, dutasteride, flutamide, bicalutamide, pregnane derivatives, progesterone and its derivatives, cyproterone acetate, spironolactone and other diuretics, calcineurin inhibitors, in particular FK506 (Tacrolimus, Fujimycin) and its derivatives, Cyclosporin A and derivatives thereof, zinc and zinc salts, polyphenols, procyanidins, proanthocyanidins, phytosterols, in particular beta-sitosterol, biotin, eugenol, (±)-beta-citronellol, panthenol, glycogen, in particular from mussels, hydrolysates from rice, hydrolysates from wheat, and extracts from microorganisms, algae, microalgae or plants and plant parts, in particular of the genera dandelion (Leontodon or Taraxacum), *Orthosiphon, Vitex, Coffea, Paullinia, Theobroma, Asiasarum, Cucurbita* or *Styphnolobium, Serenoa repens* (saw palmetto), *Sophora flavescens, Pygeum africanum, Panicum miliaceum, Cimicifuga racemosa, Glycine max, Eugenia caryophyllata, Cotinus coggygria, Hibiscus rosa-sinensis, Camellia sinensis, Ilex paraguariensis*, licorice, grape, apple, barley and hops.

In another preferred embodiment, a preparation according to the present invention comprises one or more compounds of formula (I) and one or more agents to inhibit hair growth.

Preferred agents to inhibit hair growth are selected from the group consisting of activin, activin derivatives or activin agonists, ornithine decarboxylase inhibitors, in particular alphadifluoromethylomithine or pentacyclic triterpenes, in particular ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, and extracts from microorganisms, algae, microalgae or plants and plant parts, in particular of the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* and *Gymnema sylvestre*.

Also advantageous are preparations according to the invention which are administered orally, for example in the form of tablets (for example film tablets), coated tablets, capsules (for example gelatin capsules), granulates, juices, solutions emulsions, micro emulsions, sprays or products which can be consumed orally in another form, or in the form of food, which, because of the compound(s) contained therein of formula (I) bring about "beauty from inside".

The following osmolytes may be a component of a preparation according to the invention: sugar alcohols (myo-inositol, mannitol, sorbitol), quaternary amines such as taurine, choline, betaine, betaine glycine, ectoine, diglycerol phosphate, phosphorylcholine, glycerophosphorylcholines, amino acids such as glutamine, glycine, alanine, glutamate, aspartate or proline, phosphatidylcholine, phosphatidylinositol, inorganic phosphates, and polymers of the cited compounds such as proteins, peptides, polyamino acids and polyols. Preferred osmolytes, which may be a component of a preparation according to the invention, are diglycerol phosphate and/or ectoine.

Preferred cosmetics carrier materials, which may be a component of a preparation according to the invention, are solid or liquid at 25° C. and 1013 mbar (including highly viscous substances).

Preferred liquid carrier substances, which may be a component of a preparation according to the invention are selected from the group consisting of glycerol, 1,2-propylene glycol, 1,2-butylene glycol, 1,3-butylene glycol, 1,2-pentanediol, 1,2-hexanediol, 1,2-octanediol, 1,2-decanediol, ethanol, water and mixtures of two or more of said liquid carrier materials with water. Optionally, these preparations according to the invention may be produced using preservatives, solubilizers or antioxidants.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

Furthermore, the preparations according to the invention may be present in encapsulated form, these preferably being encapsulated with a solid covering material, which is preferably selected from starches, degraded or chemically or physically modified starches (in particular dextrins and maltodexterins), gelatins, gum arabic, agar-agar, ghatti gum, gellan gum, modified and non-modified celluloses, pullulan, curdlan, carrageenans, alginic acid, alginates, pectin, inulin, xanthan gum and mixtures of two or more of said substances.

The solid covering material is preferably selected from gelatin (preferred are pork, beef, chicken and/or fish gelatins and mixtures thereof, preferably comprising at least one gelatin with a bloom value of greater than or equal to 200, preferably with a bloom value of greater than or equal to 240), maltodextrin (preferably obtained from maize (corn), wheat, tapioca or potato, preferred maltodextrins have a DE value of 10-20), modified cellulose (for example cellulose ether), alginates (for example Na-alginate), carrageenan (beta-, iota-, lambda- and/or kappa carrageenan), gum arabic, curdlan and/or agar-agar. Gelatin is preferably used, in particular, because of its good availability in different bloom values. Particularly preferred, especially for oral use are seamless gelatin or alginate capsules, the covering of which dissolves very rapidly in the mouth or bursts when chewing. Production may take place, for example, as described in EP 0 389 700, U.S. Pat. No. 4,251,195, U.S. Pat. No. 6,214,376, WO 03/055587 or WO 2004/050069.

Preferred cosmetic, dermatological or pharmaceutical preparations according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, in particular as defined above, compared to rinse-off products, so that the skin and/or hair lightening action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, after-sun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

It is also advantageous to administer the compounds having formula (I) in encapsulated form, e.g. in gelatine, wax materials, liposomes or cellulose capsules.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99 wt. %, preferably 10 to 80 wt. %, based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99 wt. %, preferably 5 to 80 wt. %, based on the total weight of the preparation.

The one or more substances with a physiological cooling effect (cooling agents), which can be used in combination with one or more compounds of formula (I) according to the invention, are preferably selected here from the following list: menthol and menthol derivatives (for example L-menthol, D-menthol, racemic menthol, isomenthol, neoisomenthol, neomenthol) menthylethers (for example (1-menthoxy)-1,2-propandiol, (1-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy)acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or $N^\alpha$-(menthanecarbonyl)glycmethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005/049553, methanecarboxylic acid-N-(alkoxyalkyl) amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (1-(-)-isopulegol, I-(-)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840, further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2 033 688 A2).

The or the plurality of substances with a physiological cooling effect, which can be used in combination with one or more compounds of formula (I) according to the invention, are in particular preferably substances, which at least substantially cause a physiological cooling effect. Such preferred substances are: menthylethers (for example (1-menthoxy)-1,2-propandiol, (1-menthoxy)-2-methyl-1,2-propandiol), polar menthylesters (for example menthyllacetates, L-menthyl-L-lactate, L-menthyl-O-lactate, menthyl-(2-methoxy) acetate, menthyl-(2-methoxyethoxy)acetate, menthylpyroglutamate), menthylcarbonates (for example menthylpropyleneglycolcarbonate, menthylethyleneglycolcarbonate, menthylglycerolcarbonate), the semi-esters of menthols with a dicarboxylic acid or derivates thereof (for example mono-menthylsuccinate, mono-menthylglutarate, mono-menthylmalonate, O-menthyl succinic acid ester-N,N-(dimethyl)amide, O-menthyl succinic acid esteramide), not according to the invention, menthane carboxylic acid amides (for example menthane carboxylic acid-N-ethylamide [WS3], $N^\alpha$-(menthanecarbonyl)glycmethylester [WS5], menthane carboxylic acid-N-(4-cyanophenyl)amide, menthane carboxylic acid-N-(alkoxyalkyl)amides), menthone-derivatives (for example L-menthone glycerol ketal), 2,3-dimethyl-2-(2-propyl)-butyric acid derivates (for example 2,3-dimethyl-2-(2-propyl)-butyric acid-N-methylamide), pyrrolidone derivatives of cycloalkyldione derivatives (for example 3-methyl-2(1-pyrrolidinyl)-2-cyclopentene-1-one) or tetrahydropyrimidine-2-ones (for example iciline or related compounds, which are described in WO 2004/026840), 1R,2S,5R)—N-(4-Methoxyphenyl)-5-methyl-2-(1-isopropyl)cyclohexane-carboxamide [WS12], L-Menthyl N-methyl oxamate, L-menthyl N-ethyl oxamate (as described in EP 2 033 688).

The total quantity of substances having a physiological cooling effect (one or more compounds) in the preparations according to the invention preferably is in the range of from 0.05-5% by weight, more preferably in the range of from 0.1-3% by weight, in particular in the range of from 0.25-1.5% by weight, in each case based on the total weight of the cosmetic or pharmaceutical preparation.

Components which cause a hot, sharp, tingly or prickly feeling on the skin or on the mucous membranes, in particular flavours with a heat-producing effect and/or sharp tasting compounds (sharp substances) which may, apart from one or more compounds of formula (I), be a component of a preparation according to the invention, are mentioned in WO 2005/123101.

Further, combinations with compounds which reduce the hypersensitivity of skin nerves based on their action as TRPV1 antagonists, e.g. trans-4-tert-butyl cyclohexanol (as described in WO 2009/087242), or indirect modulators of TRPV1 by an activation of the μ-receptor, e.g. acetyl tetrapeptide-15, are preferred.

The following anti-cellulite actives may be a component of a preparation, preferably a cosmetic preparation, according to the invention: lipolysis stimulators like xanthines, in particular caffeine, extracts containing caffeine, or beta-adrenergic receptor agonists, for example synephrine and derivatives, and agents encouraging the activity of anti-cellulite agents, for example agents which stimulates and/or depolarises C nerve fibres such as capsaicin or vanillyl-nonylamid and derivatives thereof or extracts containing one or more of these substances like extracts obtainable from various species of the genus *Capsicum* (such as *Capsicum annum*), and compounds stimulating the microcirculation or draining, preferably selected from the group consisting of butcher's broom extract or its active component ruscogenin, horse chestnut extract or its active component escin, ivy extract and/or pineapple extract, (and) L-carnitine, coenzym A, isoflavonoides, soy extracts, conjugated linoleic acid (CLA). Preferably, anti-cellulite actives as a component of a preparation according to the invention are selected from the group consisting of caffeine, synephrine and/or L-carnitine.

Preferred preparations, preferably cosmetic preparations, according to the invention containing one or more compounds of formula (I) preferably additionally contain one or more active ingredients which prevent a breakdown of the connective tissue. Active ingredients are advantageous here which inhibit matrix-metallo-proteinases (MMPs). These enzymes are in a position to break down macromolecules of the extra-cellular matrix (ECM)/of the connective tissue, also including the collagens, proteolytically. In particular the matrix-metallo-proteinase-1 (MMP-1), matrix-metallo-proteinase-2 (MMP-2) and matrix-metallo-proteinase-9 (MMP-9) are responsible for the breakdown of the connective tissue of the skin. An inhibition of MMPs is possible, for example, by the addition of ursolic acid, retinyl palmitate, propyl gallate, precocenes, 6-hydroxy-7-methoxy-2,2-dimethyl-1 (2H)-benzopyran, 3,4-dihydro-6-hydroxy-7-methoxy-2,2-dimethyl-1(2H)-benzopyran. An addition of peptides, which inhibit MMPs, to preparations according to the invention, is also advantageous to inhibit MMPs. Proteins or glycoproteins from soya and hydrolysed proteins from rice, pea or lupine also inhibit MMPs and are therefore a suitable addition. A combination with a plant extract, which inhibits MMPs is also advantageous. To be mentioned here by way of example is an extract from shitake mushrooms. The combination with extracts from the leaves of the Rosaceae family, sub-family Rosoideae, is also advantageous. Quite particularly advantageous is the use of blackberry leaf extract, in particular as described in WO 2005/123101 A1.

MMP inhibitors to be preferably used in combination in the scope of the present invention are retinyl palmitate, propyl gallate, precocenes, 6-hydroxy-7-methoxy-2,2-dimethyl-1 (2H)-benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsulfonylfluoride, collhibin (company Pentapharm; INCI: hydrolysed rice protein), oenotherol (company Soliance; INCI: propylene glycol, aqua, Oenothera biennis root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and *lentinus edodes* extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and numerous further plant extracts, which are listed in WO 02/069992 (see table 1-12 there).

In order to counteract the breakdown of the connective tissue, the combination of active ingredients, which encourage the formation of collagen in the tissue (collagen stimulants), is furthermore advantageous in preferred cosmetic preparations according to the invention containing one or more compounds of formula (I). Individual substances frequently used to increase collagen synthesis are, for example, ingredients such as ascorbic acid and their derivatives, retinol and derivatives of retinol or plant extracts such as, for example, extracts of *aloe* and *centella* species. Moreover peptidic materials and their derivatives, such as, for example, carnitine, carnosine, creatine, matrikine peptides (e.g. lysyl-threonyl-threonyl-lysyl-serine) and further peptidic structures such as palmitoylated pentapeptides (for example matrixyl/company Sederma) or the oligopeptide with the trade name Vincipeptide (company Vincience/France) are also included in the frequently used active ingredients increasing collagen synthesis. Furthermore, compounds such as asiatic acid, madecassic acid, madecassoside, asiaticoside, extracts of *Centella asiatica*, niacinamide, astaxanthine, glucans, for example from yeast and oats, soya extracts and soya isoflavones such as genistein and daidzein, rutin, chrysin, morin, betel nut alkaloids, forskolin, betulinic acid, extracts of *Plantago* species, TGF-beta, extracts from *Ginkgo biloba*, glutamine and glycolic acid are also used as collagen synthesis stimulators. Particularly preferred here is the addition of a combination of *aloe vera* extract, raspberry extract and magnesium ascorbyl phosphate.

Formulations according to the invention, in particular dermatological formulations, can also advantageously contain dyes and/or coloured pigments, particularly if they are intended for use in the area of decorative cosmetics. The dyes and coloured pigments can be selected from the corresponding positive list in the German cosmetics ordinance or the EU list of cosmetic colorants. In most cases they are identical to the dyes approved for foodstuffs. Advantageous coloured pigments are for example titanium dioxide, mica, iron oxides (e.g. $Fe_2O_3Fe_3O_4$, $FeO(OH)$) and/or tin oxide. Advantageous dyes are for example carmine, Berlin blue, chromium oxide green, ultramarine blue and/or manganese violet.

If the topical formulations according to the invention are intended for use in the facial area, it is convenient to choose as the dye one or more substances from the following group: 2,4-dihydroxyazobenzol, 1-(2'-chloro-4'-nitro-1'-phenylazo)-2-hydroxynaphthalene, Ceres red, 2-(4-sulfo-1-naphthylazo)-1-naphthol-4-sulfonic acid, calcium salt of 2-hydroxy-1,2'-azonaphthalene-1'-sulfonic acid, calcium and barium salts of 1-(2-sulfo-4-methyl-1-phenylazo)-2-naphthyl carboxylic acid, calcium salt of 1-(2-sulfo-1-naphthylazo)-2-hydroxynaphthalene-3-carboxylic acid, aluminium salt of 1-(4-sulfo-1-phenylazo)-2-naphthol-6-sulfonic acid, aluminium salt of 1-(4-sulfo-1-naphthylazo)-2-naphthol-3,6-disulfonic acid, 1-(4-sulfo-1-naphthylazo)-2-naphthol-6,8-disulfonic acid, aluminium salt of 4-(4-sulfo-1-phenylazo)-1-(4-sulfophenyl)-5-hydroxypyrazolone-3-carboxylic acid, aluminium and zirconium salts of 4,5-dibromofluorescein, aluminium and zirconium salts of 2,4,5,7-tetrabromofluorescein, 3',4',5',6'-tetrachloro-2,4,5,7-tetrabromofluorescein and its aluminium salt, aluminium salt of 2,4,5,7-tetraiodofluorescein, aluminium salt of quinophthalone disulfonic acid, aluminium salt of indigo disulfonic acid, red and black iron oxide (Colour Index Number (CIN): 77491 (red) and 77499 (black)), iron oxide hydrate (CIN: 77492), manganese ammonium diphosphate and titanium dioxide.

Also advantageous are oil-soluble natural dyes, such as e.g. paprika extracts, β-carotene or cochineal.

Also advantageous within the meaning of the present invention are dermatological formulations containing pearlescent pigments. The types of pearlescent pigment listed below are particularly preferred:
1. Natural pearlescent pigments, such as e.g.
  "pearl essence" (guanine/hypoxanthine mixed crystals obtained from fish scales)
  and
  "mother of pearl" (ground mussel shells)
2. Monocrystalline pearlescent pigments such as e.g. bismuth oxychloride (BiOCl)
3. Layered substrate pigments: e.g. mica/metal oxide The basis for pearlescent pigments is formed for example by powdered pigments or castor oil dispersions of bismuth oxychloride and/or titanium dioxide and bismuth oxychloride and/or titanium dioxide on mica. The lustre pigment listed under CIN 77163, for example, is particularly advantageous.

The list of cited pearlescent pigments is naturally not intended to be limiting. Advantageous pearlescent pigments within the meaning of the present invention are obtainable in many ways known per se. For example, substrates other than mica can be coated with other metal oxides, such as e.g. silica and the like. SiO$_2$ particles coated with TiO$_2$ and Fe$_2$O$_3$ ("Ronaspheres"), for example, which are sold by Merck and are particularly suitable for the optical reduction of fine lines, are advantageous.

It can also be advantageous to dispense altogether with a substrate such as mica. Iron pearlescent pigments, which are produced without the use of mica, are particularly preferred. Such pigments are available from BASF, for example, under the trade name Sicopearl Copper 1000.

Particularly advantageous also are special effect pigments, which are available from Flora Tech under the trade name Metasomes Standard/Glitter in various colours (yellow, red, green, blue). Here the glitter particles are mixed with various auxiliary substances and dyes (for example the dyes with CIN 19140, 77007, 77289, 77491).

The dyes and pigments can be present both individually and mixed together and coated with one another, wherein different colour effects can generally be obtained by means of varying coating thicknesses. The total amount of dyes and colouring pigments is advantageously chosen from the range from e.g. 0.1 wt. % to 30 wt. %, preferably 0.5 to 15 wt. %, in particular 1.0 to 10 wt. %, based in each case on the total weight of the (cosmetic) formulations.

A combination with (metal)-chelating agents may also be advantageous in some preparations. (Metal)-chelating agents to be preferably used are the compounds mentioned in WO 2005/123101.

The one or more compounds of formula (I) may advantageously be used, in particular, in cosmetic and dermatological preparations in combination with insect repellents such as, for example, DEET, IR 3225, Dragorepel™ (Symrise GmbH & Co. KG).

The one or more compounds of formula (I) can advantageously be used in particular in cosmetic and dermatological preparations in combination with hair care agents and anti-dandruff active ingredients (for example climbazole, ketoconazole, piroctone oleamine, zinc-pyrithione).

The compounds of formula (I) can also advantageously be used in numerous cases in combination with one or more preservatives in preparations according to the invention. The preservatives mentioned in WO 2005/123101 are preferably selected here.

Preparations according to the invention, apart from one or more compounds of formula (I), may also contain plant extracts which can be used for cosmetic purposes. The plant extracts are preferably selected from the table of listed substances beginning on page 44 of the third edition of the handbook on the contents declaration of cosmetic agents, published by the Industrieverband Körperpflegemittel and Waschmittel e.V. (IKW), Frankfurt. The extracts mentioned in WO 2005/123101 are also particularly advantageous.

In preferred embodiments, a composition according to the present invention, comprises one or more cosmetically acceptable carriers selected from the group consisting of
(i) (alkane) diols having 3 to 10 carbon atoms, preferably selected from the group consisting of 1,2-propylene glycol, 2-methylpropane-1,3-diol, 1,2-butylene glycol, 1,3-butanediol, 1,2-pentanediol, 1,3-pentanediol, 1,5-pentanediol, 2,4-pentanediol, 2-methylpentane-2,4-diol, 1,2-hexanediol, 1,6-hexanediol, 1,2-octanediol, dipropylene glycol, preferably 1,2-butylene glycol, 1,2-pentanediol and/or dipropylene glycol, and/or
(ii-1) esters having 6 to 36 carbon atoms, preferably monoesters, diesters or triesters, preferably selected from the group consisting of diethyl phthalate, diethylhexyl 2,6-naphthalate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 3,5,5-trimethylhexyl 3,5,5-trimethylhexanoate, 2-ethylhexyl isononanoate, 2-ethylhexyl 3,5,5-trimethylhexanoate, 2-ethylhexyl 2-ethylhexanoate, 2-ethylhexyl palmitate, 2-ethylhexyl laurate, 2-hexyldecyl stearate, cetearyl ethylhexanoate, stearyl heptanoate, stearyl caprylate, 2-octyldodecyl palmitate, oleyl oleate, oleyl erucate, erucyl oleate, erucyl erucate, 2-ethylhexyl isostearate, isotridecyl isononanoate, 2-ethylhexyl cocoate, C$_{12-15}$-alkyl benzoates, cetyl palmitate, triethyl citrate, triacetin (triacetyl citrate), benzyl benzoate, benzyl acetate, vegetable oils (preferably olive oil, sunflower oil, soya oil, groundnut oil, rapeseed oil, almond oil, palm oil, coconut oil, palm kernel oil) and triglycerides, in particular glyceryl stearate, glyceryl triisononanoate, glyceryl laurate or triglycerides with identical or different C6 to C10 fatty acid radicals (so-called medium-chain triglycerides, in particular caprylic/capric triglyceride, like glyceryl tricaprylate, glyceryl tricaprate), and/or
(ii-2) branched and unbranched alkyl or alkenyl alkohols, preferably selected from the group consisting of decanol, decenol, octanol, octenol, dodecanol, dodecenol, octadienol, decadienol, dodecadienol, oleyl alcohol, ricinoleyl alcohol, erucyl alcohol, stearyl alcohol, isostearyl alcohol, cetyl alcohol, lauryl alcohol, myristyl alcohol, arachidyl alcohol, linoleyl alcohol, linolenyl alcohol, hexyldecanol, octyldodecanol (in particular 2-octyl-1-dodecanol) and cetearyl alcohol and behenyl alcohol, and/or
(ii-3) branched and unbranched hydrocarbons and waxes, cyclic or linear silicone oils and dialkyl ethers having 6 to 24 carbon atoms, preferably selected from the group consisting of jojoba oil, isoeicosane, dicaprylyl ether, mineral oil, petrolatum, squalane, squalene, cyclomethicone, decamethylcyclopentasiloxane, undecamethylcyclotrisiloxane, polydimethylsiloxane and poly(methyl-phenyl siloxane.

In other preferred embodiments, a composition according to the present invention, comprises one or more skin care agents, preferably skin moisture retention regulators or skin repair agents, preferably selected from the group consisting of sodium lactate, urea and derivatives, glycerol, 1,2-pentanediol, collagen, elastin or hyaluronic acid, diacyl adipates, petrolatum, urocanic acid, lecithin, allantoin, panthenol, phytantriol, lycopene, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, cholesterol, phytosterols, chitosan, chondroitin sulfate, lanolin, lanolin esters, amino acids, vitamin E and derivatives (preferably tocopherol, tocopheryl acetate), alpha-hydroxy acids (preferably citric acid, lactic acid, malic acid) and derivatives thereof, mono-, di- and oligosaccharides, preferably glucose, galactose, fructose, mannose, laevulose and lactose, polysugars, such as β-glucans, in particular 1,3-1,4-β-glucan from oats, alpha-hydroxy-fatty acids, triterpenic acids, such as betulic acid or ursolic acid, and algae extracts, preferably selected from the group consisting of glycerol, 1,2-pentanediol, urea, hyaluronic acid, allantoin, panthenol, lanolin, alpha-hydroxy acids (preferably citric acid, lactic acid), vitamin E and derivatives (preferably tocopherol, tocopheryl acetate).

Formulations according to the invention can also contain preservatives. The following can be used as preservatives: all antioxidants which are suitable or commonly used for cosmetic (e.g. dermatological) and/or therapeutic applications, traditional preservatives (e.g. formaldehyde, glutardialdehyde, parabens (e.g. methyl, ethyl, propyl and butyl paraben), dibromodicyanobutane, imidazolidinyl ureas ("Germall"), isothiazolinones ("Kathon"), methyl chlorothiazolidine, methyl thiazolidine, organic acids (e.g. benzoic acid, sorbic acid, salicylic acid) and salts and esters thereof, propionic acid and formic acid and salts thereof, glycols (e.g. propylene glycol, 1,2-dihydroxyalkanes), plant-based preservative aids such as e.g. lantadin A, caryophyllene, hesperidin, diosmin, phellandrene, pigenin, quercetin, hypericin, aucubin, diosgenin, plumbagin, corlilagin and the like.

The cosmetic or therapeutic, preferably topical, preparations according to the invention also preferably contain antimicrobial active ingredients. Suitable antimicrobial actives are:

Aryl- or aryloxy-substituted, unbranched or monoalkyl- and polyalkyl-branched saturated or mono- to pentaunsaturated (up to five double or triple bonds, also mixed ene/ine compounds) fatty alcohols, fatty aldehydes and fatty acids having chain lengths of $C_2$ to $C_{40}$.

Aryl- or aryloxy-substituted, unbranched or monoalkyl- and polyalkyl-branched saturated or mono- to pentaunsaturated (up to five double or triple bonds, also mixed ene/ine compounds) alkane diols, dialdehydes and dicarboxylic acids having chain lengths of $C_2$ to $C_{40}$, particularly preferably chain lengths of $C_4$ to $C_{12}$.

Mono- and oligoglycerides (up to 4 glycerol units) of aryl- or aryloxy-substituted unbranched or monoalkyl- and polyalkyl-branched saturated or mono- to pentaunsaturated (up to five double or triple bonds, also mixed ene/ine compounds) fatty alcohols (mono- and oligoglycerol monoalkyl ethers), fatty acids (mono- and oligoglycerol monoalkyl esters), alkanediols (mono- and oligoglycerol monoalkyl ethers; bis(mono-/oligoglyceryl)alkyl diethers) and dicarboxylic acids (mono- and oligoglycerol monoalkyl esters; bis(mono-/oligoglyceryl) alkyl diesters) having chain lengths of $C_2$ to $C_{40}$.

Fatty acid esters of unbranched or monoalkyl- and polyalkyl-branched saturated or mono- to pentaunsaturated (up to five double or triple bonds, also mixed ene/ine compounds), optionally also aryl- or aryloxy-substituted, carboxylic acids having chain lengths of $C_2$ to $C_{40}$ with unbranched or monoalkyl- and polyalkyl-branched saturated or mono- to pentaunsaturated (up to five double or triple bonds, also mixed ene/ine compounds), optionally also aryl- or aryloxy-substituted, monohydric to hexahydric fatty alcohols having chain lengths of $C_2$ to $C_{40}$.

Plant and animal fatty acid cuts, containing unbranched or monoalkyl- and polyalkyl-branched saturated or mono- to pentaunsaturated (up to five double or triple bonds, also mixed ene/ine compounds) fatty alcohols, fatty aldehydes and fatty acids having chain lengths of $C_2$ to $C_{40}$ (e.g. coconut fatty acids, palm kernel fatty acids, wool wax acids).

Mono- and oligoglycerides of lanolin, of lanolin alcohols and lanolic acids (e.g. glyceryl lanolate, neocerite), glycyrrhetic acid and derivatives (e.g. glycyrrhetinyl stearate), natural and synthetic cardenolides (e.g. digitoxin, dogoxin, digoxygenin, gitoxygenin, strophanthin and strophanthidin), natural and synthetic bufadienolides (e.g. scillaren A, scillarenin and bufotalin), sapogenins and steroid sapogenins (e.g. amyrins, oleanolic acid, digitonin, gitogenin, tigogenin and diosgenin), steroid alkaloids of plant and animal origin (e.g. tomatidin, solanin, solanidin, conessin, batrachotoxin and homobatrachotoxin).

Mono- and polyhalogenated nitriles, dinitriles, trinitriles or tetranitriles.

Mono- and oligohydroxy fatty acids having chain lengths of $C_2$ to $C_{24}$ (e.g. lactic acid, 2-hydroxypalmitic acid), oligomers and/or polymers thereof and plant and animal raw materials containing these.

Acyclic terpenes: terpene hydrocarbons (e.g. ocimene, myrcene), terpene alcohols (e.g. geraniol, linalool, citronellol), terpene aldehydes and ketones (e.g. citral, pseudoionone, beta-ionone); monocyclic terpenes: terpene hydrocarbons (e.g. terpinene, terpinolene, limonene), terpene alcohols (e.g. terpineol, thymol, menthol), terpene ketones (e.g. pulegone, carvone); bicyclic terpenes: terpene hydrocarbons (e.g. carane, pinane, bornane), terpene alcohols (e.g. borneol, isoborneol), terpene ketones (e.g. camphor); sesquiterpenes: acyclic sesquiterpenes (e.g. farnesol, nerolidol), monocyclic sesquiterpenes (e.g. bisabolol), bicyclic sesquiterpenes (e.g. cadinene, selinene, vetivazulene, guajazulene), tricyclic sesquiterpenes (e.g. santalene), diterpenes (e.g. phytol), tricyclic diterpenes (e.g. abietic acid), triterpenes (squalenoids; e.g. squalene), tetraterpenes.

Ethoxylated, propoxylated or mixed ethoxylated/propoxylated cosmetic fatty alcohols, fatty acids and fatty acid esters having chain lengths of $C_2$ to $C_{40}$ with 1 to 150 E/O and/or P/O units.

Antimicrobial peptides and proteins having an amino acid value from 4 to 200, e.g. Skin Antimicrobial Peptides (SAPs), Lingual Antimicrobial Peptides (LAPs), human beta-defensins (in particular h-BD1 and h-BD2), lactoferrins and hydrolysates thereof and peptides obtained therefrom, Bactericidal/Permeability Increasing Proteins [BPIs], Cationic Microbial Proteins [CAPs], lysozyme.

Very suitable carbohydrates or "carbohydrate derivatives", which in the interests of brevity can also be included under the term "carbohydrates", are compounds containing sugars and substituted sugars or sugar groups. The sugars include in particular also the deoxy and dideoxy forms, N-acetyl galactosamine-, N-acetyl glucosamine- and sialic acid-substituted derivatives as well as sugar esters and ethers. Preference is given to a) monosaccharides, including in particular pentoses and hexoses,
b) disaccharides, including in particular sucrose, maltose, lactobiose,
c) oligosaccharides, including in particular the tri- and tetrasaccharides, and
d) polysaccharides, including in particular starch, glycogen, cellulose, dextran, tunicin, inulin, chitin, in particular chitosans, chitin hydrolysates, alginic acid and alginates, plant gums, body mucosa, pectins, mannans, galactans, xylans, araban, polyoses, chondroitin sulfates, heparin, hyaluronic acid and glycosaminoglycanes, hemicelluloses, substituted cellulose and substituted starch, in particular the hydroxyalkyl-substituted polysaccharides in each case.

Amylose, amylopectin, xanthan, alpha-, beta- and gamma-dextrin are particularly suitable. The polysaccharides can consist of e.g. 4 to 1,000,000, in particular 10 to 100,000, monosaccharides. Chain lengths are preferably chosen in each case which ensure that the active ingredient is soluble in or can be incorporated into the particular formulation.

Sphingolipids such as sphingosine; N-monoalkylated sphingosines; N,N-dialkylated sphingosines; sphingosine-1-phosphate; sphingosine-1-sulfate; psychosine (sphingosine-beta-D-galactopyranoside); sphingosyl phosphoryl cholin; lysosulfatides (sphingosyl galactosyl sulfate; lysocerebroside sulfate); lecithin; sphingomyelin; sphinganine.

So-called "natural" antibacterial active ingredients can also be used, most of which are essential oils. Typical oils having an antibacterial action are, for example, oils of aniseed, lemon, orange, rosemary, wintergreen, clove, thyme, lavender, hops, citronella, wheat, lemongrass, cedarwood, cinnamon, geranium, sandalwood, violet, eucalyptus, peppermint, gum benzoin, basil, fennel, menthol and *Ocmea origanum, Hydastis carradensis, Berberidaceae daceae, Ratanhiae* or *Curcuma longa.*

Important substances having an antimicrobial action which can be found in essential oils are for example anethol, catechol, camphene, carvacrol, eugenol, eucalyptol, ferulic acid, farnesol, hinokitiol, tropolone, limonene, menthol, methyl salicylate, thymol, terpineol, verbenone, berberine, curcumin, caryophyllene oxide, nerolodol, geraniol.

Mixtures of the cited active systems or active ingredients and active ingredient combinations containing these active ingredients can also be used.

The amount of antimicrobial active ingredients in the formulations is preferably 0.01 to 20 wt. %, based on the total weight of the formulations, particularly preferably 0.05 to 10 wt. %.

In another preferred embodiment a topical, preferably cosmetic, preparation according to the present invention additionally comprises one or more fragrance materials, preferably having a Clog P value of at least 3, preferably of at least 4, more preferably of at least 5. Suitable fragrance materials are mentioned in S. Arctander, Perfume and Flavor Chemicals, Vol. I and II, Montclair, N.J., 1969, self-published or H. Surburg and J. Panten, Common Fragrance and Flavor Materials, 5th. Ed., Wiley-VCH, Weinheim 2006, particularly those explicitly mentioned in US 2008/0070825.

Preparations according to the present invention advantageously comprise a total amount of 0.1 to 5 wt. %, preferably 0.2 to 4 wt. %, more preferably 0.25 to 3 wt. %, even more preferably 0.3-2.5 wt. %, of the one or more (preferred) fragrance materials, in each case based on the total weight of the preparation.

In a further preferred embodiment a preparation, preferably a cosmetic leave-on product, according to the present invention additionally comprises one or more of fragrance materials having a boiling point of 250° C. or greater (at 1013 mbar). The total amount of fragrance materials having a boiling point of 250° C. or greater (at 1013 mbar) preferably is at least 10 wt. %, more preferably at least 20 wt. %, based on the total amount of fragrance materials present in a preparation according to the present invention.

More preferably the fragrance materials, preferably having a boiling point of 250° C. or greater at 1013 mbar, are selected from (here in some cases the normal industrial product names and registered trademarks of various firms are given): alpha-amyl cinnamic aldehyde, alpha-hexyl cinnamic aldehyde, 2-phenoxyethylisobutyrate (Phenirat), methyl dihydrojasmonate [preferably with a content of cis-isomers of >60 by weight (Hedione, Hedione HC)], 4,6,6,7,8,8-hexamethyl-1,3,4,6,7,8-hexahydrocyclopenta[g]benzopyran (Galaxolide), benzylsalicylate, 2-methyl-3-(4-tert-butyl-phenyl)propanal (Lilial), 4,7-methano-3a,4,5,6,7,7a-hexahydro-5-indenyl acetate and/or 4,7-methano-3a,4,5,6,7,7a-hexahydro-6-indenyl acetate (Herbaflorat), styrallyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthaline (Iso E Super), hexylsalicylate, 4-tert.-butylcyclohexyl acetate (Oryclon), 2-tert.-butylcyclohexyl acetate (Agrumex HC), alpha-ionone (4-(2,2,6-trimethyl-2-cyclohexen-1-yl)-3-buten-2-one), 4-(4-hydroxy-4-methylpentyl)-3-cyclohexene carboxaldehyde (Lyral), (E)- and/or (Z)-3-methylcyclopentadec-5-enone (Muscenone), 15-pentadec-11-enolide and/or 15-pentadec-12-enolide (Globalide), 15-cyclopentadecanolide (Macrolide), 1-(5,6,7,8-tetrahydro-3,5,5,6,8,8-hexamethyl-2-naphthalenyl)ethanone (Tonalide), ethylene brassylate, 2-ethyl-4-(2,2,3-trimethyl-3-cyclopenten-1-yl)-2-buten-1-ol (Sandranol), alpha-Santalol, 2,2-dimethyl-3-(3-methylphenyl)-propanol (Majantol), allyl heptanoate, 4-methylacetophenone, (4aR,5R,7aS,9R)-octahydro-2,2,5,8,8,9a-hexamethyl-4H-4-a,9-methanoazuleno (5,6-d)-1,3-dioxol) (Ambrocenide), Timberol (1-(2,2,6-trimethylcyclohexyl)hexan-3-ol), benzylacetone, methyl cinnamate, 3a,6,6,9a-tetramethyldodecahydronaphtho[2,1-b]furan (Ambroxid).

Cosmetic or pharmaceutical preparations containing one or more compounds of formula (I) may, in particular if crystalline or microcrystalline solid bodies such as, for example, inorganic micropigments are to be incorporated in the preparations, according to the invention also contain anionic, cationic, non-ionic and/or amphoteric surfactants mentioned in WO 2005/123101.

Anionic surfactants generally have carboxylate, sulfate or sulfonate groups as functional groups. In aqueous solution they form negatively charged organic ions in the acid or neutral environment. Cationic surfactants are almost exclusively characterised by the presence of a quaternary ammonium group. In aqueous solution they form positively charged organic ions in the acid or neutral environment. Amphoteric surfactants contain both anionic and cationic groups and therefore behave in aqueous solution in the same way as anionic or cationic surfactants, depending on the pH. They have a positive charge in a strongly acid environment and a negative charge in an alkaline environment. In the neutral pH range, by contrast, they are zwitterionic. Polyether chains are typical of non-ionic surfactants. Non-ionic surfactants do not form ions in the aqueous medium.

A. Anionic Surfactants

Anionic surfactants which can advantageously be used are acyl amino acids (and salts thereof), such as
  acyl glutamates, for example sodium acyl glutamate, di-TEA-palmitoyl aspartate and sodium caprylic/capric glutamate,
  acyl peptides, for example palmitoyl-hydrolysed milk protein, sodium cocoyl-hydrolysed soya protein and sodium/potassium cocoyl-hydrolysed collagen,
  sarcosinates, for example myristoyl sarcosin, TEA-lauroyl sarcosinate, sodium lauroyl sarcosinate and sodium cocoyl sarcosinate,
  taurates, for example sodium lauroyl taurate and sodium methyl cocoyl taurate,
  acyl lactylates, lauroyl lactylate, caproyl lactylate
  alaninates
carboxylic acids and derivatives, such as
for example lauric acid, aluminium stearate, magnesium alkanolate and zinc undecylenate,
  ester carboxylic acids, for example calcium stearoyl lactylate, laureth-6 citrate and sodium PEG-4 lauramide carboxylate,
  ether carboxylic acids, for example sodium laureth-13 carboxylate and sodium PEG-6 cocamide carboxylate,
phosphoric acid esters and salts, such as e.g. DEA-oleth-10-phosphate and dilaureth-4 phosphate,
sulfonic acids and salts, such as
  acyl isothionates, e.g. sodium/ammonium cocoyl isothionate,
  alkyl aryl sulfonates,
  alkyl sulfonates, for example sodium cocomonoglyceride sulfate, sodium $C_{12-14}$ olefin sulfonate, sodium lauryl sulfoacetate and magnesium PEG-3 cocamide sulfate,
  sulfosuccinates, for example dioctyl sodium sulfosuccinate, disodium laureth sulfosuccinate, disodium lauryl sulfosuccinate and disodium undecylenamido MEA sulfosuccinate and sulfuric acid esters, such as
- alkyl ether sulfate, for example sodium, ammonium, magnesium, MIPA, TIPA laureth sulfate, sodium myreth sulfate and sodium $C_{12-13}$ pareth sulfate,
- alkyl sulfates, for example sodium, ammonium and TEA lauryl sulfate.

B. Cationic Surfactants

Cationic surfactants which can advantageously be used are
- alkyl amines,
- alkyl imidazoles,
- ethoxylated amines and
- quaternary surfactants.
- $RNH_2CH_2CH_2COO^-$ (where pH=7)
- $RNHCH_2CH_2COO—B^+$ (where pH=12)=any cation, e.g. $Na^+$
- esterquats Quaternary surfactants contain at least one N atom, which is covalently bonded to 4 alkyl or aryl groups. This leads to a positive charge, regardless of the pH. Alkyl betaine, alkyl amidopropyl betaine and alkyl amidopropyl hydroxysulfaine are advantageous. The cationic surfactants used can also preferably be chosen from the group of quaternary ammonium compounds, in particular benzyl trialkyl ammonium chlorides or bromides, such as benzyl dimethylstearyl ammonium chloride for example, also alkyl trialkyl ammonium salts, for example cetyl trimethyl ammonium chloride or bromide, alkyl dimethyl hydroxyethyl ammonium chlorides or bromides, dialkyl dimethyl ammonium chlorides or bromides, alkyl amide ethyl trimethyl ammonium ether sulfates, alkyl pyridinium salts, for example lauryl or cetyl pyrimidinium chloride, imidazoline derivatives and compounds having a cationic character such as amine oxides, for example alkyl dimethyl amine oxides or alkyl aminoethyl dimethyl amine oxides. Cetyl trimethyl ammonium salts are particularly advantageously used.

C. Amphoteric Surfactants

Amphoteric surfactants which can advantageously be used are
- acyl/dialkyl ethylene diamine, for example sodium acyl amphoacetate, disodium acyl amphodipropionate, disodium alkyl amphodiacetate, sodium acyl amphohydroxypropyl sulfonate, disodium acyl amphodiacetate and sodium acyl amphopropionate,
- N-alkyl amino acids, for example aminopropyl alkyl glutamide, alkyl aminopropionic acid, sodium alkyl imidodipropionate and lauroamphocarboxyglycinate.

D. Non-Ionic Surfactants

Non-ionic surfactants which can advantageously be used are
- alcohols,
- alkanolamides, such as cocamides MEA/DEA/MIPA,
- amine oxides, such as cocamidopropylamine oxide,
- esters produced by esterification of carboxylic acids with ethylene oxide, glycerol, sorbitan or other alcohols,
- ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkyl polyglycosides such as lauryl glucoside, decyl glycoside and cocoglycoside,
- sucrose esters, ethers,
- polyglycerol esters, diglycerol esters, monoglycerol esters,
- methyl glucose esters, esters of hydroxy acids.

The use of a combination of anionic and/or amphoteric surfactants with one or more non-ionic surfactants is also advantageous.

The surface-active substance (surfactant) or the combination of surface-active substances can be present in the formulations according to the invention in a concentration of between 1 and 98 wt. %, based on the total weight of the formulations.

Cosmetic (e.g. dermatological) or pharmaceutical formulations according to the invention containing one or more compounds according to the invention or for use according to the invention having formula (I) can also take the form of emulsions.

The oil phase of preparations according to the invention, which contain one or more compounds of formula (I) may advantageously be selected from the substance groups mentioned in WO 2005/123101.

The oil phase (lipid phase) in the formulations according to the invention (in particular topical cosmetic formulations) can advantageously be selected from the following group of substances:
- mineral oils (advantageously paraffin oil), mineral waxes
- fatty oils, fats, waxes and other natural and synthetic fat bodies, preferably esters of fatty acids with low C-number alcohols, for example with isopropanol, propylene glycol or glycerol, or esters of fatty alcohols with low C-number alkanoic acids or with fatty acids;
- alkyl benzoates (e.g. mixtures of n-dodecyl, n-tridecyl, n-tetradecyl or n-pentadecyl benzoate);
- cyclic or linear silicone oils such as dimethyl polysiloxanes, diethyl polysiloxanes, diphenyl polysiloxanes and mixed forms thereof.

(Natural or synthetic) esters are advantageously used, in particular (a) esters of saturated and/or unsaturated branched and/or unbranched alkane carboxylic acids having a chain length of 3 to 30 C atoms and saturated and/or unsaturated, branched and/or unbranched alcohols having a chain length of 3 to 30 C atoms, (b) esters of aromatic carboxylic acids and saturated and/or unsaturated, branched and/or unbranched alcohols having a chain length of 3 to 30 C atoms. Preferred ester oils are isopropyl myristate, isopropyl palmitate, isopropyl stearate, isopropyl oleate, n-butyl stearate, n-hexyl laurate, n-decyl laurate, n-decyl oleate, isooctyl stearate, isononyl stearate, isononyl isononanoate, 3,5,5-trimethylhexyl-3,5,5-trimethylhexanoate, 2-ethylhexyl isononanoate, 2-ethylhexyl-3,5,5-trimethylhexanoate, 2-ethylhexyl-2-ethylhexanoate, cetearyl-2-ethylhexanoate, 2-ethylhexyl palmitate, 2-ethylhexyl laurate, 2-hexyldecyl stearate, 2-octyldecyl palmitate, 2-octyldodecyl palmitate, oleyl oleate, oleyl erucate, erucyl oleate, erucyl erucate and synthetic, semisynthetic and natural mixtures of such esters, e.g. jojoba oil.

The oil phase can also advantageously be chosen from the group consisting of branched and unbranched hydrocarbons and hydrocarbon waxes, silicone oils, dialkyl ethers, the group consisting of saturated or unsaturated, branched or unbranched alcohols, and of fatty acid triglycerides, in particular the triglycerol esters of saturated and/or unsaturated, branched and/or unbranched alkane carboxylic acids having a chain length of 8 to 24, in particular 12 to 18 C atoms. The fatty acid triglycerides can advantageously be selected from the group of synthetic, semisynthetic and natural oils, e.g. triglycerides of capric or caprylic acid, apricot kernel oil, avocado oil, cottonseed oil, borage seed oil, thistle oil, groundnut oil, gamma-oryzanol, rosehip seed oil, hemp oil, hazelnut oil, blackcurrant seed oil, coconut oil, cherry kernel oil, salmon oil, flax oil, maize oil, *macadamia* nut oil, almond oil, evening primrose oil, mink oil, olive oil, palm oil, palm kernel oil, pecan nut oil, peach kernel oil, pistachio nut oil, rapeseed oil, rice bran oil, castor oil, safflower oil, sesame oil, soya oil, sunflower oil, teatree oil, grape seed oil or wheat germ oil, and the like. Any blends of such oil and wax components can also advantageously be used. In some cases it is also advantageous to use waxes, for example cetyl palmitate, as the sole lipid component of the oil phase, the oil phase advantageously being chosen from the group consisting of 2-ethylhexyl isostearate, octyl dodecanol, isotridecyl isononanoate, isoeicosane, 2-ethylhexyl cocoate, $C_{12-15}$-alkyl benzoate, caprylic-capric acid triglyceride and dicaprylyl ether. Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous. The hydrocarbons paraffin oil, squalane and squalene can also advantageously be used. The oil phase can advantageously also have a content of cyclic or linear silicone oils or consist entirely of such oils, it being preferable, however, to use an additional content of other oil phase components along with the silicone oil or silicone oils. Cyclomethicone (e.g. decamethyl cyclopentasiloxane) can advantageously be used as the silicone oil. Other silicone oils can also advantageously be used, however, for example undecamethyl cyclotrisiloxane, polydimethyl siloxane and poly(methylphenyl siloxane). Mixtures of cyclomethicone and isotridecyl isononanoate and of cyclomethicone and 2-ethylhexyl isostearate are also particularly advantageous.

The aqueous phase of formulations according to the invention (in particular topical cosmetic formulations) in the form of an emulsion can advantageously include: alcohols, diols or polyols having a low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, also alcohols having a low C number, e.g. ethanol, isopropanol, 1,2-propanediol, glycerol and in particular one or more thickeners, which can advantageously be chosen from the group comprising silicon dioxide, aluminium silicates such as e.g. bentonites, polysaccharides or derivatives thereof, e.g. hyaluronic acid, guar gum, xanthan gum, hydroxypropyl methyl cellulose, or allulose derivatives, particularly advantageously from the group of polyacrylates, preferably a polyacrylate from the group of so-called carbopols, for example type 980, 981, 1382, 2984, 5984 carbopols, either individually or in combination, or from the group of polyurethanes, also alpha- or beta-hydroxy acids, preferably lactic acid, citric acid or salicylic acid, also emulsifiers, which can advantageously be selected from the group of ionic, non-ionic, polymeric, phosphate-containing and zwitterionic emulsifiers.

Formulations according to the invention in the form of an emulsion advantageously include one or more emulsifiers. O/W emulsifiers, for example, can advantageously be chosen from the group of polyethoxylated or polypropoxylated or polyethoxylated and polypropoxylated products, e.g.:
fatty alcohol ethoxylates,
ethoxylated wool wax alcohols,
polyethylene glycol ethers having the general formula $$R-O-(-CH_2-CH_2-O-)_n-R',$$

fatty acid ethoxylates having the general formula $$R-COO-(-CH_2-CH_2-O-)_n-H,$$

etherified fatty acid ethoxylates having the general formula $$R-COO-(-CH_2-CH_2-O-)_n-R',$$

esterified fatty acid ethoxylates having the general formula $$R-COO-(-CH_2-CH_2-O-)_n-C(O)-R',$$

polyethylene glycol glycerol fatty acid esters,
ethoxylated sorbitan esters,
cholesterol ethoxylates,
ethoxylated triglycerides,
alkyl ether carboxylic acids having the general formula $$R-COO-(-CH_2-CH_2-O-)_n-OOH,$$

where n represents a number from 5 to 30,
polyoxyethylene sorbitol fatty acid esters,
alkyl ether sulfates having the general formula $$R-O-(-CH_2-CH_2-O-)_n-SO_3-H,$$

fatty alcohol propoxylates having the general formula $$R-O-(-CH_2-CH(CH_3)-O-)_n-H,$$

polypropylene glycol ethers having the general formula $$R-O-(-CH_2-CH(CH_3)-O-)_n-R',$$

propoxylated wool wax alcohols,
etherified fatty acid propoxylates $$R-COO-(-CH_2-CH(CH_3)-O-)_n-R',$$

esterified fatty acid propoxylates having the general formula $$R-COO-(-CH_2-CH(CH_3)-O-)_n-C(O)-R',$$

fatty acid propoxylates having the general formula $$R-COO-(-CH_2-CH(CH_3)-O-)_n-H,$$

polypropylene glycol glycerol fatty acid esters,
propoxylated sorbitan esters,
cholesterol propoxylates,
propoxylated triglycerides,
alkyl ether carboxylic acids having the general formula $$R-O-(-CH_2-CH(CH_3)-O-)_n-CH_2-COOH,$$

alkyl ether sulfates or the acids on which these sulfates are based having the general formula $$R-O-(-CH_2-CH(CH_3)-O-)_n-SO_3-H,$$

fatty alcohol ethoxylates/propoxylates having the general formula $$R-O-X_n-Y_m-H,$$

polypropylene glycol ethers having the general formula $$R-O-X_n-Y_m-R',$$

etherified fatty acid propoxylates having the general formula $$R-COO-X_n-Y_m-R',$$

fatty acid ethoxylates/propoxylates having the general formula $$R-COO-X_n-Y_m-H.$$

Particularly advantageously according to the invention the polyethoxylated or polypropoxylated or polyethoxylated and polypropoxylated O/W emulsifiers used are chosen from the group of substances having HLB values of 11 to 18, most particularly advantageously having HLB values of 14.5 to 15.5, if the O/W emulsifiers have saturated R and R' radicals. If the O/W emulsifiers have unsaturated R and/or R' radicals, or if isoalkyl derivatives are present, the preferred HLB value of such emulsifiers can also be lower or higher.

It is advantageous to choose the fatty alcohol ethoxylates from the group of ethoxylated stearyl alcohols, cetyl alcohols, cetyl stearyl alcohols (cetearyl alcohols). Particularly preferred are:
polyethylene glycol (n) stearyl ether (steareth-n) where n=13-20,
polyethylene glycol (n) cetyl ether (ceteth-n) where n=13-20,
polyethylene glycol (n) isocetyl ether (isoceteth-n) where n=13-20,
polyethylene glycol (n) cetyl stearyl ether (ceteareth-n) where n=13-20,
polyethylene glycol (m) isostearyl ether (isosteareth-m) where m=12-20,
polyethylene glycol (k) oleyl ether (oleth-k) where k=12-15,
polyethylene glycol (12) lauryl ether (laureth-12),
polyethylene glycol (12) isolauryl ether (isolaureth-12).

It is also advantageous to choose the fatty acid ethoxylates from the following group:
polyethylene glycol (n) stearate where n=20-25,
polyethylene glycol (m) isostearate where m=12-25,
polyethylene glycol (k) oleate where k=12-20.

Sodium laureth-11 carboxylate can advantageously be used as the ethoxylated alkyl ether carboxylic acid or its salt. Sodium laureth 1-4 sulfate can advantageously be used as the alkyl ether sulfate. Polyethylene glycol (30) cholesteryl ether can advantageously be used as the ethoxylated cholesterol derivative. Polyethylene glycol (25) soya sterol has also proved itself.

Polyethylene glycol (60) evening primrose glycerides can advantageously be used as ethoxylated triglycerides.

It is also advantageous to choose the polyethylene glycol glycerol fatty acid esters from the group comprising polyethylene glycol (n) glyceryl laurate where n=20-23, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise beneficial to choose the sorbitan esters from the group comprising polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be used as advantageous W/O emulsifiers: fatty alcohols having 8 to 30 carbon atoms, monoglycerol esters of saturated and/or unsaturated, branched and/or unbranched alkane carboxylic acids having a chain length of 8 to 24, in particular 12 to 18 C atoms, diglycerol esters of saturated and/or unsaturated, branched and/or unbranched alkane carboxylic acids having a chain length of 8 to 24, in particular 12 to 18 C atoms, monoglycerol ethers of saturated and/or unsaturated, branched and/or unbranched alcohols having a chain length of 8 to 24, in particular 12 to 18 C atoms, diglycerol ethers of saturated and/or unsaturated, branched and/or unbranched alcohols having a chain length of 8 to 24, in particular 12 to 18 C atoms, propylene glycol esters of saturated and/or unsaturated, branched and/or unbranched alkane carboxylic acids having a chain length of 8 to 24, in particular 12 to 18 C atoms, and sorbitan esters of saturated and/or unsaturated, branched and/or unbranched alkane carboxylic acids having a chain length of 8 to 24, in particular 12 to 18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate.

The formulations according to the invention (in particular cosmetic, including dermatological formulations) can contain deodorants, i.e. active ingredients having a deodorising and perspiration-inhibiting action. These include, for example, odour maskers, such as the common perfume constituents, antiperspirants based on aluminium, zirconium or zinc salts, odour absorbers, for example the layered silicates described in DE-P 40 09 347, in particular montmorillonite, kaolinite, nontronite, saponite, hectorite, bentonite, smectite, and also zinc salts of ricinoleic acid, for example. They also include bactericidal or bacteriostatic deodorising substances, such as e.g. hexachlorophene, 2,4,4'-trichloro-2'-hydroxydiphenyl ether (Irgasan), 1,6-di-(4-chlorophenylbiguanido) hexane (chlorhexidine), 3,4,4'-trichlorocarbanilide, and the active agents described in the laid-open patent specifications DE-37 40 186, DE-39 38 140, DE-42 04 321, DE-42 29 707, DE-42 29 737, DE-42 37 081, DE-43 09 372, DE-43 24 219 and containing cation-active substances, such as e.g. quaternary ammonium salts and odour absorbers such as e.g. Grillocin® (combination of zinc ricinoleate and various additives) or triethyl citrate, optionally in combination with ion-exchange resins.

The amount of deodorising and/or antiperspirant active ingredients in the formulations is preferably 0.01 to 20 wt. %, based on the total weight of the formulations, particularly preferably 0.05 to 10 wt. %.

Preferred embodiments and further aspects of the present invention emerge from the attached patent claims and the following examples.

The examples describe the invention in more detail, without limiting the area of protection of the claims. Unless stated otherwise, all the data, in particular amounts and percentages, relate to the weight.

EXAMPLES 1

Synthesis of Compounds of Formula (I)

Example 1.1

Butyl-carbamic acid (1R,2S,5R)-2-isopropyl-5-methyl-cyclohexyl ester (BIO1267)

66.6 g of menthyl chloroformate (70% in toluene) were added to a mixture of 16.6 g of pyridine and 21.9 g n-butylamine in 100 mL toluene at 0° C. over a period of 50 minutes. After stirring for 12 hours at room temperature, 100 mL of 2M HCl and subsequently 50 mL water were added, the phases separated and the water phase discarded. After washing with saturated NaHCO$_3$-solution and water the organic phase was dried and evaporated to yield 55.1 g of crude product which was recrystallized from 30 g n-heptane to give 34.5 g of the analytically pure product as white crystals.

$^1$H-NMR (400 MHz, CDCl$_3$, TMS): δ=4.57 (m, H), 4.54 (d, t, 4.1 Hz, 10.8 Hz, H), 3.16 (m, 2H), 2.04 (d, 11.7 Hz, H), 1.92 (d, q, q, 2.3 Hz, 6.9 Hz, 6.9 Hz, H), 1.66 (m, 2H), 1.47 (m, 3H), 1.24-1.39 (m, 3H), 1.06 (m, H), 0.081-0.99 (m, 2H), 0.92 (t, 7.3 Hz, 3H), 0.90 (d, 6.5 Hz, 3H), 0.89 (d, 7.0 Hz, 3H), 0.79 (d, 6.9 Hz, 3H) ppm.

$^{13}$C-NMR (400 MHz, CDCl$_3$, TMS): δ=156.5 (s), 74.3 (d), 47.8 (d), 41.6 (t), 40.7 (t), 34.4 (t), 32.1 (t), 31.4 (d), 26.3 (d), 23.6 (t), 22.1 (q), 20.8 (q), 19.9 (t), 16.5 (q), 13.7 (q) ppm.

MS (EI): m/z=255 (<1), 254 (<1), 138 (83), 118 (100), 95 (88), 83 (83), 69 (33), 55 (53), 41 (39), 29 (20).

Example 1.2

Ethyl-carbamic acid (1R,2S,5R)-2-isopropyl-5-methyl-cyclohexyl ester (BIO1151)

58.7 g of menthyl chloroformate (80% in toluene) were added to a mixture of 16.6 g of pyridine and 150 mL ethylamine (2M solution in THF) in 100 mL toluene at 0° C. over a period of 30 minutes. After stirring for 12 hours at room temperature, 100 mL of 2M HCl and subsequently 50 mL water were added, the phases separated and the water phase discarded. After washing with saturated NaHCO$_3$-solution and water the organic phase was dried and evaporated to yield 47.1 g of crude product which was recrystallized from 82.4 g n-heptane to give 24.4 g of the analytically pure product as white crystals.

$^1$H-NMR (400 MHz, CDCl$_3$, TMS): δ=4.54 (d, t, 4.3 Hz, 10.8 Hz, H), 4.54 (m, H), 3.20 (q, 6.9 Hz, 2H), 2.05 (m, H), 1.92 (d, q, q, 2.7 Hz, 7.0 Hz, 7.0 Hz, H), 1.61-1.71 (m, 2H), 1.48 (m, H), 1.30 (m, H), 1.13 (t, 7.2 Hz, 3H), 1.06 (m, H), 0.82-0.99 (m, 2H), 0.90 (d, 6.6 Hz, 3H), 0.89 (d, 7.0 Hz, 3H), 0.79 (d, 7.0 Hz, 3H) ppm.

$^{13}$C-NMR (400 MHz, CDCl$_3$, TMS): δ=156.4 (s), 74.3 (d), 47.5 (d), 41.5 (t), 35.8 (t), 34.4 (t), 31.4 (d), 26.3 (d), 23.6 (t), 22.1 (q), 20.8 (q), 16.5 (q), 15.3 (q) ppm.

MS (EI): m/z=228 (<1), 227 (not detected), 138 (82), 123 (42), 95 (100), 90 (71), 81 (75), 71 (49), 55 (49), 41 (52), 29 (33).

The menthyl carbamates according to examples 1.3 to 1.20 were produced analogously to the methodology described in example 1.1. and example 1.2.

Example 1.3

Cyclohexyl-carbamic acid (1R,2S,5R)-2-isopropyl-5-methyl-cyclohexyl ester (BIO1266)

$^1$H-NMR (400 MHz, CDCl$_3$, TMS): δ=4.54 (d, t, 4.0 Hz, 11.0 Hz, H), 4.47 (m, H), 3.46 (m, H), 2.04 (d, 12.0 Hz, H), 1.87-1.97 (m, 3H), 1.56-1.74 (m, 5H), 1.48 (m, H), 1.33 (m, 3H), 1.11 (m, 4H), 0.93 (m, H), 0.90 (d, 6.6 Hz, 3H), 0.89 (d, 7.0 Hz, 3H), 0.84 (m, H), 0.79 (d, 7.0 Hz, 3H) ppm.

$^{13}$C-NMR (400 MHz, CDCl$_3$, TMS): δ=155.7 (s), 74.1 (d), 49.7 (d), 47.5 (d), 41.6 (t), 34.4 (t), 33.5 (t), 33.5 (t), 31.4 (d), 26.3 (d), 25.6 (t), 24.8 (t), 24.8 (t), 23.6 (t), 22.1 (q), 20.8 (q), 16.5 (q) ppm.

MS (EI): m/z=282 (<1), 281 (<1), 144 (87), 138 (65), 95 (49), 83 (100), 69 (37), 55 (67), 41 (36).

Example 1.4

(2-Ethoxy-phenyl)-carbamic acid (1R,2S,5R)-2-isopropyl-5-methyl-cyclohexyl ester (BIO1632)

$^1$H-NMR (400 MHz, CDCl$_3$, TMS): δ=8.11 (m, H), 7.18 (m, H), 6.94 (m, 2H), 6.84 (m, H), 4.69 (d, t, 4.4 Hz, 10.8 Hz, H), 4.09 (q, 7.0 Hz, 2H), 2.12 (d, 12.1 Hz, H), 2.00 (d, q, q, 2.8 Hz, 7.0 Hz, H), 1.70 (m, 2H), 1.54 (m, H), 1.46 (t, 7.0 Hz, 3H), 1.41 (m, H), 1.09 (m, H), 1.04 (d, t, 11.1 Hz, 12.1 Hz, H), 0.92 (d, 7.0 Hz, 3H), 0.92 (d, 6.5 Hz, 3H), 0.88 (m, H), 0.82 (d, 6.9 Hz, 3H) ppm.

$^{13}$C-NMR (400 MHz, CDCl$_3$, TMS): δ=153.3 (s), 146.7 (s), 128.0 (s), 122.4 (d), 121.0 (d), 118.1 (d), 110.9 (d), 74.9 (d), 64.1 (t), 47.3 (d), 41.4 (t), 34.3 (t), 31.4 (d), 26.2 (d), 23.5 (t), 22.1 (q), 20.8 (q), 16.4 (q), 14.9 (q) ppm.

MS (EI): m/z=320 (6), 319 (31), 181 (67), 137 (100), 108 (40), 83 (86), 69 (35), 55 (51), 41 (24).

Example 1.5

(2-Acetyl-phenyl)-carbamic acid (1R,2S,5R)-2-isopropyl-5-methyl-cyclohexyl ester (BIO1633)

$^1$H-NMR (400 MHz, CDCl$_3$, TMS): δ=11.1 (m, H), 8.51 (d, 8.6 Hz, H), 7.87 (d, 8.0 Hz, H), 7.53 (d, d, 8.5 Hz, 7.2 Hz, H), 7.05 (d, d, 7.2 Hz, 8.0 Hz, H), 4.65 (d, t, 4.4 Hz, 10.8 Hz, H), 2.66 (s, 3H), 2.10 (d, 11.9 Hz, H), 1.99 (d, q, q, 2.7 Hz, 6.9 Hz, 6.9 Hz, H), 1.69 (m, 2H), 1.52 (m, H), 1.43 (t, 10.9 Hz, H), 1.09 (m, H), 1.06 (d, t, 11.1 Hz, 12.0 Hz, H), 0.92 (d, 6.5 Hz, 3H), 0.91 (d, 7.0 Hz, 3H), 0.88 (m, H), 0.81 (d, 6.9 Hz, 3H) ppm.

$^{13}$C-NMR (400 MHz, CDCl$_3$, TMS): δ=202.3 (s), 153.8 (s), 141.7 (s), 135.0 (d), 131.7 (d), 121.4 (s), 121.1 (d), 119.2 (d), 75.1 (d), 47.1 (d), 41.2 (t), 34.3 (t), 31.5 (d), 28.6 (q), 26.2 (d), 23.6 (t), 22.1 (q), 20.8 (q), 16.5 (q) ppm.

MS (EI): m/z=318 (2), 317 (11), 135 (100), 120 (25), 83 (83), 69 (31), 55 (45), 43 (27).

Example 1.6

Benzyl-carbamic acid (1R,2S,5R)-2-isopropyl-5-methyl-cyclohexyl ester (BIO1695)

$^1$H-NMR (400 MHz, CDCl$_3$, TMS): δ=7.34 (m, 3H), 7.28 (m, 2H), 7.27 (m, H), 4.89 (m, H), 4.59 (d, t, 4.4 Hz, 10.9 Hz, H), 4.37 (m, 2H), 2.07 (d, 12.1 Hz, H), 1.93 (m, H), 1.66 (m, 2H), 1.49 8 m, H), 1.31 (t, t, 3.0 Hz, 10.8 Hz, H), 1.06 (m, H), 0.96 (d, t, 11.0 Hz, 12.0 Hz, H), 0.90 (d, 6.6 Hz, 3H), 0.89 (d, 7.1 Hz, 3H), 0.85 (m, H), 0.80 (d, 7.1 Hz, 3H) ppm.

$^{13}$C-NMR (400 MHz, CDCl$_3$, TMS): δ=156.5 (s), 138.8 (s), 128.6 (d), 18.6 (d), 127.5 (d), 127.4 (d), 127.4 (d), 74.8 (d), 47.4 (d), 45.0 (t), 41.5 (t), 34.3 (t), 31.4 (d), 26.3 (d), 23.6 (t), 22.1 (q), 20.8 (q), 16.5 (q) ppm.

MS (EI): m/z=290 (<1), 289 (1), 150 (100), 138 (27), 123 (11), 106 (10), 91 (37), 69 (16), 55 (21), 41 (13).

Example 1.7

Cyclohexylmethyl-carbamic acid (1R,2S,5R)-2-isopropyl-5-methyl-cyclohexyl ester (BIO1699)

$^1$H-NMR (400 MHz, CDCl$_3$, TMS): δ=4.61 (m, H), 4.54 (d, t, 4.3 Hz, 10.8 Hz, H), 3.00 (m, 2H), 2.04 (d, 12.1 Hz, H), 1.92 (d, q, q, 2.5 Hz, 7.0 Hz, 7.0 Hz, H), 1.69 (m, 7H), 1.46 (m, 2H), 0.81-1.33 (m, 9H), 0.85 (d, 6.6 Hz, 3H), 0.89 (d, 7.0 Hz, 3H), 0.79 (d, 7.0 Hz, 3H) ppm.

$^{13}$C-NMR (400 MHz, CDCl$_3$, TMS): δ=156.6 (s), 74.3 (d), 47.5 (d), 47.2 (t), 41.6 (t), 38.3 (d), 34.4 (t), 31.4 (d), 30.7 (t), 30.7 (t), 26.4 (t), 26.3 (d), 25.9 (t), 25.8 (t), 23.6 (t), 22.1 (q), 20.8 (q), 16.5 (q) ppm.

MS (EI): m/z=296 (<1), 295 (<1), 158 (100), 138 (95), 123 (17), 95 (42), 83 (57), 69 (18), 55 (39), 41 (21).

Example 1.8

(Tetrahydro-furan-2-ylmethyl)-carbamic acid (1R, 2S,5R)-2-isopropyl-5-methyl-cyclohexyl ester (BIO1702)

main signals of isomer mixture:
$^1$H-NMR (400 MHz, CDCl$_3$, TMS): δ=4.94 (m, H), 4.54 (t, 9.9 Hz, H), 3.96 (m, H), 3.85 (t, d, 6.5 Hz, 8.4 Hz, H), 3.74 (d, d, d, 2.6 Hz, 6.8 Hz, 8.2 Hz, H), 3.42 (m, H), 3.15 (d, d, d, 5.4 Hz, 6.8 Hz, 12.1 Hz, H), 2.03 (d, 12.1 Hz, H), 1.93 (m, 4H), 1.66 (m, 2H), 1.56 (m, H), 1.48 (m, H), 1.30 (t, 11.4 Hz, H), 1.06 (m, H), 0.94 (d, t, 10.9 Hz, 12.0 Hz, H), 0.90 (d, 6.6 Hz, 3H), 0.89 (d, 7.0 Hz, 3H), 0.84 (m, H), 0.79 (d, 6.9 Hz, 3H) ppm.
$^{13}$C-NMR (400 MHz, CDCl$_3$, TMS): δ=156.7 (s), 78.0 (d), 74.5 (d), 68.1 (t), 47.4 (d), 44.7 (t), 41.5 (d), 34.3 (t), 31.3 (d), 28.4 (t), 26.2 (d), 25.9 (t), 23.6 (t), 22.1 (q), 20.8 (q), 16.5 (q) ppm.
MS (EI): m/z=285 (<1), 284 (1), 139 (33), 102 (18), 83 (46), 71 (100), 55 (21), 43 (25).

Example 1.9

(2-Methoxy-ethyl)-carbamic acid (1R,2S,5R)-2-isopropyl-5-methyl-cyclohexyl ester (BIO1336)

$^1$H-NMR (400 MHz, CDCl$_3$, TMS): δ=4.96 (m, H), 4.54 (d, t, 4.1 Hz, 10.8 Hz, H), 3.45 (t, 4.9 Hz, 2H), 3.36 (s, 3H), 3.36 (m, 2H), 2.04 (d, 12.8 Hz, H), 1.93 (d, q, q, 2.6 Hz, 7.0 Hz, 7.0 Hz, H), 1.66 (m, 2H), 1.48 (m, H), 1.30 (t, 11.5 Hz, H), 1.06 (m, H), 0.95 (m, H), 0.90 (d, 6.5 Hz, 3H), 0.89 (d, 7.0 Hz, 3H), 0.85 (m, H), 0.79 (d, 7.0 Hz, 3H) ppm.
$^{13}$C-NMR (400 MHz, CDCl$_3$, TMS): δ=156.5 (s), 74.6 (d), 71.5 (t), 58.8 (q), 47.4 (d), 41.5 (t), 40.7 (d), 34.3 (t), 31.3 (d), 26.2 (d), 23.6 (t), 22.1 (q), 20.8 (q), 16.5 (q) ppm.
MS (EI): m/z=258 (<1), 257 (1), 119 (37), 95 (45), 83 (100), 76 (25), 69 (39), 55 (45), 41 (28), 30 (20).

Example 1.10

(6-Hydroxy-hexyl)-carbamic acid (1R,2S,5R)-2-isopropyl-5-methyl-cyclohexyl ester (BIO1662)

$^1$H-NMR (400 MHz, CDCl$_3$, TMS): δ=4.54 (m, 2H), 3.64 (t, 6.6 Hz, 2H), 3.17 (m, 2H), 2.04 (d, 12.3 Hz, H), 1.91 (d, q, q, 2.5 Hz, 6.9 Hz, 6.9 Hz, H), 1.66 (m, 2H), 1.24-1.61 (m, 11H), 1.06 (m, H), 0.93 (m, H), 0.90 (d, 6.6 Hz, 3H), 0.89 (d, 7.0 Hz, 3H), 0.86 (m, H), 0.79 (d, 6.9 Hz, 3H) ppm.
$^{13}$C-NMR (400 MHz, CDCl$_3$, TMS): δ=156.6 (s), 74.3 (d), 62.5 (t), 47.4 (d), 41.5 (t), 40.7 (t), 34.3 (t), 32.6 (t), 31.4 (d), 30.0 (t), 26.4 (t), 26.3 (d), 25.3 (t), 23.5 (t), 22.1 (q), 20.8 (q), 16.5 (q) ppm.
MS (EI): m/z=299 (<1), 138 (30), 123 (31), 95 (82), 81 (83), 71 (74), 55 (90), 41 (100), 31 (45).

Example 1.11

(3-Methoxy-propyl)-carbamic acid (1R,2S,5R)-2-isopropyl-5-methyl-cyclohexyl ester (BIO1155)

$^1$H-NMR (400 MHz, CDCl$_3$, TMS): δ=4.96 (m, H), 4.54 (d, t, 4.1 Hz, 10.7 Hz, H), 3.45 (t, 6.0 Hz, 2H), 3.33 (s, 3H), 3.28 (d, t, 6.0 Hz, 6.0 Hz, 2H), 2.04 (d, 11.5 Hz, H), 1.92 (d, q, q, 2.4 Hz, 7.0 Hz, 7.0 Hz, H), 1.78 (t, t, 6.3 Hz, 6.3 Hz, 2H), 1.66 (m, 2H), 1.48 (m, H), 1.29 (t, 11.1 Hz, H), 1.06 (m, H), 0.81-0.99 (m, 2H), 0.90 (d, 6.5 Hz, 3H), 0.89 (d, 7.0 Hz, 3H), 0.79 (d, 7.0 Hz, 3H) ppm.
$^{13}$C-NMR (400 MHz, CDCl$_3$, TMS): δ=156.5 (s), 74.3 (d), 71.1 (t), 58.7 (q), 47.4 (d), 41.5 (t), 39.0 (t), 34.4 (t), 31.4 (d), 29.7 (t), 26.3 (d), 23.6 (t), 22.1 (q), 20.8 (q), 16.5 (q) ppm.
MS (EI): m/z=271 (1), 138 (50), 101 (36), 95 (86), 90 (72), 83 (100), 71 (58), 55 (57), 41 (42), 30 (19).

Example 1.12

(3-Isopropoxy-propyl)-carbamic acid (1R,2S,5R)-2-isopropyl-5-methyl-cyclohexyl ester (BIO1268)

$^1$H-NMR (400 MHz, CDCl$_3$, TMS): δ=5.01 (m, H), 4.53 (d, t, 4.1 Hz, 10.8 Hz, H), 3.55 (q, q, 6.0 Hz, 6.0 Hz, H), 3.48 (t, 5.8 Hz, 2H), 3.28 (d, t, 6.3 Hz, 6.3 Hz, 2H), 2.04 (d, 11.6 Hz, 1.92 (d, q, q, 2.4 Hz, 7.0 Hz, 7.0 Hz, H), 1.75 (t, t, 6.2 Hz, 6.2 Hz, 2H), 1.66 (m, 2H), 1.48 (m, H), 1.29 (m, H), 1.15 (d, 6.1 Hz, 6H), 1.06 (m, H), 0.81-0.99 (m, 2H), 0.90 (d, 6.5 Hz, 3H), 0.89 (d, 7.0 Hz, 3H), 0.79 (d, 7.0 Hz, 3H) ppm.
$^{13}$C-NMR (400 MHz, CDCl$_3$, TMS): δ=156.5 (s), 74.3 (d), 71.6 (d), 66.5 (t), 47.4 (d), 41.5 (t), 39.3 (t), 34.4 (t), 31.4 (d), 30.0 (t), 26.4 (t), 23.7 (t), 22.1 (q), 22.1 (q), 22.1 (q), 20.8 (q), 16.6 (q) ppm.
MS (EI): m/z=300 (<1), 299 (<1), 118 (93), 102 (100), 95 (42), 83 (84), 57 (64), 43 (42).

Example 1.13

Hexyl-carbamic acid (1R,2S,5R)-2-isopropyl-5-methyl-cyclohexyl ester (BIO1271)

$^1$H-NMR (400 MHz, CDCl$_3$, TMS): δ=4.57 (m, H), 4.54 (d, t, 4.2 Hz, 10.8 Hz, H), 3.15 (m, 2H), 2.04 (m, H), 1.92 (d, q, q, 2.3 Hz, 7.0 Hz, 7.0 Hz, H), 1.66 (m, 2H), 1.41-1.55 (m, 4H), 1.24-1.36 (m, 6H), 1.06 (m, H), 0.81-0.99 (m, 2H), 0.90 (d, 6.5 Hz, 3H), 0.89 (t, 7.0 Hz, 3H), 0.89 (d, 7.0 Hz, 3H), 0.79 (d, 7.0 Hz, 3H) ppm.
$^{13}$C-NMR (400 MHz, CDCl$_3$, TMS): δ=156.5 (s), 74.3 (d), 47.5 (d), 41.6 (t), 41.0 (t), 34.4 (t), 31.5 (t), 31.4 (d), 30.0 (t), 26.4 (t), 26.3 (d), 23.6 (t), 22.6 (t), 22.1 (q), 20.8 (q), 16.5 (q), 14.0 (q) ppm.
MS (EI): m/z=284 (<1), 283 (<1), 146 (86), 138 (79), 95 (70), 83 (100), 69 (35), 55 (53), 43 (41), 30 (20).

Example 1.14

Isopropyl-carbamic acid (1R,2S,5R)-2-isopropyl-5-methyl-cyclohexyl ester (BIO1272)

$^1$H-NMR (400 MHz, CDCl$_3$, TMS): δ=4.53 (d, t, 3.9 Hz, 10.6 Hz, H), 4.39 (m, H), 3.78 (m, H), 2.03 (d, 12.0 Hz, H), 1.90 (d, q, q, 2.5 Hz, 7.0 Hz, 7.0 Hz, H), 1.64 (m, 2H), 1.47 (m, H), 1.27 (m, H), 1.13 (d, 6.6 Hz, 6H), 1.04 (m, H), 0.80-0.98 (m, 2H), 0.88 (d, 6.5 Hz, 3H), 0.88 (d, 7.0 Hz, 3H), 0.78 (d, 6.9 Hz, 3H) ppm.
$^{13}$C-NMR (400 MHz, CDCl$_3$, TMS): δ 155.7 (s), 74.2 (d), 47.5 (d), 42.9 (d), 41.6 (t), 34.4 (t), 31.4 (d), 26.3 (d), 23.6 (t), 23.1 (q), 23.1 (q), 22.1 (q), 20.8 (q), 16.5 (q) ppm.

MS (EI): m/z=242 (<1), 241 (<1), 226 (4), 138 (94), 104 (97), 95 (97), 83 (100), 69 (42), 55 (64), 43 (53), 29 (12).

Example 1.15

Isobutyl-carbamic acid (1R,2S,5R)-2-isopropyl-5-methyl-cyclohexyl ester (BIO1159)

$^1$H-NMR (400 MHz, CDCl$_3$, TMS): δ=4.64 (m, H), 4.54 (d, t, 4.2 Hz, 10.8 Hz, H), 3.00 (m, 2H), 2.04 (d, 11.9 Hz, H), 1.92 (d, q, q, 2.7 Hz, 7.0 Hz, 7.0 Hz, H), 1.75 (m, H), 1.66 (m, 2H), 1.48 (m, H), 1.29 (t, 11.6 Hz, H), 1.06 (m, H), 0.81-0.99 (m, 2H), 0.91 (d, 6.7 Hz, 6H), 0.90 (d, 7.1 Hz, 3H), 0.90 (d, 6.5 Hz, 3H), 0.79 (d, 7.0 Hz, 3H) ppm.
$^{13}$C-NMR (400 MHz, CDCl$_3$, TMS): δ=156.6 (s), 74.3 (d), 48.3 (t), 47.5 (d), 41.5 (t), 34.4 (t), 31.4 (d), 28.9 (d), 26.4 (d), 23.6 (t), 22.1 (q), 20.8 (q), 19.9 (q), 19.9 (q), 16.5 (q) ppm.
MS (EI): m/z=255 (<1), 212 (1), 138 (71), 118 (62), 95 (47), 83 (100), 69 (29), 57 (41), 41 (28), 30 (26).

Example 1.16

Methyl-carbamic acid (1S,2R,5S)-2-isopropyl-5-methyl-cyclohexyl ester (BIO1301)

$^1$H-NMR (400 MHz, CDCl$_3$, TMS): δ=4.57 (m, H), 4.52 (d, t, 4.4 Hz, 10.7 Hz, H), 2.76 (d, 4.9 Hz, 3H), 2.02 (d, 11.5 Hz, H), 1.90 (d, q, q, 2.5 Hz, 7.0 Hz, 7.0 Hz, H), 1.64 (m, 2H), 1.46 (m, H), 1.27 (t, 11.0 Hz, H), 1.04 (m, H), 0.79-0.96 (m, 2H), 0.88 (d, 6.5 Hz, 3H), 0.87 (d, 7.0 Hz, 3H), 0.77 (d, 7.0 Hz, 3H) ppm.
$^{13}$C-NMR (400 MHz, CDCl$_3$, TMS): δ=157.1 (s), 74.4 (d), 47.4 (d), 41.5 (t), 34.3 (t), 31.4 (d), 27.5 (q), 26.2 (d), 23.5 (t), 22.1 (q), 20.8 (q), 16.5 (q) ppm.
MS (EI): m/z=214 (<1), 213 (not detected), 138 (72), 123 (38), 95 (100), 81 (81), 76 (43), 67 (29), 55 (48), 41 (33), 29 (12).

Example 1.17

(2-Hydroxy-ethyl)-carbamic acid (1R,2S,5R)-2-isopropyl-5-methyl-cyclohexyl ester (BIO1338)

$^1$H-NMR (400 MHz, CDCl$_3$, TMS): δ=5.01 (m, H), 4.55 (d, t, 4.0 Hz, 10.7 Hz, H), 3.73 (m, 2H), 3.34 (m, 2H), 2.31 (m, 3H), 2.05 (d, 11.9 Hz, H), 1.92 (d, q, q, 2.7 Hz, 7.0 Hz, 7.0 Hz, H), 1.67 (m, 2H), 1.48 (m, H), 1.31 (t, 11.9 Hz, H), 1.06 (m, H), 0.79-1.01 (m, 2H), 0.90 (d, 6.6 Hz, 3H), 0.89 (d, 7.0 Hz, 3H), 0.79 (d, 7.0 Hz, 3H) ppm.
$^{13}$C-NMR (400 MHz, CDCl$_3$, TMS): δ=157.4 (s), 74.9 (d), 62.3 (t), 47.3 (d), 43.4 (t), 41.4 (t), 34.3 (t), 31.4 (d), 26.2 (d), 23.5 (t), 22.1 (q), 20.8 (q), 16.4 8 q) ppm.
MS (EI): m/z=243 (<1), 138 (57), 106 (40), 95 (65), 83 (100), 69 (40), 55 (57), 41 (38).

Example 1.18

Benzo[1,3]dioxol-5-ylmethyl-carbamic acid (1R,2S, 5R)-2-isopropyl-5-methyl-cyclohexyl ester (BIO1571)

$^1$H-NMR (400 MHz, CDCl$_3$, TMS): δ=6.78 (m, H), 6.76 (d, 7.9 Hz, H), 6.73 (d, 7.9 Hz, H), 4.87 (m, H), 4.58 (d, t, 4.4 Hz, 10.8 Hz, H), 4.27 (m, 2H); 2.06 (d, 11.9 Hz, H), 1.92 (m, H), 1.62-1.71 (m, 2H), 1.49 (m, H), 1.30 (t, 12.0 Hz, H), 1.06 (m, H), 0.81-0.99 (m, 2H), 0.90 (d, 6.6 Hz, 3H), 0.88 (d, 7.0 Hz, 3H), 0.80 (d, 7.0 Hz, 3H) ppm.
$^{13}$C-NMR (400 MHz, CDCl$_3$, TMS): δ=156.4 (s), 147.9 (s), 146.9 (s), 132.7 (s), 120.7 (d), 108.2 (d), 108.1 (d), 101.0 (t), 74.8 (d), 47.4 (d), 44.9 (t), 41.5 (t), 34.3 (t), 31.4 (d), 26.3 (d), 23.5 (t), 22.1 (q), 20.8 (q), 16.5 (q) ppm.
MS (EI): m/z=334 (2), 333 (9), 150 (15), 135 (30), 95 (11), 83 (16), 69 (11), 55 (17), 41 (12).

Example 1.19

Phenyl-carbamic acid (1R,2S,5R)-2-isopropyl-5-methyl-cyclohexyl ester (BIO1580)

$^1$H-NMR (400 MHz, CDCl$_3$, TMS): δ=7.39 (m, 2H), 7.30 (m, 2H), 7.04 (m, H), 6.55 (m, H), 4.66 (d, t, 4.4 Hz, 10.9 Hz, H), 2.11 (d, 12.0 Hz, H), 1.97 (d, q, q, 2.7 Hz, 6.9 Hz, 6.9 Hz, H), 1.69 (m, 2H), 1.52 (m, H), 1.37 (d, d, 10.9 Hz, 12.5 Hz, H), 1.09 (m, H), 1.01 (d, t, 10.8 Hz, 11.9 Hz, H), 0.92 (d, 6.5 Hz, 3H), 0.91 (d, 7.0 Hz, 3H), 0.88 (m, H), 0.81 (d, 6.9 Hz, 3H) ppm.
$^{13}$C-NMR (400 MHz, CDCl$_3$, TMS): δ=153.3 (s), 138.2 (s), 129.0 (d), 129.0 (d), 123.2 (d), 118.4 (d), 118.4 (d), 75.1 (d), 47.4 (d), 41.4 (t), 34.3 (t), 31.4 (d), 26.3 (d), 23.5 (t), 22.0 (q), 20.8 (q), 16.4 (q) ppm.
MS (EI): m/z=276 (4), 275 (21), 137 (44), 119 (25), 93 (93), 83 (100), 69 (33), 55 (40), 41 (23).

Example 1.20

Methyl-carbamic acid (1R,2S,5R)-2-isopropyl-5-methyl-cyclohexyl ester (BIO1185)

$^1$H-NMR (400 MHz, CDCl$_3$, TMS): δ=4.57 (m, H), 4.52 (d, t, 4.4 Hz, 10.7 Hz, H), 2.76 (d, 4.9 Hz, 3H), 2.02 (d, 11.5 Hz, H), 1.90 (d, q, q, 2.5 Hz, 7.0 Hz, 7.0 Hz, H), 1.64 (m, 2H), 1.46 (m, H), 1.27 (t, 11.0 Hz, 11.0 Hz, H), 1.04 (m, H), 0.91 (m, H), 0.87 (d, 6.5 Hz, 3H), 0.87 (d, 7.0 Hz, 3H), 0.82 (m, H), 0.77 (d, 7.0 Hz, 3H) ppm.
$^{13}$C-NMR (200 MHz, CDCl$_3$, TMS): δ=157.1 (s), 74.4 (d), 47.4 (d), 41.5 (t), 34.3 (t), 31.4 (d), 27.5 (q), 26.2 (d), 23.5 (t), 22.1 (q), 20.8 (q), 16.5 (q), ppm.
MS (EI): m/z=213 (not detected), 198 (0), 138 (62), 123 (34), 95 (100), 81 (79), 76 (49), 55 (52), 41 (50).

Example 1.21

Diethyl-carbamic acid (1R,2S,5R)-2-isopropyl-5-methyl-cyclohexyl ester (BIO1553)

30 mmol of l-menthol were placed with 110 ml dichlormethane in a 250 ml vessel at room temperature and 3.08 g (39 mmol) of pyridine were added. The reaction mixture was cooled to 0° C. and 3.56 g (12 mmol) of triphosgene in 15 ml dichlormethane were added dropwise. After five minutes 2.37 g (30 mmol) pyridine were added. Subsequently, 2.19 g (30 mmol) of diethylamine in 15 ml dichlormethane were added dropwise, the resulting mixture was allowed to come to ambient temperature and then quenched with water. After separation of the phases, the water phase was extracted once with dichlormethane and the combined organic phases were concentrated. The raw product was purified by distillation and column chromatography to yield 1.5 g of the desired product as a mixture of isomers with a purity of 99.4%.

Main signals of isomer mixture:

$^1$H-NMR (400 MHz, CDCl$_3$, TMS): δ=4.57 (d, t, 4.4 Hz, 10.8 Hz, H), 3.26 (m, 4H), 2.06 (d, 12.0 Hz, H), 1.94 (d, q, q, 2.8 Hz, 7.0 Hz, 7.0 Hz, H), 1.69 (m, H), 1.65 (m, H), 1.49 (m, H), 1.36 (d, d, t, 3.0 Hz, 10.8 Hz, 12.4 Hz, H), 1.11 (t, 7.1 Hz, 6H), 1.07 (m, H), 0.95 (d, d, 10.9 Hz, 12.1 Hz, H), 0.90 (d, 7.0 Hz, 3H), 0.90 (d, 6.6 Hz, 3H), 0.86 (m, H), 0.79 (d, 6.9 Hz, 3H) ppm.

$^{13}$C-NMR (400 MHz, CDCl$_3$, TMS): δ=155.8 (s), 74.6 (d), 47.5 (d), 41.6 (t), 40.9 (t), 40.9 (t), 34.4 (t), 31.4 (d), 26.3 (d), 23.5 (t), 22.1 (q), 20.9 (q), 16.4 (q), 13.9 (q), 13.9 (q) ppm.

MS (EI): m/z=255 (2), 138 (82), 118 (100), 95 (50), 83 (93), 69 (67), 55 (63), 41 (31), 29 (32).

Example 2

Depigmenting Effect on Melanoma Cell Cultures

B16V mouse melanoma cells are disseminated in a 96-well microtitre plate in a concentration of 5×10$^3$ cells/well. After cultivation for 24 h at 37° C. and 5% CO$_2$ in RPMI medium, enriched with 10% foetal calf serum, various concentrations of the test substances and 0.3 mM tyrosine and 10 nM α-MSH (α-melanocyte stimulating hormone) are added and incubated for a further 96 h. The maximum concentration of the test substances used corresponds to 0.1 times the value of the IC$_{20}$ value of the cytotoxicity assay. Standards are incubated with kojic acid in concentrations of 0.01 mM, 0.1 mM and 1 mM in addition to tyrosine and α-MSH. Only tyrosine and α-MSH are added to the controls. After incubation, sodium lauryl sulfate and sodium hydroxide solution (final concentrations: 1 mM and 1 M respectively) are added to the culture medium and the absorption (A) is measured after 3 h at 400 nm.

The inhibition of pigmentation in the presence of the test compounds or kojic acid was calculated using the following equation:

Inhibition of pigmentation(%)=100−[(A$_{test\ compound}$/A$_{control}$)×100]

wherein

A$_{test\ compound}$=absorption of the wells with test substance and with cells

A$_{control}$=absorption of the wells without test substance, but with cells

From the inhibition of pigmentation (%) in a series of dilutions of test compounds, the IC$_{50}$ for each test compound is calculated. This is the concentration of a test compound at which pigmentation is inhibited by 50%.

TABLE 2

| | test substance | IC 50 [μM] |
|---|---|---|
| reference | Kojic acid | 452.3 |
| reference | beta-Arbutin | 67.0 |
| BIO1151 | Ethyl-carbamic acid (1R,2S,5R)-2-isopropyl-5-methyl-cyclohexyl ester | 40.9 |
| BIO1571 | Benzo[1,3]dioxol-5-ylmethyl-carbamic acid (1R,2S,5R)-2-isopropyl-5-methyl-cyclohexyl ester | 5.5 |
| BIO1266 | Cyclohexyl-carbamic acid (1R,2S,5R)-2-isopropyl-5-methyl-cyclohexyl ester | 18.8 |
| BIO1460 | (3-Methoxy-propyl)-carbamic acid (1S,2S,5R)-2-isopropyl-5-methyl-cyclohexyl ester | 7.3 |
| BIO1461 | Ethyl-carbamic acid (1S,2S,5R)-2-isopropyl-5-methyl-cyclohexyl ester | 28.7 |
| BIO1580 | Phenyl-carbamic acid (1R,2S,5R)-2-isopropyl-5-methyl-cyclohexyl ester | 6.9 |
| BIO1632 | (2-Ethoxy-phenyl)-carbamic acid (1R,2S,5R)-2-isopropyl-5-methyl-cyclohexyl ester | 3.2 |
| BIO1633 | (2-Acetyl-phenyl)-carbamic acid (1R,2S,5R)-2-isopropyl-5-methyl-cyclohexyl ester | 25.4 |
| BIO1695 | Benzyl-carbamic acid (1R,2S,5R)-2-isopropyl-5-methyl-cyclohexyl ester | 7.7 |
| BIO1699 | Cyclohexylmethyl-carbamic acid (1R,2S,5R)-2-isopropyl-5-methyl-cyclohexyl ester | 1.4 |
| BIO1155 | (3-Methoxy-propyl)-carbamic acid (1R,2S,5R)-2-isopropyl-5-methyl-cyclohexyl ester | 22.1 |
| BIO1267 | Butyl-carbamic acid (1R,2S,5R)-2-isopropyl-5-methyl-cyclohexyl ester | 498.5 |
| BIO1268 | (3-Isopropoxy-propyl)-carbamic acid (1R,2S,5R)-2-isopropyl-5-methyl-cyclohexyl ester | 19.6 |
| BIO1271 | Hexyl-carbamic acid (1R,2S,5R)-2-isopropyl-5-methyl-cyclohexyl ester | 18.9 |
| BIO1301 | Methyl-carbamic acid (1S,2R,5S)-2-isopropyl-5-methyl-cyclohexyl ester | 63.9 |
| BIO1702 | (Tetrahydro-furan-2-ylmethyl)-carbamic acid (1R,2S,5R)-2-isopropyl-5-methyl-cyclohexyl ester | 14.8 |
| BIO1159 | Isobutyl-carbamic acid (1R,2S,5R)-2-isopropyl-5-methyl-cyclohexyl ester | 100.1 |
| BIO1336 | (2-Methoxy-ethyl)-carbamic acid (1R,2S,5R)-2-isopropyl-5-methyl-cyclohexyl ester | 35.3 |
| BIO1339 | (3-Methoxy-propyl)-carbamic acid (1S,2R,5S)-2-isopropyl-5-methyl-cyclohexyl ester | 53.2 |
| BIO1378 | Ethyl-carbamic acid (1S,2R,5S)-2-isopropyl-5-methyl-cyclohexyl ester | 29.3 |
| BIO1662 | (6-Hydroxy-hexyl)-carbamic acid (1R,2S,5R)-2-isopropyl-5-methyl-cyclohexyl ester | 50.7 |
| BIO1553 | Diethyl-carbamic acid (1R,2S,5R)-2-isopropyl-5-methyl-cyclohexyl ester | 10.7 |
| BIO1185 | Methyl-carbamic acid (1R,2S,5R)-2-isopropyl-5-methyl-cyclohexyl ester | 109.2 |

Example 3

Depigmenting Effect on Ex Vivo Skin

Pigmented pig skin was excised from animals (slaughtered for meat production; the pig skin model included the subcutis fat layer as described in EP 1 939 27), cut into 4×4×3 mm pieces (length×width×height) and placed in culture at the air-liquid interface on a sterilized cotton pad soaked with 5 ml of customized DMEM (Dulbecco's Modified Eagle Medium). Assays were started 24 h after sample acclimatization at 37° C., 5% CO$_2$. O/W emulsions (as described in more detail below) without (=control) and with the test compounds, respectively, were applied topically and incubated for 6 days. Histological sections were prepared and melanin granules stained by Fontana-Masson technique. The granules were quantified by image analysis.

| Test substance | Amount in wt. % | Melanin score vs. Control |
|---|---|---|
| BIO1155 | 1% | −46% |
| BIO1151 | 1% | −44% |

These data show that compounds of formula (I) according to the present invention have a depigmenting effect per quantity on ex vivo skin.

The O/W emulsions used had the following composition:

| Phase | Ingredient | INCI-Name | % by weight |
|---|---|---|---|
| A | Water | Water (Aqua) | Ad 100 |
| | Hydrolite-5 | 1,2 Pentylene Glycol | 2.00 |

-continued

| Phase | Ingredient | INCI-Name | % by weight |
|---|---|---|---|
| B | PCL liquid 100 | Cetearyl Octanoate | 3.00 |
|  | Lanette O | Cetearyl Alcohol | 2.00 |
|  | Paraffin oil 5° E | Mineral Oil | 3.00 |
|  | Eutanol G | Octyldodecanol | 4.00 |
|  | Abil 350 | Dimethicone | 0.50 |
| C | Pemulen TR1 | Acrylates/C10-30 Alkyl Acrylate Crosspolymer | 0.20 |
|  | Ultrez-21 | Acrylates/C10-30 Alkyl Acrylate Crosspolymer | 0.05 |
| D | Sodium Hydroxide, 10% solution | Sodium Hydroxide | 0.50 |
| E | BIO1155 or BIO1151 |  | 1.00 |
|  | Hydrolite-5 | 1,2 Pentylene Glycol | 3.00 |

Manufacturing Procedure:

Phases A and B are heated to 70° C. separately. Pemulen TR1 as well as Ultrez-21 are dispersed in phase B when heated to 70° C. Phase B/C is added to phase A by mixing with an Ultra Turrax, followed by emulsifying. Phase D is slowly added to phase A/B/C using a paddle mixer and a pH 5.5-6 is adjusted. The formulation is cooled down while mixing with a paddle mixer. Phase E is prepared by dissolving one or more compounds of formula (I) in Hydrolite-5. Subsequently, phase E is added to the mixture of phase A-D.

FORMULATION EXAMPLES

"Compound of List A"

Unless indicated otherwise in the respective formulation example, each compound from the following List A was formulated separately into each single formulation of the formulation examples K1-K11 and F1-F10 given below.
List A:
BIO1151, BIO1571, BIO1266, BIO1460, BIO1461, BIO1580, BIO1632, BIO1633, BIO1695, BIO1699, BIO1155, BIO1553 and BIO1185.

Additionally, several formulations were produced including mixtures of two, three of four different compounds selected from list A. In such a case, the amount used in the formulation example refers to the sum of the compounds selected from list A used therein.

In case two different compounds of list A were used as a mixture in the formulation examples given herein, generally the ratio by weight of the two compounds was chosen in the range of from 10:1 to 1:10, preferably in the range of from 5:1 to 1:5, more preferably in the range of from 3:1 to 1:3.

In formulation examples K1-K9 and K11 the following two perfume oils PFO1 and PFO2 were each used as fragrance (DPG=dipropylene glycol).
Perfume Oil PFO1 with Rose Smell

| Component/NAME | Parts by weight |
|---|---|
| Acetophenone, 10% in DPG | 10.00 |
| n-Undecanal | 5.00 |
| Aldehyde C14, so-called (peach aldehyde) | 15.00 |
| Allylamyl glycolate, 10% in DPG | 20.00 |
| Amyl salicylate | 25.00 |
| Benzyl acetate | 60.00 |
| Citronellol | 80.00 |
| d-Limonene | 50.00 |
| Decenol trans-9 | 15.00 |
| Dihydromyrcenol | 50.00 |
| Dimethylbenzylcarbinyl acetate | 30.00 |
| Diphenyloxide | 5.00 |
| Eucalyptol | 10.00 |
| Geraniol | 40.00 |
| Nerol | 20.00 |
| Geranium oil | 15.00 |
| Hexenol cis-3, 10% in DPG | 5.00 |
| Hexenyl salicylate cis-3 | 20.00 |
| Indole, 10% in DPG | 10.00 |
| Alpha-Ionone | 15.00 |
| Beta-Ionone | 5.00 |
| Lilial ® (2-methyl-3-(4-tert-butyl-phenyl)propanal) | 60.00 |
| Linalool | 40.00 |
| Methylphenyl acetate | 10.00 |
| Phenylethyl alcohol | 275.00 |
| Styrolyl acetate | 20.00 |
| Terpineol | 30.00 |
| Tetrahydrolinalool | 50.00 |
| Cinnamyl alcohol | 10.00 |
| Total: | 1,000.00 |

Perfume Oil PFO2 with White Blossom and Musk Smell

| Component/NAME | Parts by weight |
|---|---|
| Benzyl acetate | 60.00 |
| Citronellyl acetate | 60.00 |
| Cyclamenaldehyde (2-methyl-3-(4-isopropylphenyl)propanal) | 20.00 |
| Dipropylene glycol (DPG) | 60.00 |
| Ethyllinalool | 40.00 |
| Florol (2-isobutyl-4-methyltetrahydro-2H-pyran-4-ol) | 30.00 |
| Globanone ® [(E/Z)-8-cyclohexadecen-1-one] | 180.00 |
| Hedione ® (methyldihydrojasmonate) | 140.00 |
| Hexenyl salicylate, cis-3 | 10.00 |
| Vertocitral (2,4-dimethyl-3-cyclohexenecarboxaldehyde) | 5.00 |
| Hydratropaaldehyde, 10% in DPG | 5.00 |
| Isodamascone (1-(2,4,4-trimethyl-2-cyclohexen-1-yl)-2-buten-1-one, 10% in DPG | 5.00 |
| Isomuscone (cyclohexadecanone) | 40.00 |
| Jacinthaflor (2-methyl-4-phenyl-1,3-dioxolane) | 10.00 |
| Cis-jasmone, 10% in DPG | 20.00 |
| Linalool | 50.00 |
| Linalyl acetate | 30.00 |
| Methyl benzoate, 10% in DPG | 25.00 |
| para-Methyl cresol, 10% in DPG | 10.00 |
| Nerol | 20.00 |
| Phenylpropylaldehyde | 5.00 |
| 2-Phenylethyl alcohol | 82.00 |
| Tetrahydrogeraniol | 13.00 |
| 2,2-Dimethyl-3-cyclohexyl-1-propanol | 80.00 |
| Total: | 1,000.00 |

Formulation Examples K1-K11

Formulations according to the invention with compositions according to Table 1
K1=Skin Care Gel (SPF 6)
K2=Sun Protection Lotion SPF 24 (UVA/UVB Balance)
K3=Tinted Anti Aging Balm, SPF 15
K4=Body Lotion, SPF 15
K5=Skin Soothing Night Cream O/W
K6=Cream W/O
K7=Skin Care Ampoule
K8=Skin Oil
K9=Shower & Shampoo
K10=Tinted Skin Care Stick SPF 50
K11=Hair Gel

TABLE 1

Compositions of formulations according to the invention (Examples K1-K11)

| Ingredients | INCI-Name | K1 | K2 | K3 | K4 | K5 | K6 | K7 | K8 | K9 | K10 | K11 |
|---|---|---|---|---|---|---|---|---|---|---|---|---|
| Skin Lightening Ingredients | | | | | | | | | | | | |
| Compound of list A | | 0.1 | 5 | 0.05 | 0.2 | 1 | 0.5 | 0.1 | 0.5 | 0.2 | 1 | 0.5 |
| SymWhite 377 (Symrise) | Phenylethyl resorcinol | | 0.5 | | | | | | 0.1 | | | |
| beta-Arbutin | Arbutin | 1 | | | | 0.5 | | | | | 0.2 | |
| Nicotinamide | Niacinamide | | | | | 0.5 | | | | | 1 | |
| Kojic acid | Kojic acid | | | 0.5 | | | | | | | | 1 |
| Mg ascorbyl phosphate | Magnesium ascorbyl phosphate | | | 5 | | | | | | | 3 | |
| Other Ingredients | | | | | | | | | | | | |
| (−) alpha Bisabolol nat. | Bisabolol | | 0.1 | | 0.2 | | | | | 0.1 | | |
| Abil 350 | Dimethicone | | | 2 | | | | | | | | |
| Actipone ® Laminaria SaccharinaGW | Glycerin, Water (Aqua), Laminaria Saccharina Extract | | | | | | 1 | | | | | |
| Aloe Vera Gel Conc.10:1 | Aloe Barbadensis Leaf Juice | | 1 | | | | | | | | | |
| Aluminium Stearate | Aluminium Stearate | | | | | | | | 1.2 | | | |
| Amaze XT | Dehydroxanthan Gum | 1.4 | | | | | | | | | | |
| Betulin 90% (1079) | Betulin | | | | | 0.15 | | | | | | |
| Biotive ® L-Arginine | Arginine | 3.2 | 0.5 | 0.6 | 0.9 | | | | | | | |
| Biotive ® Troxerutin | Troxerutin | | 0.5 | 0.5 | | | | | | | | |
| Carbopol ETD 2020 | Acrylates/C10-30 Alkyl Acrylate Crosspolymer | 0.2 | | | | | | | | | | |
| Carbopol ETD 2050 | Carbomer | | | 0.2 | | 0.2 | | | | | | |
| Carbopol Ultrez-21 | Acrylates/C10-30 Alkyl Acrylate Crosspolymer | | | | 0.5 | | | | | | | |
| Citric Acid 10% sol. in water | Citric Acid | | | | | | | | | 3.1 | | |
| Comperlan 100 | Cocamide MEA | | | | | | | | | 1 | | |
| Corapan TQ | Diethylhexyl 2,6 Naphtalate | | | | | 3 | | | | | | |
| Crinipan ® AD | Climbazole | | | | | | | | | | | 0.1 |
| Cutina GMS V | Glyceryl Stearate | | | | | 2 | | | | | | |
| Cutina PES | Pentaerythrityl Distearate | | | 2 | | | | | | | | |
| Cutina TS | PEG-3 Distearate | | | | | | | | | 2.5 | | |
| DC9701 Cosmetic Powder | Dimethicone/Vinyl Dimethicone Crosspolymer, Silica | | | | | | | | | | 2 | |
| Dermacryl AQF | Acrylates Copolymer | | 2 | | | | | | | | | |
| Dipropylene Glycol | Dipropylene Glycol | | | | | | | | | | | 1 |
| Dow Corning 193 surfactant | PEG-12 Dimethicone | 1 | | | | | | | | | | |
| Dow Corning 246 fluid | Cyclohexasiloxane | | | 3 | | 1 | | | | | | |
| D-Panthenol 75 L | Panthenol | | | | | | | 1 | | 0.3 | | 0.5 |
| Dracorin ® CE | Glyceryl Stearate/Citrate | | | | | 3 | | | | | | |
| Dracorin ® GOC | Glyceryl Oleate Citrate, Caprylic Capric Triglyceride | | | | 1.5 | | | | | | 0.5 | |
| Drago-Beta-Glucan | Water (Aqua), Butylene Glycol, Glycerin, Avena Sativa (Oat) Kernel Extract | | | | | | 1 | | | | | |
| DragoCalm ® | Water, Glycerin, Avena Sativa (Oat Kernel Extract) | | | | | | | | 1 | | | |

TABLE 1-continued

Compositions of formulations according to the invention (Examples K1-K11)

| Ingredients | INCI-Name | % w/w | | | | | | | | | | |
|---|---|---|---|---|---|---|---|---|---|---|---|---|
| | | K1 | K2 | K3 | K4 | K5 | K6 | K7 | K8 | K9 | K10 | K11 |
| Dragocide ® Liquid | Phenoxyethanol, Methylparaben, Ethylparaben, Butylparaben, Propylparaben, Isobutylparaben | | | | | 0.8 | 0.8 | | | | | |
| Dragoderm ® | Glycerin, Triticum *Vulgare* (Wheat) Gluten, Water (Aqua) | | | | | | 2 | | | | | |
| Dragosan W/O P | Sorbitan Isostearate, Hydrogenated Castor Oil, Ceresin, Beeswax (*Cera Alba*) | | | | | | 8 | | | | | |
| Dragosantol ® 100 | Bisabolol | | | | 0.1 | | 0.2 | | | | | |
| Dragosine ® | Carnosine | 0.2 | | | | | | 0.2 | | | | |
| Dragoxat ® 89 | Ethylhexyl Isononanoate | | 2 | 5 | | 4 | 7 | | 15 | | 5 | |
| EDTA B | Tetrasodium EDTA | | | | | | | 0.1 | | | | |
| EDTA BD | Disodium EDTA | | 0.1 | 0.1 | 0.1 | | | | | | | 0.1 |
| Emulsiphos ® | Potassium Cetyl Phosphate, Hydrogenated Palm Glycerides | | 2 | 2 | | | | | | | | |
| Ethanol | Ethanol | 10 | | | | | | | | | | |
| Extrapone ® Ginkgo Biloba | Propylene Glycol, Water (Aqua), Ginkgo Biloba Leaf Extract, Glucose, Lactic Acid | | | | | 1 | | | | | | |
| Food Color Brown E172 + E171 Powder | Color | | | 2 | | | | | | | 3 | |
| Fragrance PFO1 or PFO2 | Parfum | 0.1 | 0.2 | 0.3 | 0.2 | 0.4 | 0.3 | 0.1 | 0.5 | 1 | | 0.1 |
| Frescolat ® MGA | Menthone Glycerin Acetal | | | | | | | 0.1 | | | | |
| Frescolat ® ML | Menthyl Lactate | | | | | | | | | | 0.2 | |
| Fruitapone ® Orange B | Propylene Glycol, Water (Aqua), Citric Acid, Citrus *Aurantium Dulcis* (Orange) Juice, Trideceth-9, Bisabolol | | | | | | | | | | | 0.5 |
| Glycerine 99.5% | Glycerin | 2.5 | 3 | | | 5 | 3 | | | 0.5 | | 10 |
| Hydrolite ®-5 | Pentylene Glycol | 3 | 2 | | 5 | | | | | 1 | | |
| Hydroviton ®-24 | Water, Pentylene Glycol, Glycerin, Lactic Acid, Sodium Lactate, Serine, Urea, Sorbitol, Sodium Chloride, Allantoin | | | | | 1 | 1 | | 10 | | | |
| Iso Adipat | Diisopropyl Adipate | | | | 1 | | | | 5 | | | |
| Isodragol ® | Triisononanoin | | 2 | | | | | | | | | |
| Isopropyl Palmitate | Isopropyl Palmitate | | | | | | | | | | 13 | |
| Jaguar C-162 | Hydroxypropyl Guar, Hydroxypropyltrimonium Chloride | | | | | | | | | 0.1 | | |
| Jojoba Oil | Simmondsia Chinensis (Jojoba) Seed Oil | 1 | | | | | 2 | | | | | |
| Keltrol CG RD | Xanthan Gum | | 0.4 | 0.2 | 0.2 | 0.1 | | 0.05 | | | | |
| Lanette 16 | Cetyl Alcohol | | 1 | | | | | | | | | |
| Lanette O | Cetearyl Alcohol | | 0.5 | | | 3 | | | | | 5 | |
| Lara Care A-200 | Galactoarabinan | | 0.3 | | | | | | | | | |
| Luviskol K30 Powder | PVP | | | | | | | | | | | 3 |
| Magnesium Sulfate | Magnesium Sulfate | | | | | | 0.7 | | | | | |

TABLE 1-continued

Compositions of formulations according to the invention (Examples K1-K11)

| Ingredients | INCI-Name | K1 | K2 | K3 | K4 | K5 | K6 | K7 | K8 | K9 | K10 | K11 |
|---|---|---|---|---|---|---|---|---|---|---|---|---|
| Mineral Oil | Mineral Oil | | | | | | 8 | | ad 100 | | | |
| Neo Heliopan ® 303 | Octocrylene | | 10 | 4 | | | | | | | 10 | |
| Neo Heliopan ® 357 | Butylmethoxydibenzoyl-methane | | 3 | 2 | 3 | | | | | | 5 | |
| Neo Heliopan ® AP | Disodium Phenyl Dibenzimidazole Tetrasulfonate | 3 | | | | | | | | | | |
| Neo Heliopan ® AP, 15% sol., neutralized with Biotive ® L-Arginine | Aqua, Disodium Phenyl Dibenzimidazole Tetrasulfonate, Arginin | | 6.7 | 6.7 | | | | | | | | |
| Neo Heliopan ® E 1000 | Isoamyl p.Methoxycinnamate | | 1 | | | | | | | | | |
| Neo Heliopan ® HMS | Homosalate | | 5 | | 5 | | | | | | | |
| Neo Heliopan ® Hydro, 20% sol., neutralized with Biotive ® L-Arginine | Aqua, Phenylbenzimidazole Sulphonic Acid, Arginin | | 10 | 10 | 10 | | | | | | | |
| Neo Heliopan ® MBC | 4-Methylbenzylidene Camphor | 1 | | | | | | | | | | |
| Neo Heliopan ® OS | Ethylhexyl Salicylate | | | 3 | 5 | | | | | | | |
| Neutral Oil | Caprylic/Capric Triglyceride | | | | | 6 | | | | | 13.7 | |
| Ozokerite Wax 2389 | Ozokerite | | | | | | | 2 | | | | |
| PCL-liquid 100 | Cetearyl Ethylhexanoate | | | 2 | 4 | 5 | | | | | | |
| PCL-Solid | Stearyl Heptanoate, Stearyl Caprylate | | | | | 3 | | | 0.5 | | | |
| Phytoconcentrole ® Coconut | Caprylic/Capric Triglyceride, Coconut (*Cococ Nucifera*) Oil | | | | | | | | 1 | | | |
| Rewoderm LI S80 | PEG-200 Hydrogenated Palmitate, PEG-7 Glyceryl Cocoate | | | | | | | | | 0.25 | | |
| Rewopol SBFA30 | Disodium Laureth Sulfosuccinate | | | | | | | | | 8 | | |
| Silcare Silicone 41M65 | Stearyl Dimethicone | | 1 | | | | | | 21 | | | |
| Sodium Chloride | Sodium Chloride | | | | | | | | | 1.7 | | |
| Sodium Hydroxide 10% sol. | Sodium Hydroxide | | | | | 0.9 | | | | | | |
| Solubilizer | PEG-40 Hydrogenated Castor Oil, Trideceth-9, Propylene Glycol, Water (Aqua) | | | | | | | | 1.5 | | | 0.5 |
| SymCalmin ® | Pentylene Glycol, Butylene Glycol, Hydroxyphenyl Propamidobenzoic Acid | | | | | 1 | | | | | | |
| SymClariol ® | Decylene Glycol | | | 0.5 | | | | | | | | |
| SymDiol ® 68 | 1,2 Hexanediol, Caprylyl Glycol | 0.6 | | | | | | 1 | | | | |
| SymGlucan ® | Water (Aqua) Glycerin, Beta Glucan | | 2 | | 2 | 1 | | 5 | | | | |
| SymHelios ® 1031 | Benzylidene Dimethoxydimethyl-indanone | | | 0.5 | 0.5 | | | | | | | |
| SymMatrix ® | Maltodextrin, *Rubus Fruticosus* (Blackberry) Leaf Extract | | | | | | 0.5 | | | | | |
| SymMollient ® L | Neopentyl Glycol Diisononanoate | | | | 2 | | | | | | 5 | |

TABLE 1-continued

Compositions of formulations according to the invention (Examples K1-K11)

| Ingredients | INCI-Name | K1 | K2 | K3 | K4 | K5 | K6 | K7 | K8 | K9 | K10 | K11 |
|---|---|---|---|---|---|---|---|---|---|---|---|---|
| SymMollient ® S | Cetearyl Nonanoate | | | | 1 | | | | | | 4 | |
| SymMollient ® W/S | Trideceth-9, PEG-5 Isononanoate | | | | | | | 2 | | | | |
| SymRelief ® | Bisabolol, *Zingiber Officinale* (Ginger) Root Extract | | 0.1 | | | 0.2 | | | 0.1 | | | |
| SymRepair ® | Hexyldecanol, Bisabolol, Cetylhydroxyproline Palmitamide, Stearic Acid, Brassica Campestris (Rapeseed Sterols) | | | 1 | | | 3 | | | | | |
| SymSitive ® 1609 | Pentylene Glycol, 4-t-Butylcyclohexanol | | | | | 0.5 | | | | | | |
| SymVital ® | *Aloe Barbadensis* Leaf Juice Powder, Magnesium Ascorbyl Phosphate, *Rubus Idaeus* (Raspberry) Leaf Extract | 0.5 | | | | | | | 0.1 | | | |
| Tinosorb S | Bis-Ethylhexyloxyphenol, Methoxyphenyl Triazine | | | | | | | | | | 3 | |
| Tapioca Pure | Tapioca Starch | | | 5 | | | | | | | | |
| TeCe-Ozokerit N502 | Ozokerite | | | | | | | | | | | ad 100 |
| Tego Betain L7 | Cocoamidopropyl Betaine | | | | | | | | | 5 | | |
| Tegosoft TN | C12-15 Alkyl Benzoate | | | | | 5 | | | | | | |
| Texapon N70 | Sodium Laureth Sulfate | | | | | | | | | 15 | | |
| Triethanolamine 99% | Triethanolamine | | | | | | | | | | | 0.5 |
| Vitamin E acetat | Tocopherol Acetate | | 0.5 | 0.5 | 0.5 | | 0.2 | | 0.5 | | 0.7 | |
| Wacker-Belsil CDM3526 VP | C26-C28 Alkyl Dimethicone | | | | | | | | | | 2 | |
| Water, demin. | Water (Aqua) | ad 100 | ad 100 | ad 100 | ad 100 | ad 100 | ad 100 | ad 100 | | ad 100 | | ad 100 |

EXAMPLES: F1-F10

Orally Consumable Use Examples ["Beauty from Inside"]

Example F1

Fruit Gums

| | % by weight |
|---|---|
| Water | Ad 100 |
| Saccharose | 34.50 |
| Glucose syrup, DE 40 | 31.89 |
| Iso Syrup C* Tru Sweet 01750 (Cerestar GmbH) | 1.50 |
| Gelatin 240 Bloom | 8.20 |
| Yellow and red food colourants | 0.01 |
| Citric acid | 0.20 |
| Compound of list A | 0.075 |

Example F2

Hard Boiled Candy

| | I (% by weight) | II (% by weight) |
|---|---|---|
| Sugar (Saccharose) | Ad 100 | Ad 100 |
| High fructose corn syrup | 41.00 | 41.00 |
| Maltose | 3.00 | 3.00 |
| Palm kernel oil | 0.90 | 0.90 |
| Citric acid | 0.30 | 0.30 |
| Ginger extract | 0.40 | — |
| Ginseng extract | — | 0.40 |
| Blue colourant | 0.01 | 0.01 |
| Compound of list A | 0.10 | 0.25 |
| Honey | — | 1.50 |
| Honey flavour | — | 0.30 |

Example F3

Gelatin Capsules Suitable for Direct Consumption

| | % by weight | | |
|---|---|---|---|
| | I | II | III |
| Gelatin shell: | | | |
| Glycerin | 2.014 | 2.014 | 2.014 |
| Gelatin 240 Bloom | 7.91 | 7.91 | 7.91 |
| Aspartame | 0.05 | — | — |
| Sucralose | 0.035 | 0.050 | 0.070 |
| Allura Red (red colourant) | 0.006 | 0.006 | 0.006 |
| Brilliant Blue (blue colourant) | 0.005 | 0.005 | 0.005 |
| Core composition: | | | |
| Plant oil triglyceride (coconut oil fraction) | to 100 | to 100 | to 100 |
| Flavour G | 9.95 | 12.0 | 12.0 |
| Compound of list A | 0.07 | 0.20 | 0.50 |

Flavour G had the following composition here (in wt. %): 0.1% neotam powder, 29.3% peppermint oil arvensis, 29.35% peppermint piperta oil Willamette, 2.97% sucralose, 2.28% triacetin, 5.4% diethyl tartrate, 12.1% peppermint oil yakima, 0.7% ethanol, 3.36% 2-hydroxyethylmenthylcarbonate, 3.0% 2-hydroxypropylmenthylcarbonate, 5.77% D-limonene, 5.67% L-menthylacetate.

The gelatin capsules I, II, III suitable for direct consumption were produced according to WO 2004/050069 and in each case had a diameter of 5 mm and the weight ratio of the core material to the shell material was 90:10. The capsules in each case opened in the mouth within less than 10 seconds and dissolved completely within less than 50 seconds.

Example F4

Tablets in Round Tablet Form

| | % by weight | | |
|---|---|---|---|
| | I | II | III |
| Magnesium stearate | 0.9 | 0.9 | 0.9 |
| Citric acid | 0.2 | 0.2 | 0.2 |
| Compound of list A | 0.05 | 0.20 | 0.50 |
| Dextrose | to 100 | to 100 | to 100 |

Example F5

Chewing Gum (with Sugar and Sugar-Free)

| | % by weight | |
|---|---|---|
| | I | II |
| Chewing gum base | 21.0 | 30.0 |
| Glycerin | 0.5 | 1.0 |
| Menthol spearmint eucalyptus flavour P1 | 1.0 | 1.4 |
| Glucose syrup | 16.5 | — |
| Powder sugar | to 100 | — |
| Compound of list A | 0.15 | 0.20 |
| Sorbitol (in powder form) | — | to 100 |
| Palatinit | — | 9.5 |
| Xylitol | — | 2.0 |
| Mannitol | — | 3.0 |
| Aspartame | — | 0.1 |
| Acesulfame K | — | 0.1 |
| Emulgum (emulsifier) | — | 0.3 |
| Sorbitol 70%, in water | — | 14.0 |

Flavour P1 had the following composition (in wt. %): 0.05% isobutyraldehyde, 0.05% 3-octanol, 0.05% dimethylsulfide, 0.1% trans-2-hexanal, 0.1% cis-3-hexanol, 0.1% natural 4-terpineol, 0.1% isopulegol, 0.2% natural piperiton, 0.3% linalool, 1.0% isoamylalcohol, 1.0% isovaleraldehyde, 2.5% natural alpha-pinene, 2.5% natural beta-pinene, 8.0% eucalyptol, 7.0% 1-menthylacetate, 12.0% 1-menthone, 5.0% isomenthone, 20.5% I-carvone, 39.45% I-menthol.

The following table relates to Examples F6-F10:

Example F6

Instant Drink Powder

Example F7

Instant Drink Powder, Sugar-Free

Example F8

Carbonated Lemonade (Soft Drink)

Example F9

Soya Fruit Drink

Example F10

Reduced-Fat Yoghourt

| | % by weight | | | | |
|---|---|---|---|---|---|
| | F6 | F7 | F8* | F9 | F10 |
| Compound of list A | 0.50 | 0.70 | 0.10 | 0.05 | 0.20 |
| Sugar (Saccharose) | to 100 | | | | |
| Citric acid | 4.00 | 33.33 | 0.2 | | |
| Trisodium citrate | 0.26 | | | | |
| Tricalcium phosphate | 0.22 | | | | |
| Ascorbic acid (Vitamin C) | 0.24 | 0.44 | | | |
| Opacifier and Titanium dioxide (E 171) | 0.20 | | | | |
| Xanthan gum (E 415) | 0.072 | | | | |
| Sodiumcarboxy-methylcellulose (E 467) | 0.064 | | | | |
| Pectin (E 440) | 0.04 | | | | |
| Spray-dried pineapple flavour, contains yellow colourant tartrazine | 0.40 | | | | |
| Spray-dried raspberry flavour, contains red colorant | | 11.50 | | | |
| Lemon-lime flavour | | | 0.01 | | |
| D-Limonene | | | 0.005 | | |

-continued

| | % by weight | | | | |
|---|---|---|---|---|---|
| | F6 | F7 | F8* | F9 | F10 |
| Maltodextrin (powder) | | to 100 | | | |
| Aspartame | | 3.30 | | | |
| Saccharose | | | 8.0 | 6.0 | 5.0 |
| Hesperetin (1% by weight in 1,2-propyleneglycol) | | | 0.05 | | |
| Ethylhydroxymethyl furanone | | | 0.01 ppb | | |
| Vanilla flavour | | | | 0.10 | 0.125 |
| Vanillin | | | 15 ppb | | |
| Maltol | | | 350 ppb | | |
| 2,5-dimethyl-4-hydroxy-2H-furan-3-one | | | 3 ppb | | |
| 1,2-Propylene glycol | | | | 0.1 | |
| Mixture of fruit juice concentrates | | | | 45.0 | |
| Soya powder | | | | 5.0 | |
| Yoghurt (1.5% by weight fat) | | | | | to 100 |
| Water | | | to 100 | to 100 | |

*Carbon dioxide is added after filling into bottles.

The invention claimed is:

1. A cosmetic or pharmaceutical composition for lightening of skin and/or hair, comprising (a) 0.001 wt. % to 30 wt. % of one or more compounds selected from the group consisting of

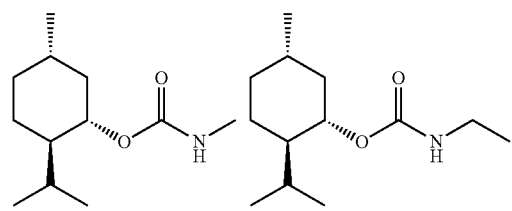

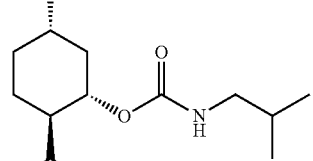

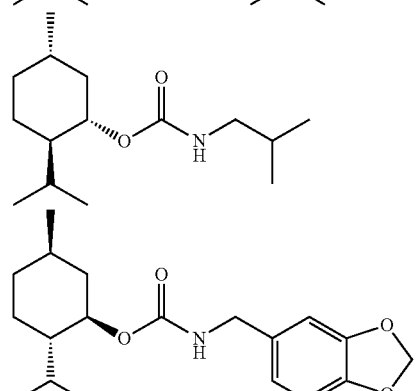

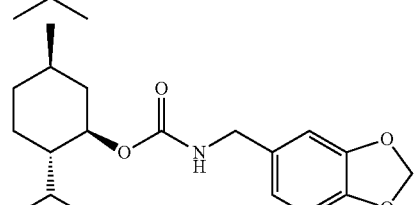

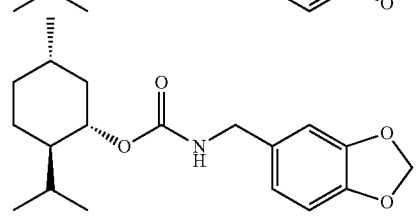

-continued

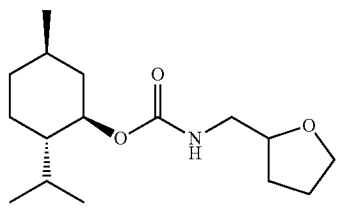

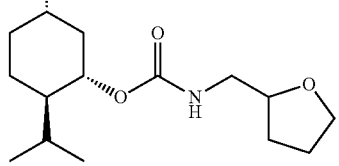

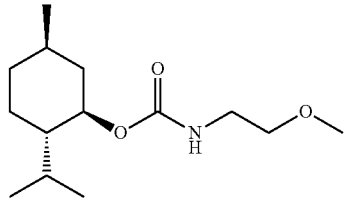

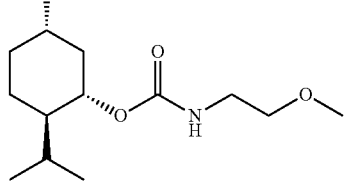

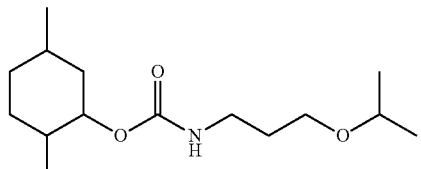

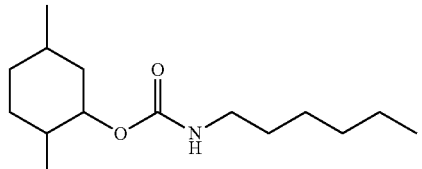

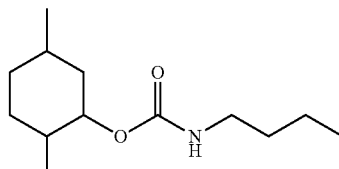

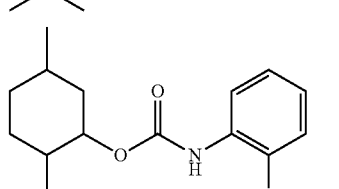

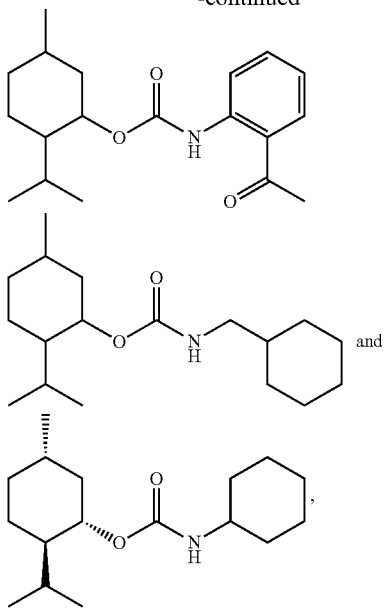

or a cosmetically acceptable salt thereof; and (b) 0.01 wt. % to 30 wt. % of one or more further active ingredients for skin and/or hair lightening suitable for cosmetic or pharmaceutical application selected from the group consisting of kojic acid (5-hydroxy-2-hydroxymethyl-4-pyranone), kojic acid derivatives, arbutin, ascorbic acid, ascorbic acid derivatives, hydroquinone, hydroquinone derivatives, resorcinol, resorcinol derivatives, sulfur-containing molecules, alpha-hydroxy acids, salts and esters thereof, tyrosinase inhibitors, N-acetyl tyrosine and derivatives, undecenoyl phenylalanine, gluconic acid, chromone derivatives, zinc salts, thujaplicin and derivatives, triterpenes, sterols, benzofuranones, vinyl guiacol, ethyl guiacol, dionic acids, inhibitors of nitrogen oxide synthesis, 2,7-dinitroindazole or thiocitrulline, metal chelators, retinoids, soy milk and extract, serine protease inhibitors or lipoic acid or other synthetic or natural active ingredients for skin and hair lightening.

2. A composition according to claim 1, wherein the one or more further active ingredients for skin and/or hair lightening of component (b) are selected from the group consisting of kojic acid, phenylethyl resorcinol, beta- and alpha-arbutin, hydroquinone, nicotinamide, dioic acid, Mg ascorbyl phosphate and vitamin C and its derivatives, mulberry extract, Bengkoang extract, *papaya* extract, turmeric extract, nutgrass extract, licorice extract (containing glycyrrhizin), alpha-hydroxy-acids, 4-alkylresorcinols, and 4-hydroxyanisole.

3. A composition according to claim 1, wherein the one or more further active ingredients for skin and/or hair lightening of component (b) are tyrosinase inhibitors.

4. A composition according to claim 1, additionally comprising
one or more agents selected from the group of substances which absorb or reflect UV radiation, and/or
one or more agents selected from the group of anti-irritants and anti-inflammatory substances, and/or
one or more agents selected from the group of antioxidants.

5. A composition according to claim 4, wherein the composition comprises 0.01 wt. % to 40 wt. % of one or more agents selected from the group of substances which absorb or reflect UV radiation.

6. A compound selected from the group consisting of:

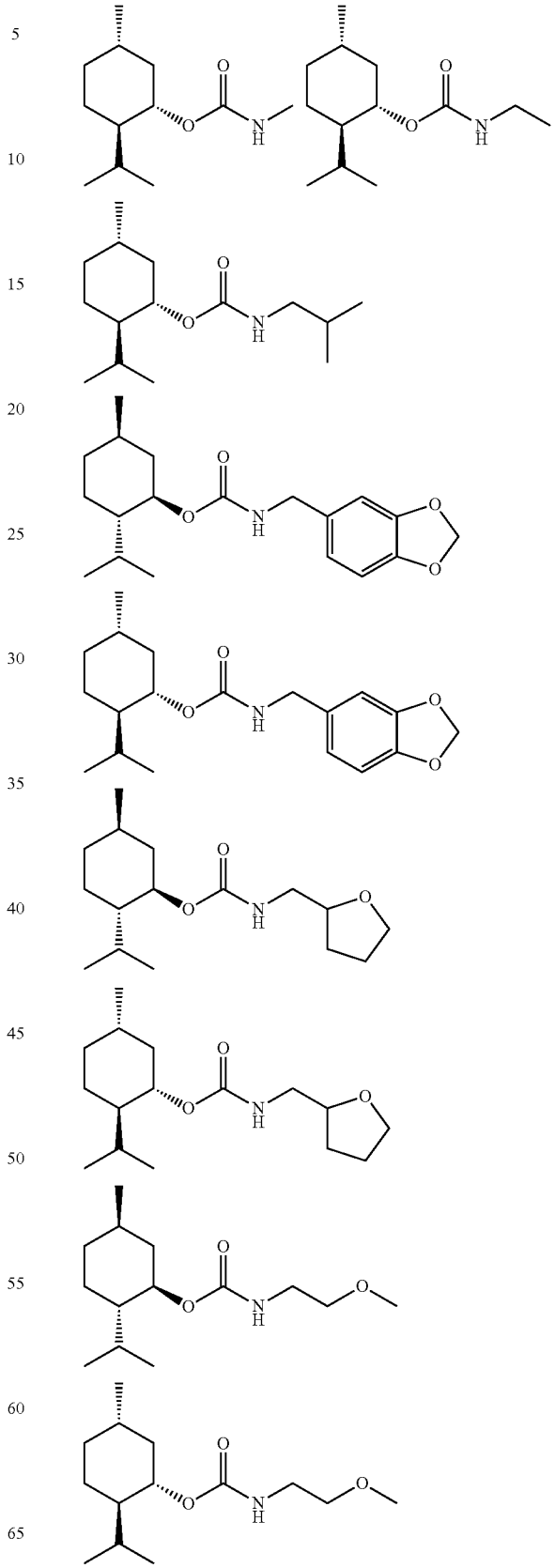

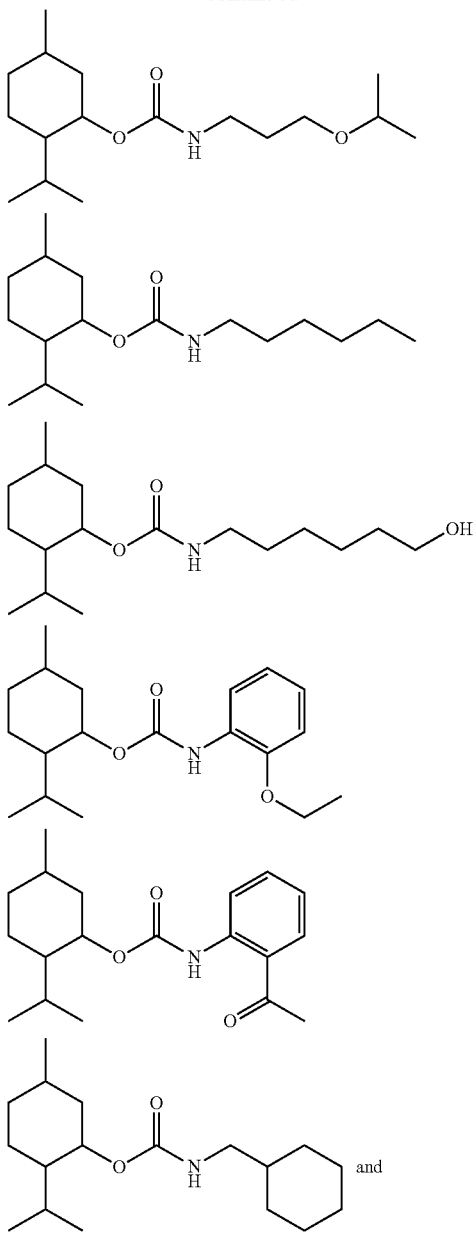

or a cosmetically acceptable salt thereof.

7. A method for the cosmetic lightening of skin and/or hair, comprising:
application to the skin and/or hair a cosmetically effective amount of a composition as defined in claim 1.

8. A drug for lightening skin and/or hair, or for treating hyperpigmentation, comprising a composition as defined in claim 1.

9. A pharmaceutical composition comprising a pharmaceutically active amount of one or more compounds of claim 6, and/or a cosmetically acceptable salt thereof, for lightening skin and/or hair, or for treating hyperpigmentation.

10. A method of lightening skin and/or hair, comprising:
application of a pharmaceutically effective amount of a composition according to claim 1 to the skin and/or hair.

11. A method for lightening the skin and/or hair comprising applying to the skin and/or hair one or more compounds of claim 6, and/or a cosmetically acceptable salt thereof.

12. A composition according to claim 5, wherein
the total quantity of the one or more compounds of (a) and/or pharmaceutically acceptable salts thereof is in the range of from 0.01 wt. % to 20 wt. %, and/or
the total quantity of further active ingredients for skin and/or hair lightening of component (b) is in the range of from 0.01 wt. % to 20 wt. %, and/or
the total quantity of substances which absorb or reflect UV radiation is in the range of from 0.1 wt. % to 30 wt. %,
in each case based on the total weight of the composition.

13. A composition according to claim 5, wherein
the total quantity of the one or more compounds of (a) and/or pharmaceutically acceptable salts thereof is in the range of from 0.01 wt. % to 5 wt. %, and/or
the total quantity of further active ingredients for skin and/or hair lightening of component (b) is in the range of from 0.01 wt. % to 5 wt. %, and/or
the total quantity of substances which absorb or reflect UV radiation is in the range of from 1.0 wt. % to 10.0 wt. %,
in each case based on the total weight of the composition.

* * * * *